(12) United States Patent
Hoffman

(10) Patent No.: US 11,723,649 B2
(45) Date of Patent: Aug. 15, 2023

(54) QUICK, ONE-HANDED INTERRUPTED SUTURE FIXATION FOR APPROXIMATING TISSUE WITHOUT THE NEED TO TIE KNOTS

(71) Applicant: Mentor Worldwide LLC, Irvine, CA (US)

(72) Inventor: Michael Hoffman, Hillsborough, NJ (US)

(73) Assignee: MENTOR WORLDWIDE LLC, Irvine, CA (US)

( * ) Notice: Subject to any disclaimer, the term of this patent is extended or adjusted under 35 U.S.C. 154(b) by 327 days.

(21) Appl. No.: 16/940,592

(22) Filed: Jul. 28, 2020

(65) Prior Publication Data

US 2022/0031300 A1 Feb. 3, 2022

(51) Int. Cl.
*A61B 17/04* (2006.01)

(52) U.S. Cl.
CPC .. *A61B 17/0401* (2013.01); *A61B 2017/0404* (2013.01); *A61B 2017/0406* (2013.01); *A61B 2017/0409* (2013.01); *A61B 2017/0445* (2013.01)

(58) Field of Classification Search
CPC ................ A61B 2017/0404; A61B 2017/0445
See application file for complete search history.

(56) References Cited

U.S. PATENT DOCUMENTS

| | | | |
|---|---|---|---|
| 5,405,352 A * | 4/1995 | Weston | A61B 17/0469 606/139 |
| 7,390,332 B2 | 6/2008 | Selvitelli et al. | |
| 8,696,704 B2 | 4/2014 | Selvitelli et al. | |
| 9,198,648 B2 | 12/2015 | Crombie et al. | |
| 9,439,644 B2 | 9/2016 | Lizardi | |
| 9,517,060 B2 | 12/2016 | Flint | |
| 10,034,663 B1 | 7/2018 | Nason et al. | |

(Continued)

FOREIGN PATENT DOCUMENTS

| | | |
|---|---|---|
| EP | 3248549 | 11/2017 |
| EP | 3415101 | 12/2018 |
| WO | 2004037094 | 5/2004 |

OTHER PUBLICATIONS

International Search Report issued in corresponding International Application No. PCT/IB2021/056872, dated Oct. 28, 2021, 6 pages.

*Primary Examiner* — Alexander J Orkin
(74) *Attorney, Agent, or Firm* — Troutman Pepper Hamilton Sanders LLP

(57) ABSTRACT

A suture implant for approximating tissue without tying knots includes a suture having a first end with a fixed knot, a second end, and a slip knot located between the first and second ends, which defines a large suture loop having a length. The slip knot defines a dynamic end of the large suture loop that is located opposite a closed end of the large suture loop. A tissue anchor is coupled with the first end of the suture. Pulling the second end of the large suture loop away from the slip knot slides the slip knot and the tissue anchor toward the closed end of the large suture loop and reduces the length of the large suture loop. The suture implant includes a needle having a leading end and a trailing end and a small suture loop secured to the trailing end of the needle that is coupled with the closed end of the large suture loop.

10 Claims, 36 Drawing Sheets

(56) References Cited

U.S. PATENT DOCUMENTS

| | | | |
|---|---|---|---|
| 10,675,015 B2 | 6/2020 | Guo et al. | |
| 2002/0019649 A1* | 2/2002 | Sikora | A61B 17/0401 |
| | | | 606/232 |
| 2004/0147958 A1* | 7/2004 | Lam | A61B 17/3478 |
| | | | 606/232 |
| 2008/0177302 A1* | 7/2008 | Shurnas | A61B 17/0401 |
| | | | 606/228 |
| 2009/0024144 A1 | 1/2009 | Zeiner et al. | |
| 2012/0083837 A1* | 4/2012 | Ferragamo | A61B 17/06004 |
| | | | 606/232 |
| 2012/0323275 A1* | 12/2012 | Crombie | A61B 17/0401 |
| | | | 606/232 |
| 2013/0023928 A1 | 1/2013 | Dreyfuss | |
| 2017/0095363 A1* | 4/2017 | Hiernaux | A61B 17/0401 |
| 2017/0340319 A1* | 11/2017 | Viola | A61B 17/06109 |
| 2019/0015091 A1 | 1/2019 | Guo et al. | |
| 2020/0360010 A1* | 11/2020 | Stauffer | A61B 17/0401 |

* cited by examiner

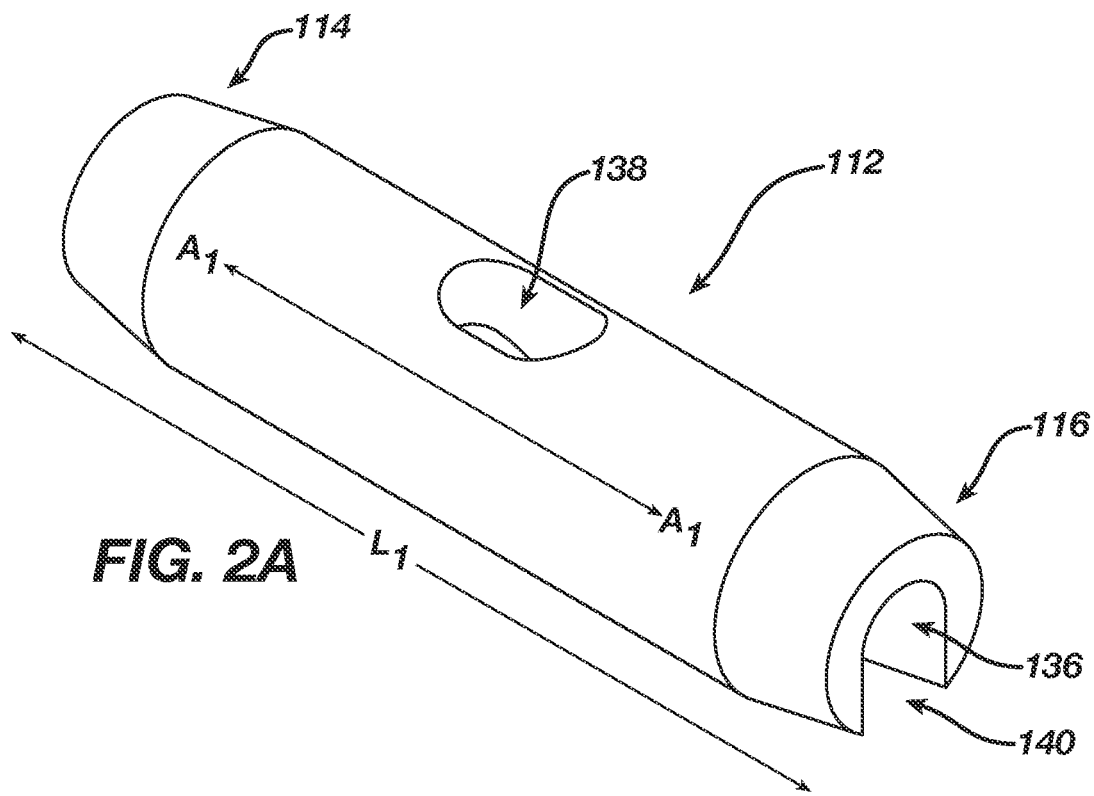
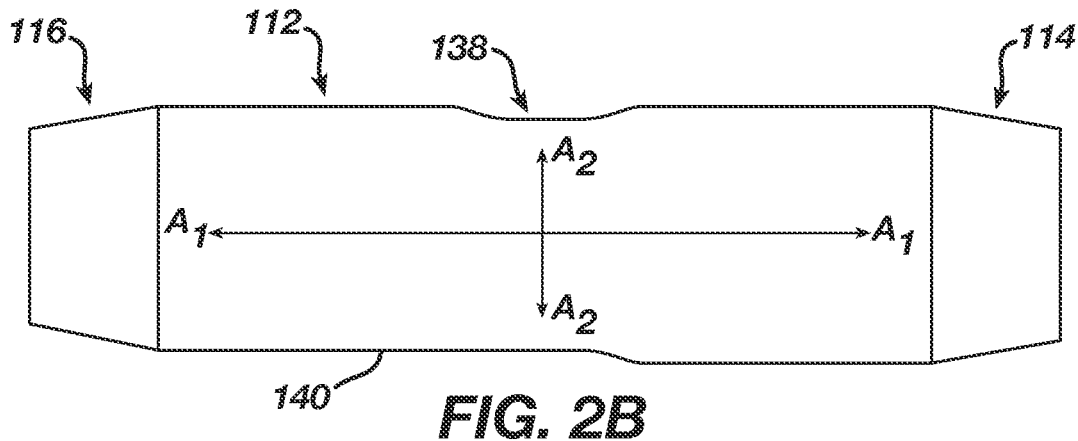
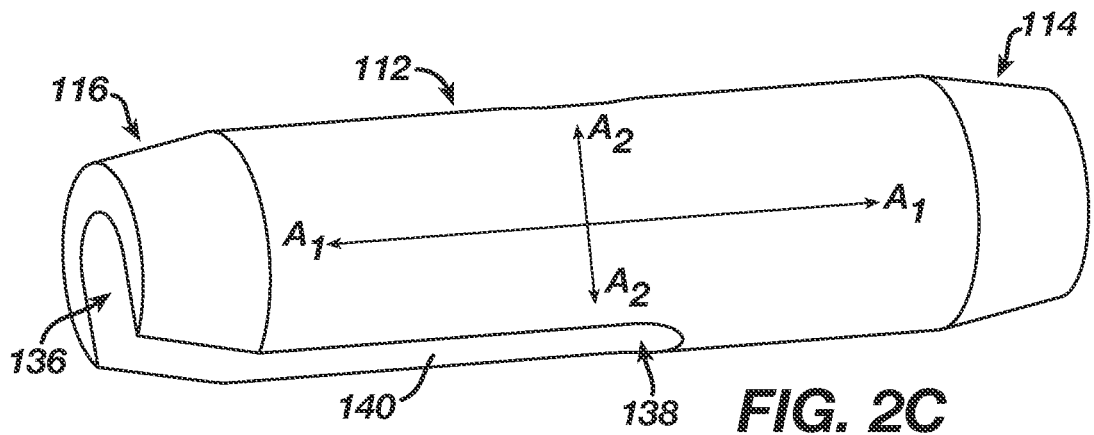

QUICK, ONE-HANDED INTERRUPTED SUTURE FIXATION FOR APPROXIMATING TISSUE WITHOUT THE NEED TO TIE KNOTS

BACKGROUND OF THE INVENTION

Field of the Invention

The present patent application is generally related to medical devices and surgical procedures, and is more particularly related to systems, devices and methods used to approximate tissue.

Description of the Related Art

Tissue approximation is an important part of most surgical procedures. The traditional means by which to approximate tissue involves the use of a surgical suture attached to a curved needle. The use of curved needles and sutures can be time consuming and challenging in many surgical procedures, particularly in difficult to access spaces, for large wounds, and/or when target tissue is difficult to penetrate.

The use of a tissue anchor attached to a suture can improve the efficiency of tissue approximation. Some devices have been known to incorporate slip knots. For example, U.S. Pat. No. 9,198,648, the disclosure of which is hereby incorporated by reference herein, describes a device including a single strand of suture that is coupled to a first tissue anchor at one end, forms a slip knot and also passes through a channel in a second tissue anchor. To tighten this device to approximate tissue a user must overcome the additional frictional forces of the suture filament sliding through the small channel in the second anchor.

Another known device described in U.S. Patent Publication No. 2009/0024144 also has a single suture filament coupled to a first tissue anchor at one end, forms a slip knot and instead of passing through a channel in the second anchor, passes through a knot in a second suture filament used for the sole purpose of tying the second suture anchor to the first suture filament as shown in FIG. 11 of the publication. This device suffers from the same drawback in that to tighten the device to approximate tissue requires overcoming the additional frictional forces of the first suture filament passing through the knot that secures the second tissue anchor to the device.

U.S. Pat. No. 9,517,060, assigned to Ethicon, Inc. of Somerville, N.J., the disclosure of which is hereby incorporated by reference herein, teaches a wound closure device having a first tissue anchor with a first suture filament fixedly coupled thereto at a proximal end and extending along a length to a free distal end, and a second tissue anchor with a second suture filament fixedly coupled thereto at a proximal end and extending along a length to a free distal end. The first suture filament is configured to form a slip knot at its proximal end substantially adjacent the first tissue anchor, and the second suture is configured to form a slip knot at its proximal end substantially adjacent the second tissue anchor. The length of the first suture filament passes through the slip knot of the second suture and the length of the second suture filament passes through the slip knot of the first suture filament.

U.S. Pat. No. 10,675,015, assigned to Ethicon, Inc. of Somerville, N.J., the disclosure of which is hereby incorporated by reference herein, teaches a system for deploying a suture implant including a delivery device and a suture implant coupled with the distal end of the delivery device. The suture implant includes a suture and a slip knot that defines a suture loop. The slip knot defines a dynamic end of the suture loop that is located opposite a closed end of the suture loop. The suture implant includes a tissue anchor having first and second openings, whereby the closed end of the suture loop passes through the first and second openings for securing the tissue anchor to the suture loop. A tensioner is secured to the first end of the suture, and a pledget, located between the tensioner and the tissue anchor, is secured to the second end of the suture, Pulling the tensioner away from the tissue anchor slides the pledget and the slip knot toward the tissue anchor for shortening the length of the suture loop and reducing the distance between the pledget and the tissue anchor.

In spite of the above-noted advances, there remains a need for improved interrupted suture implants that may be used to approximate tissue without tying knots.

SUMMARY OF THE INVENTION

In one embodiment, a suture implant preferably allows a surgeon or an assistant to apply an interrupted suture using a standard suture needle without the need to tie knots.

In one embodiment, fixation may be similar to using a standard interrupted suture loop that is deployed with a standard suture needle.

In one embodiment, fixation is very similar to a standard interrupted suture loop. However, instead of tying a knot, the anchor/pledget may be pulled through and catches on a suture loop and locks it in place.

In another embodiment, fixation is point-to-point wherein each anchor/pledget is held against opposite tissue fascial planes.

In one embodiment, a suture implant for approximating tissue without tying knots, such as an interrupted suture implant, preferably includes a suture having a first end including a fixed knot, a second end, and a slip knot that is located between the first and second ends of the suture that defines a suture loop having a length. In one embodiment, the slip knot preferably defines a dynamic end of the suture loop that is located opposite a closed end of the suture loop.

In one embodiment, a first tissue anchor may be secured to the first end of the suture by the fixed knot, and a second tissue anchor may be coupled with the closed end of the suture loop.

In one embodiment, the suture implant for approximating tissue without tying knots preferably includes a single suture strand having a leading end and a trailing end. In one embodiment, the trailing end of the suture strand is preferably attached to a leading end of the first tissue anchor.

In one embodiment, the suture implant desirably includes a needle having a leading end and a trailing end that is attached to the leading end of the single suture strand. The needle may be used for passing at least a portion of the suture implant through one or more tissue layers.

In one embodiment, after the suture implant has been passed through the one or more tissue layers, the second end of the suture may be pulled away from the slip knot for sliding the slip knot toward the closed end of the suture loop to reduce the distance between the first and second tissue anchors.

In one embodiment, the needle has a maximum cross-sectional dimension, and the first tissue anchor has a maximum cross-sectional dimension that is less than or equal to the maximum cross-sectional dimension of the needle for minimizing drag as the first tissue anchor is pulled through a pathway in tissue formed by the needle.

In one embodiment, the leading end of the first tissue anchor may be tapered for reducing drag as the first tissue anchor is pulled through tissue. In one embodiment, the tissue anchor may have a larger cross-section than the needle, however, the tapered leading end of the tissue anchor preferably enables the larger cross-section tissue anchor (i.e., compared to the cross-section of the needle) to pass through a pathway in tissue that has been pre-formed by the needle.

In one embodiment, the first tissue anchor preferably includes a cylindrical body defining the leading end and the trailing end of the first tissue anchor, an elongated channel extending from the leading end to the trailing end of the first tissue anchor, a laterally extending channel that intersects the elongated channel, and an elongated opening formed in an underside of the cylindrical body that extends from the trailing end of the cylindrical body to the laterally extending channel.

In one embodiment, the first end of the suture preferably passes through the elongated channel of the first tissue anchor, and the slip knot is at least partially seated within the elongated opening formed in the underside of the cylindrical body of the first tissue anchor.

In one embodiment, the fixed knot may be aligned with the elongated channel adjacent the trailing end of the first tissue anchor for securing the first tissue anchor to the first end of the suture.

In one embodiment, the second tissue anchor preferably has a cylindrical-shaped body, and an opening in the second tissue anchor desirably receives the suture loop. In one embodiment, the opening for the suture loop may extend through a center of the cylindrical-shaped body of the second tissue implant.

In one embodiment, the second tissue anchor is free to slide and/or toggle along the length of the suture loop.

In one embodiment, the first and second tissue anchors may be identical in size, shape, and configuration.

In one embodiment, a method of using a suture implant for approximating tissue without tying knots preferably includes passing the leading end of the needle through first and second tissue layers to form a pathway through the first and second tissue layers, and after forming the pathway, using the needle and the single suture strand for pulling the first tissue anchor, the slip knot, and the second end of the suture through the pathway that has been formed in the first and second tissue layers.

In one embodiment, the method may include, after the pulling step, cutting the single suture strand for detaching the needle and the single suture strand from the first tissue anchor, and pulling the second end of the suture loop for sliding the slip knot and the first tissue anchor toward the second tissue anchor for reducing the distance between the first and second tissue anchors and applying tension to the first and second tissue layers.

In one embodiment, the first tissue anchor may be parallel to the length of the suture loop when being pulled through the pathway formed in the first and second tissue layers. In one embodiment, the first and second tissue anchors may be perpendicular to the length of the suture loop when applying tension to the first and second tissue layers.

In one embodiment, a suture implant for approximating tissue without tying knots, such as an interrupted suture implant, preferably includes a suture having a first end including a fixed knot, a second end, and a slip knot located between the first and second ends that defines a large suture loop having a length. In one embodiment, the slip knot defines a dynamic end of the large suture loop that is located opposite a closed end of the large suture loop.

In one embodiment, the suture implant preferably includes a tissue anchor is coupled with the first end of the suture.

In one embodiment, the large suture loop has a length, whereby pulling the second end of the suture away from the slip knot slides the slip knot and the tissue anchor toward the closed end of the large suture loop and reducing the length of the large suture loop.

In one embodiment, the suture implant preferably includes a needle having a leading end and a trailing end and a small suture loop that is secured to the trailing end of the needle. In one embodiment, the small suture loop is preferably coupled and/or interconnected with the closed end of the large suture loop.

In one embodiment, the first tissue anchor preferably includes a cylindrical body having a leading end and a trailing end, an elongated channel extending from the leading end to the trailing end of the cylindrical body, a laterally extending channel that intersects the elongated channel, and an elongated opening formed in an underside of the cylindrical body that extends from the trailing end of the cylindrical body and the laterally extending channel.

In one embodiment, the first end of the suture passes through the elongated channel of the cylindrical body of the first tissue anchor, and the fixed knot secures the first tissue anchor at the first end of the suture. In one embodiment, the fixed knot may be located at the leading end of the cylindrical body of the first tissue anchor. In another embodiment, the fixed knot may be located at the trailing end of the body of a tissue anchor.

In one embodiment, the slip knot may be at least partially seated within the elongated opening formed in the underside of the cylindrical body of the first tissue anchor.

In one embodiment, the suture implant may include a catch pledget that is secured to the slip knot. In one embodiment, the catch pledget may be configured to slide with the slip knot toward the closed end of the suture loop.

In one embodiment, the slip knot may include two or more slip knot loops. In one embodiment, at least one of the two or more slip knot loops passes through an opening in the catch pledget for securing the catch pledget to the slip knot.

In one embodiment, the catch pledget may include a cylindrical-shaped body, and two or more hooks projecting from the cylindrical-shaped body. The hooks are adapted to catch onto a suture loop during a suturing procedure.

In one embodiment, a method of using a suture implant for approximating tissue without tying knots preferably includes passing the leading end of the needle through first and second tissue layers to form a pathway through the first and second tissue layers, and after forming the pathway; using the needle and the small suture loop for pulling the closed end of the large suture loop through the pathway formed in the first and second tissue layers.

In one embodiment, the method may include after the pulling step, cutting the small suture loop for detaching the needle and the small suture loop from the large suture loop, and pulling the second end of the suture and the tissue anchor through the large suture loop while catching the catch pledget on the outside of the large suture loop.

In one embodiment, the method may include after catching the catch pledget on the outside of the large suture loop, continue pulling on the second end of the suture to move the slip knot, the tissue anchor and the catch pledget toward the closed end of the large suture loop for applying tension to the first and second tissue layers.

In one embodiment, the method may also include pulling the second end of the suture in a lateral direction for toggling the tissue anchor and the catch pledget so that the tissue anchor and the catch pledget are perpendicular to the length of the large suture loop.

BRIEF DESCRIPTION OF THE DRAWINGS

FIG. 2A is a perspective view of a top side of the first tissue anchor shown in FIG. 1.

FIG. 2B is a side view of the first tissue anchor shown in FIG. 2A.

FIG. 2C is a perspective view of an underside of the first tissue anchor shown in FIGS. 2A and 2B.

FIG. 10O shows another stage of a method of deploying the suture implant of FIG. 8 for approximating tissue layers, in accordance with one embodiment of the present patent application.

FIG. 13O shows another stage of a method of deploying the suture implant of FIG. 11 for approximating tissue layers, in accordance with one embodiment of the present patent application.

DETAILED DESCRIPTION OF PREFERRED EMBODIMENTS

Figure 1:
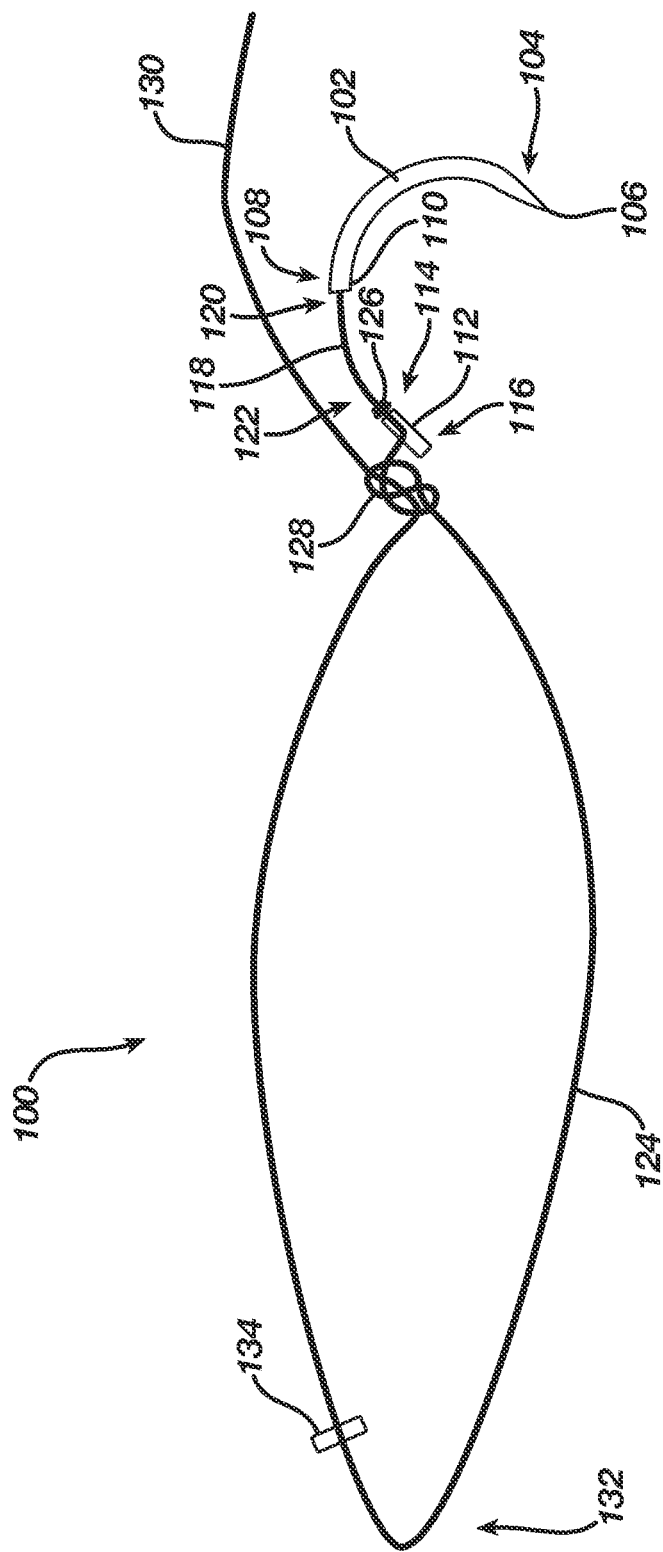
FIG. 1 is a schematic view of a suture implant used for approximating tissue including a needle, a suture loop, a slip knot, a fixed knot, a sliding suture, a first tissue anchor, and a second tissue anchor, in accordance with one embodiment of the present patent application.

Referring to FIG. 1, in one embodiment, a suture implant 100 used for approximating tissue preferably includes a needle 102 having a leading end 104 with a sharpened point 106 and a trailing end 108 that includes a suture swage attachment 110. In one embodiment, the needle 102 is a suture needle that is adapted for suturing tissue. In one embodiment, the suture needle may be curved.

In one embodiment, the suture implant 100 preferably includes a first tissue anchor 112 having a leading end 114 and a trailing end 116. The suture implant 100 preferably includes a single suture strand 118 having a leading end 120 attached (e.g., swaged) to the suture swage attachment 110 and a trailing end 122 that is secured to the first tissue anchor 112.

In one embodiment, the suture implant 100 preferably includes a suture loop 124 that is coupled with the first tissue anchor 112. The suture loop 124 preferably has a first end that includes a fixed knot 126, a slip knot 128, and a second end including a sliding suture 130. In one embodiment, the second end of the suture loop 124 passes through the first tissue anchor 112 and the fixed knot 126 is located adjacent the leading end 114 of the first tissue anchor 112. As used herein, the term "slip knot" means a knot that is made by tying the end of a suture around the suture itself to form a loop so that the size of the loop may be changed by slipping the knot.

In one embodiment, the suture loop 124 of the suture implant 100 preferably has a closed end 132. In one embodiment, the sliding suture 130 may be pulled for moving the slip knot 128 toward a closed end of the suture loop 124 for reducing the size of the suture loop 124 (e.g., when approximating tissue).

In one embodiment, the suture implant 100 desirably includes a second tissue anchor 134 that is coupled with the suture loop 124. In one embodiment, the second tissue anchor 134 preferably has an opening that extends through a central region thereof and the suture loop 124 desirably passes through the opening of the second tissue anchor. In one embodiment, the second tissue anchor 134 is free to slide and/or toggle relative to the suture loop 124. For example, the second tissue anchor 134 may have a length, and the second tissue anchor may be toggled so that the length of the second tissue anchor extends along an axis that is perpendicular to the length of the suture loop 124 for engaging tissue.

In one embodiment, the suture loop 124 extends between the first tissue anchor 112 and the second tissue anchor 134. The slip knot 128, which is positioned between the first tissue anchor 112 and the second tissue anchor 134, allows the first tissue anchor 112 to slide toward the second tissue anchor 134. In one embodiment, the sliding suture 130 may be pulled away from the slip knot 128 for moving the slip knot toward the closed end 132 of the suture loop 124 to reduce the distance between the first and second tissue anchors 112, 134 and apply tension to tissue via the suture loop 124.

In one embodiment, as the free end of the sliding suture 130 is pulled, the slip knot 128 and the first tissue anchor 112 move toward the second tissue anchor 134 for applying a clamping force between an underside of the first tissue anchor 112 and either side (e.g., the top side or the underside) of the second tissue anchor 134. In one embodiment, the first and second tissue anchors are capable of toggling relative to one another so that major surfaces of the first tissue anchor 112 and the second tissue anchor 134 oppose major surfaces of tissue (e.g., parallel tissue layers) that is located between the two tissue anchors.

In one embodiment, the first and second tissue anchors 112, 134 may be made of absorbable and/or non-absorbable materials. Preferred absorbable materials may include PDS, PDS/lactide-glycolide blends, PLA, etc. In one embodiment, the first and second tissue anchors may be fabricated by molding, however, with small modifications, other processes such as casting, stamping, and machining may be used. In one embodiment, the tissue anchors may be extruded into a general shape, and then formed. In one embodiment, the tissue anchors may be printed using a three-dimensional (3-D) printer.

In one embodiment the single suture strand 118, and the suture loop 124 including the fixed knot 126, the slip knot 128, and the sliding suture 130 may be made of conventional, biocompatible, absorbable materials, non-absorbable materials, and combinations of absorbable and non-absorbable materials. Preferred non-absorbable materials include polypropylene, a polymer blend of polyvinylidene fluoride and polyvinylidene fluoride-co-hexafluoropropylene, polyethylene, polyvinylidene fluoride (PVDF), polyesters, polyethylene terephthalate, glycol-modified polyethylene terephthalate, polytetrafluoroethylene, fluoropolymers, nylons etc. and the like, or copolymers of combinations thereof. Preferred absorbable polymeric materials include polydioxanone, polyglactin, polyglycolic acid, copolymers of glycolide and lactide, polyoxaesters, and poliglecaprone. In certain preferred embodiments, the suture loop 124 may include combinations of both absorbable and non-absorbable materials. In addition, metals or ceramics may be suitable for certain applications, such as instances where specific strength or corrosion resistance is necessary. In one preferred embodiment, the suture material preferably includes a polymer blend of polyvinylidene fluoride and polyvinylidene fluoride-co-hexafluoropropylene material. In addition, any of these materials may have conventional surface modifications that include coatings, plasma treatments, therapeutics, and the like. In one embodiment, the single suture strand 118, and the suture loop 124 including the fixed knot 126, the slip knot 128, and the sliding suture 130 may be a polypropylene suture sold under the trademark PROLENE® by Ethicon, Inc of Somerville, N.J.

Referring to FIGS. 2A-2C, in one embodiment, the first sue anchor 112 preferably includes the leading end 114 and the trailing end 116. In one embodiment, the first tissue anchor 112 preferably includes a body having a tubular or cylindrical shape. In one embodiment, the leading and trailing ends 114, 116 of the first tissue anchor 112 may be tapered for facilitating passage of the first tissue anchor through tissue.

In one embodiment, the tissue anchor 112 may have a larger cross-section than the needle 102 (FIG. 1), however, the tapered leading end 114 of the tissue anchor preferably enables the larger cross-section tissue anchor (i.e., compared to the cross-section of the needle) to pass through a pathway in tissue that has been pre-formed by the needle.

In one embodiment, the first tissue anchor 112 preferably has a longitudinal axis $A_1$ (FIG. 2B) that extends along the length $L_1$ thereof. The first tissue anchor 112 desirably has an elongated channel 136 that extends along the length $L_1$ of the first tissue anchor and between the leading and trailing ends 114, 116 of the first tissue anchor. In one embodiment, the first tissue anchor 112 preferably includes a laterally extending channel 138 that extends along a second axis $A_2$ that traverses (e.g., is perpendicular to) the first axis $A_1$ of the elongated channel 136.

In one embodiment, the first tissue anchor 112 preferably includes an elongated opening 140 that is formed at an underside of the tube-shaped body of the first tissue anchor. The elongated opening 140 is preferably in communication with a proximal segment of the elongated channel 136. In one embodiment, a distal end of the elongated opening 140 is aligned with the laterally extending channel 138 that extends along the second axis $A_2$ that traverses the first axis $A_1$. The elongated opening 140 desirably provides a space or recess that is adapted to receive at least a portion of the slip knot 128 of the suture loop 124 (FIG. 1), which may be at least partially seated within the elongated opening 140.

Figure 3:
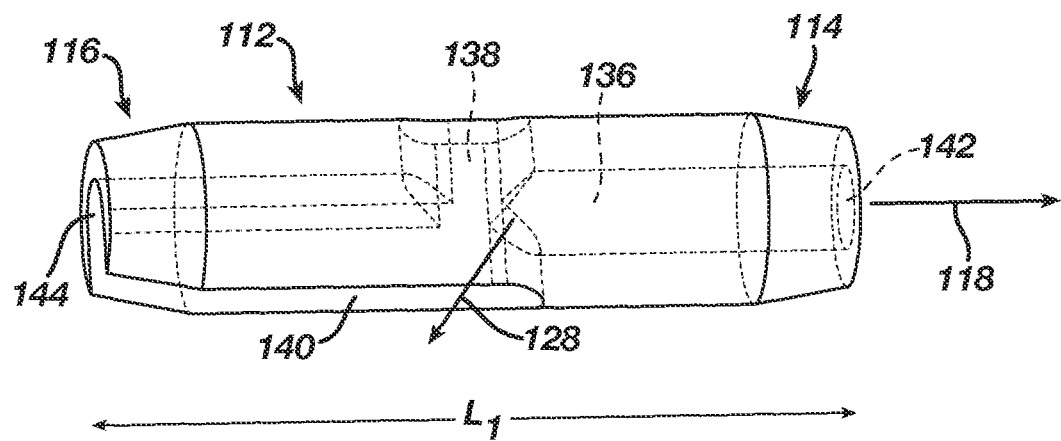
FIG. 3 is a side transparent view of the first tissue anchor shown in FIGS. 1 and 2A-20.

Referring to FIG. 3, in one embodiment, the elongated channel 136 preferably extends along the length $L_1$ of the first tissue anchor 112. The distal end of the elongated channel 136 preferably defines a distal opening 142 that is configured to accommodate the fixed knot 126 connected to the single suture strand 118 that, in turn, is connected to the trailing end of the needle 102 (FIG. 1). The elongated opening 140 at the underside of the body of the first tissue anchor 112 is configured to seat at least a portion of the slip knot 128 (FIG. 1) of the suture loop so that the slip knot may be at least partially hidden within the body of the first tissue anchor.

In one embodiment, resistance as the first tissue anchor 112 is pulled through tissue may be minimized by optimizing the tissue anchor's profile and dimensions at the leading end 114 thereof. In one embodiment, the cross-sectional outer dimension of the first tissue anchor 112 is preferably less than or equal to the cross-sectional dimension of the needle 102 (FIG. 1) for minimizing tissue resistance. In one embodiment, the cross-sectional dimensions of the fixed knot 126 can be minimized by reducing the number of throws in the knot to further reduce tissue resistance. In one embodiment, because the single suture strand 118 is desirably in-line with the longitudinal axis $A_1$ of the first anchor 112, the first tissue anchor may be readily pulled through the tissue by following the path created by the needle 102. Since the back end of the suture material exits the first tissue anchor 112 at a direction that is nearly perpendicular to the longitudinal axis $A_1$, the first tissue anchor 112 will not get pulled back through the tissue (e.g., in a reverse direction) when tension is applied by pulling the sliding suture 130 (FIG. 1). In one embodiment, the elongated opening 140 at the underside of the body of the first tissue anchor may accommodate the slip knot 128 (FIG. 1) to at least partially hide the slip knot to further reduce tissue resistance as the first tissue anchor 112 is pulled through tissue.

Figure 4:
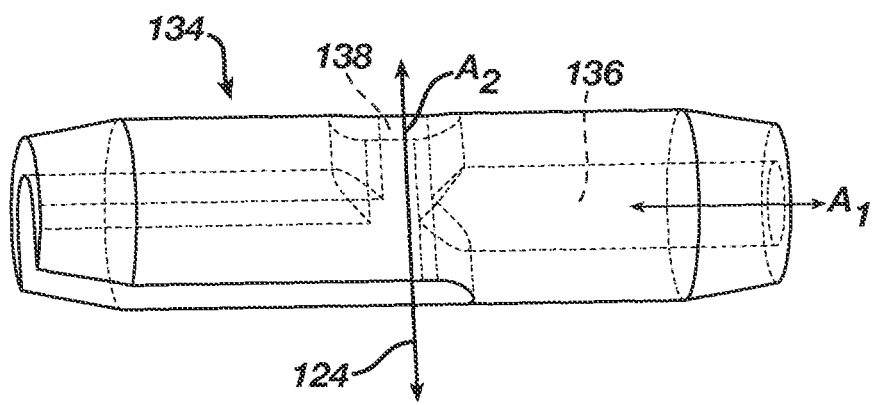
FIG. 4 is a side transparent view of the second first tissue anchor shown in FIG. 1.

Referring to FIG. 4, in one embodiment, in order to enhance economy and/or reduce the number of components that are required for a suture implant, in one embodiment, the second tissue anchor 134 may have the same shape, size, and/or configuration of the first tissue anchor 112 (FIG. 1). When used as the second tissue anchor 134, the suture loop 124 preferably extends through the laterally extending channel 138 of the second tissue anchor 134 along a second axis $A_2$ that is perpendicular to the first axis $A_1$ of the elongated channel 136. The suture loop 124 preferably extends in a perpendicular direction through the second tissue anchor 134 (i.e., along the axis $A_2$) so that the second tissue anchor 134 may toggle into an orientation that maximizes resistance to hold against the tissue. In one embodiment, the long axis $A_1$ of the second tissue anchor 134 is preferably oriented so that it is parallel to a plane of tissue for maximizing the area of contact between a major surface of the second tissue anchor and the tissue plane.

In one embodiment, the suture implant 100 shown and described above in FIGS. 1-4 may be used for suturing tissue such as being used for interrupted suture fixation to approximate tissue. In one embodiment, the suture implant 100 may be used for approximating two parallel or opposing tissue planes.

Figure 5A:
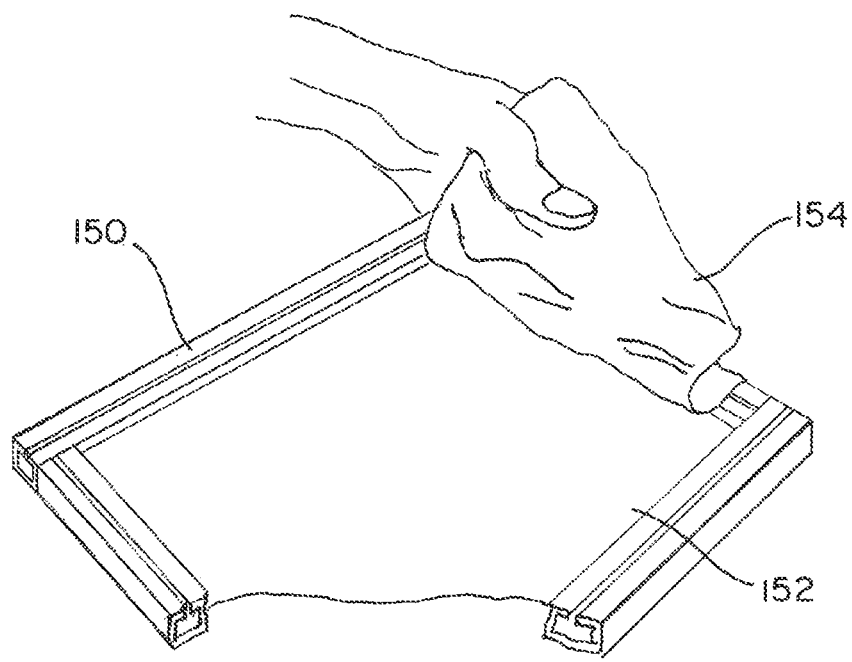
FIG. 5A shows a first stage of a method of deploying a suture implant for approximating tissue layers, in accordance with one embodiment of the present patent application.

FIGS. 5A-5O illustrate methods of using the suture implant 100 shown and described above in FIGS. 1-4 for approximating two tissue planes.

Referring to FIG. 5A, a simulated fixture 150 holds first and second tissue planes 152 and 154. The second tissue plane 154 may be a flap of tissue that has been cut away from the first tissue plane 152. In one embodiment, a method of approximating the two tissue planes 152, 154 preferably includes grabbing the elevated second tissue plane 154 (e.g., a flap of tissue) with the non-dominant hand.

Figure 5B:
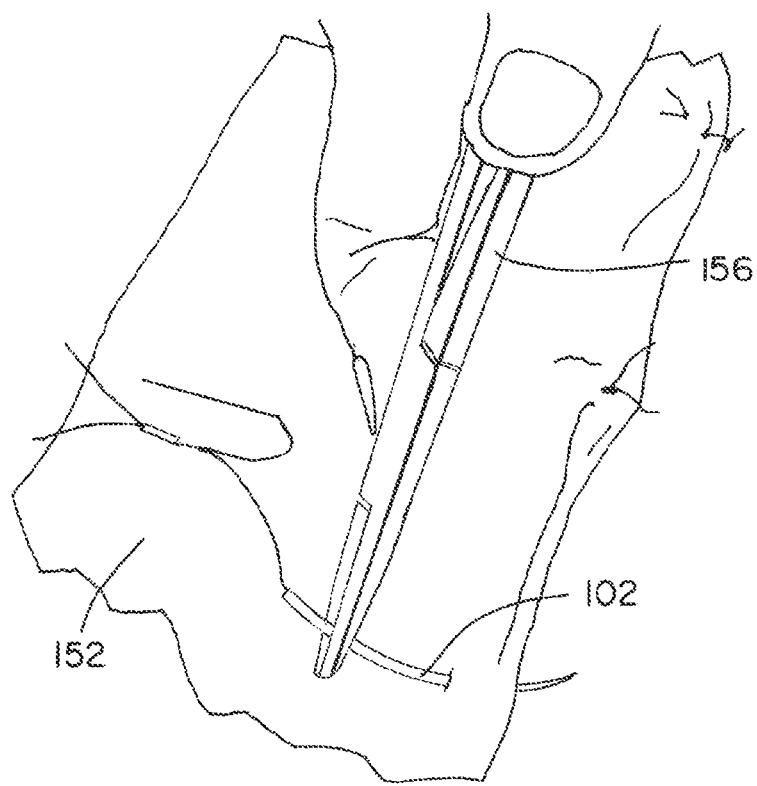
FIG. 5B shows another stage of a method of deploying a suture implant for approximating tissue layers, in accordance with one embodiment of the present patent application.
Figure 5C:
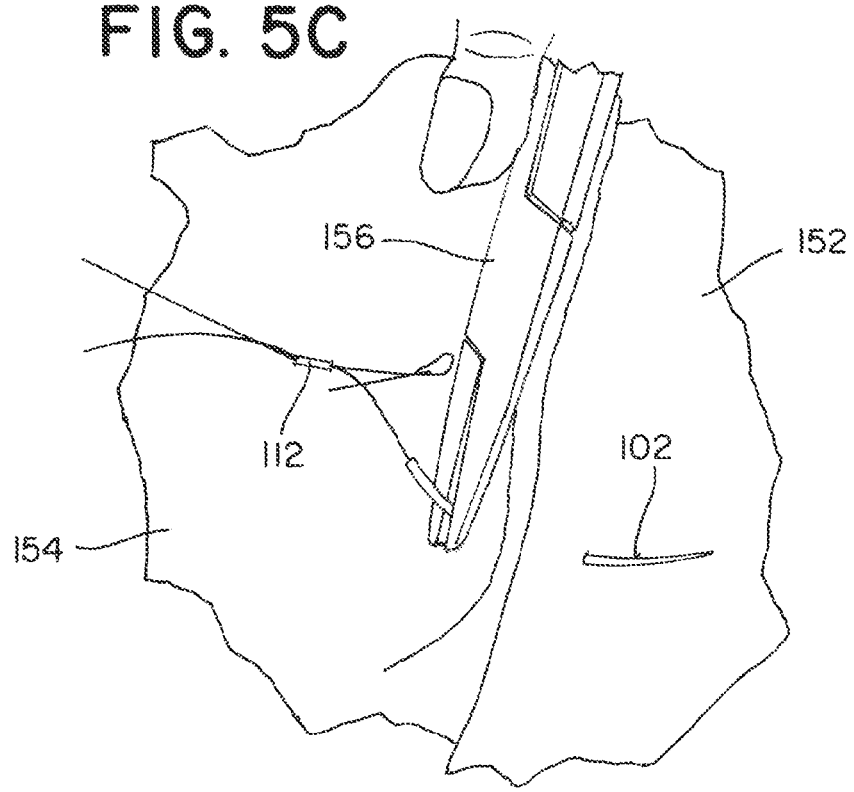
FIG. 5 shows another stage of a method of deploying a suture implant for approximating tissue layers, in accordance with one embodiment of the present patent application.
FIG. 5D shows another stage of a method of deploying a suture implant for approximating tissue layers, in accordance with one embodiment of the present patent application.
FIG. 5E shows another stage of a method of deploying a suture implant for approximating tissue layers, in accordance with one embodiment of the present patent application.
FIG. 5F shows another stage of a method of deploying a suture implant for approximating tissue layers, in accordance with one embodiment of the present patent application.
FIG. 5G shows another stage of a method of deploying a suture implant for approximating tissue layers, in accordance with one embodiment of the present patent application.
FIG. 5H shows another stage of a method of deploying a suture implant for approximating tissue layers, in accordance with one embodiment of the present patent application.
FIG. 5I shows another stage of a method of deploying a suture implant for approximating tissue layers, in accordance with one embodiment of the present patent application.
FIG. 5J shows another stage of a method of deploying a suture implant for approximating tissue layers, in accordance with one embodiment of the present patent application.
FIG. 5K shows another stage of a method of deploying a suture implant for approximating tissue layers, in accordance with one embodiment of the present patent application.
FIG. 5L shows another stage of a method of deploying a suture implant for approximating tissue layers, in accordance with one embodiment of the present patent application.
FIG. 5M shows another stage of a method of deploying a suture implant for approximating tissue layers, in accordance with one embodiment of the present patent application.
FIG. 5N shows another stage of a method of deploying a suture implant for approximating tissue layers, in accordance with one embodiment of the present patent application.
FIG. 5O shows another stage of a method of deploying a suture implant for approximating tissue layers, in accordance with one embodiment of the present patent application.

Referring to FIGS. 5B and 5C, in one embodiment, a needle holder 156 is used to pass the needle 102 through both tissue planes 152, 154.

Figure 5D:
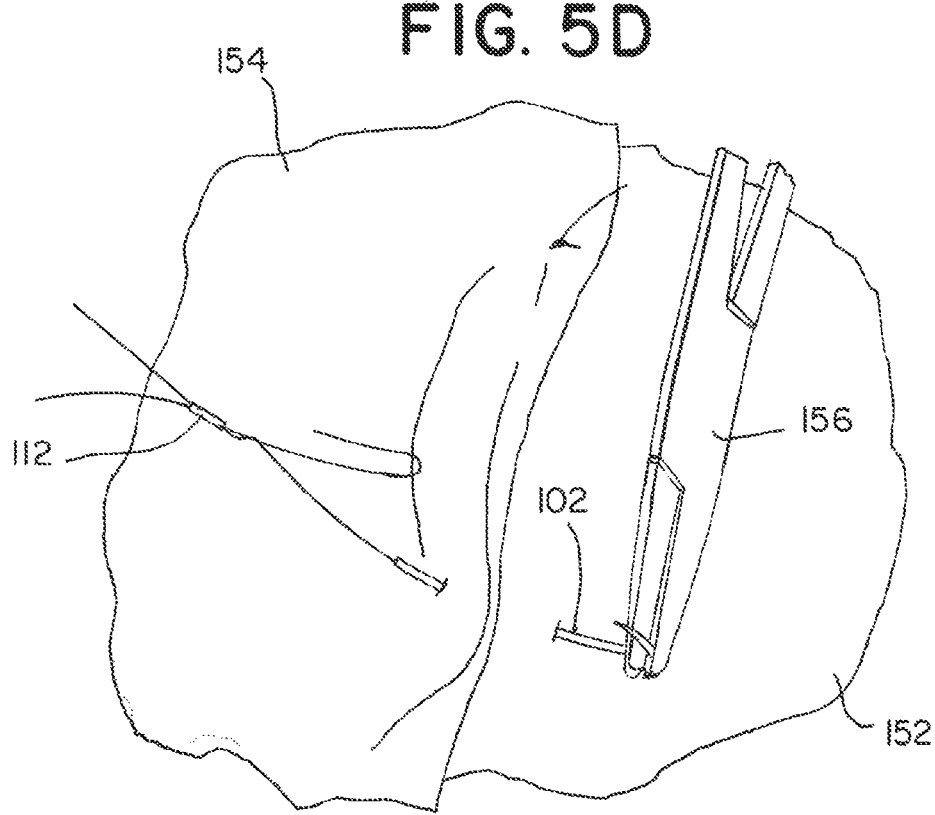
Figure 5E:
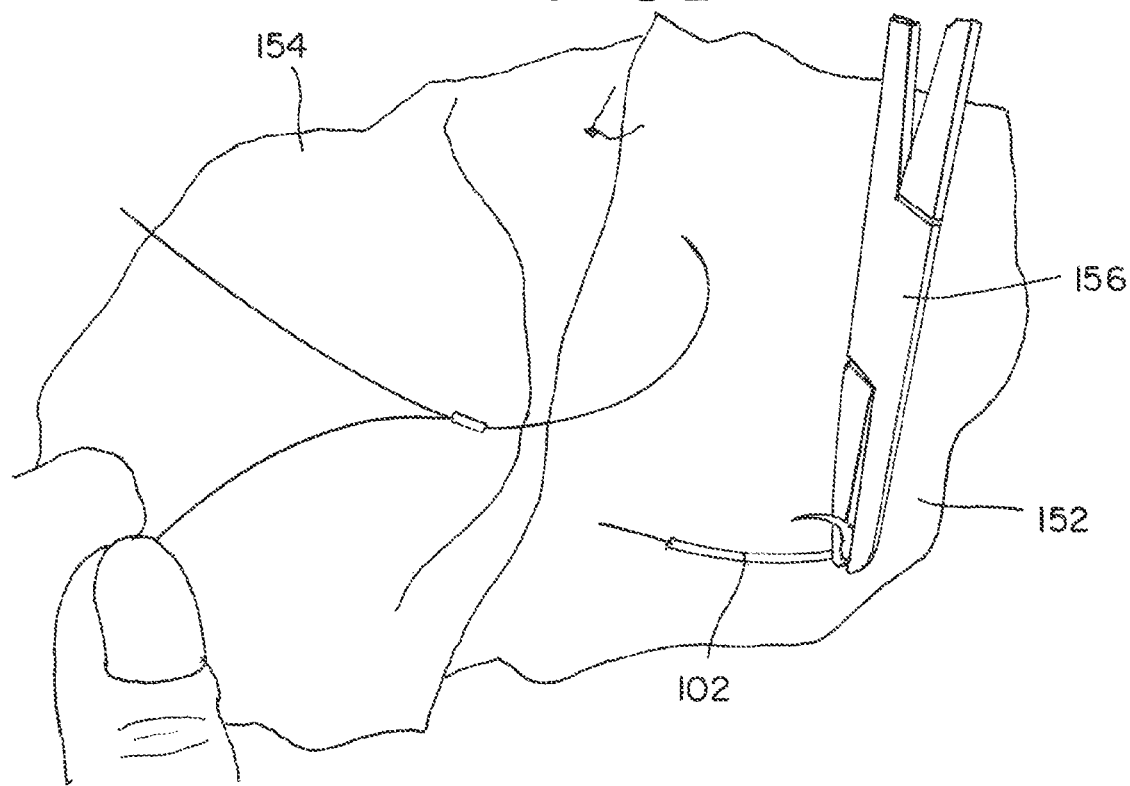
Figure 5F:
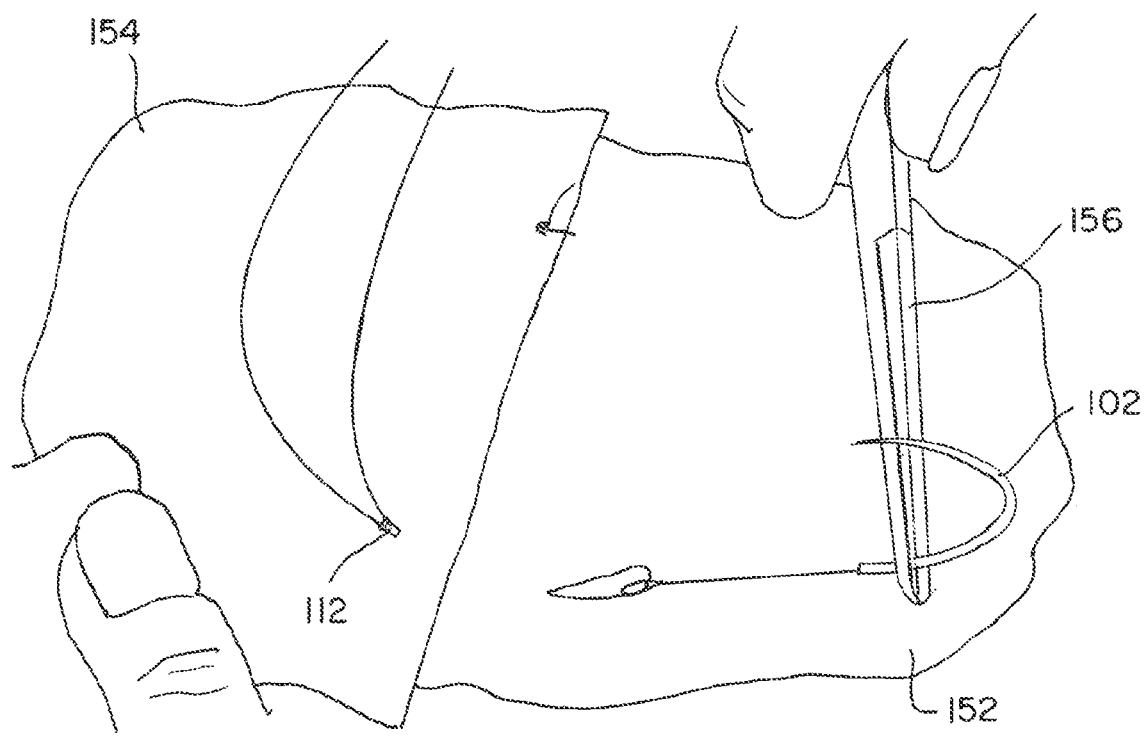

Referring to FIGS. 5D-5F, in one embodiment, the needle holder 156 is used to pull the needle 102, the single suture strand 118, and the first tissue anchor 112 completely through the first and second tissue planes 152, 154. As it is being pulled through the first and second tissue planes 152, 154, the first tissue anchor 112 is preferably in-line with the needle 102 and the single suture strand 118 so that there is minimal drag as the first tissue anchor 112 is pulled through the two tissue planes 152, 154.

Figure 5G:
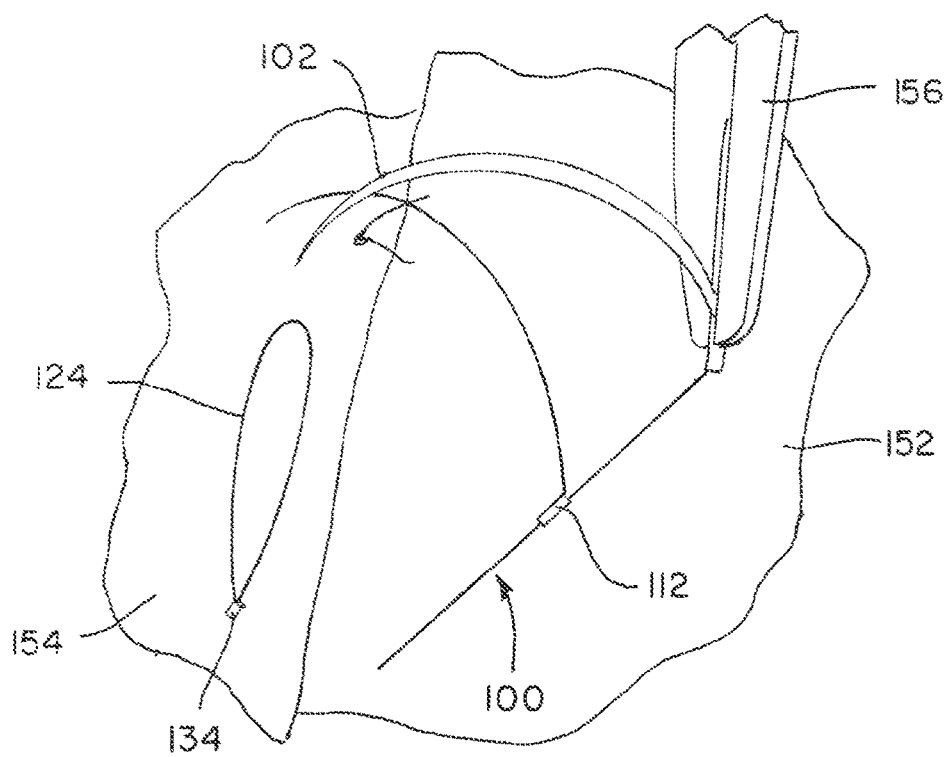
Figure 5H:
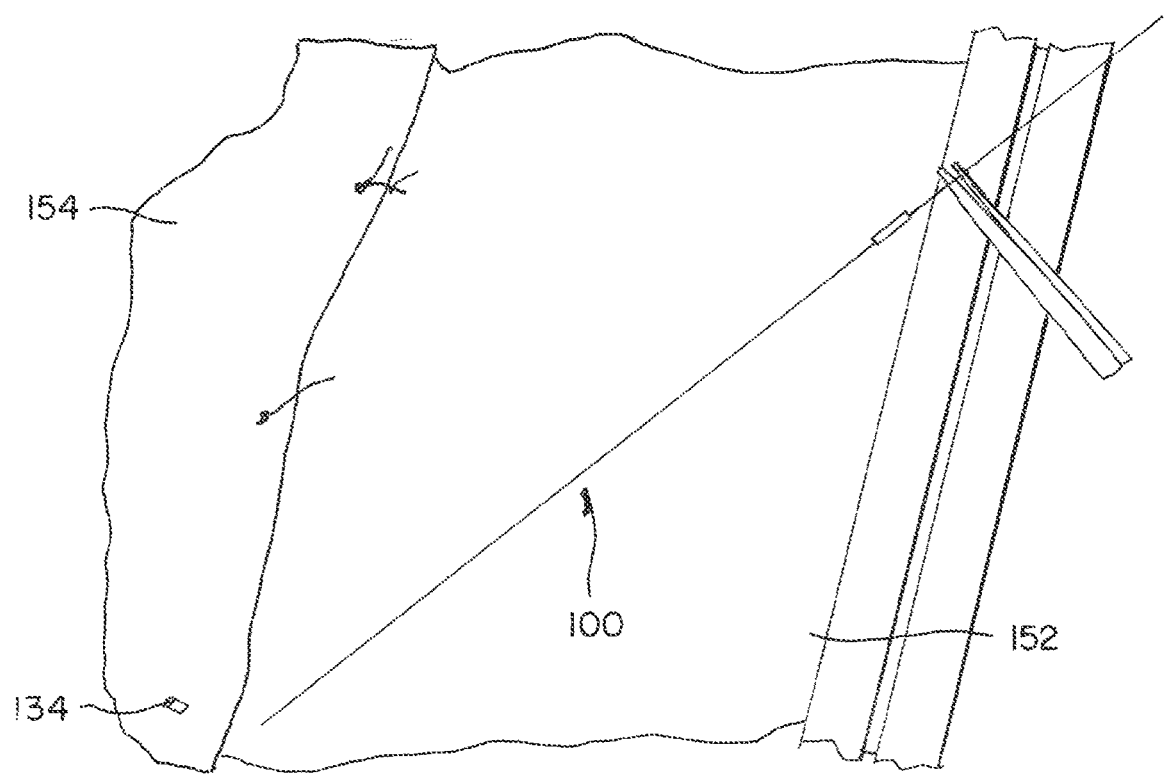

Referring to FIGS. 5G and 5H, after the first tissue anchor 112 has been pulled completely through both tissue planes 152, 154, the needle 102 is further pulled until the second tissue anchor 134 is seated against the second tissue plane 154. In one embodiment, the needle 102 is pulled until all slack has been removed from the single suture strand 118 and the suture loop 124.

Referring to FIG. 5H, in one embodiment, the single suture strand 118 that is swaged to the needle 102 (FIG. 6G) and that extends between the fixed knot 126 distal to the first tissue anchor 112 and the trailing end of the needle 102 is preferably cut to detach the needle 102 from the suture implant 100.

Figure 5I:
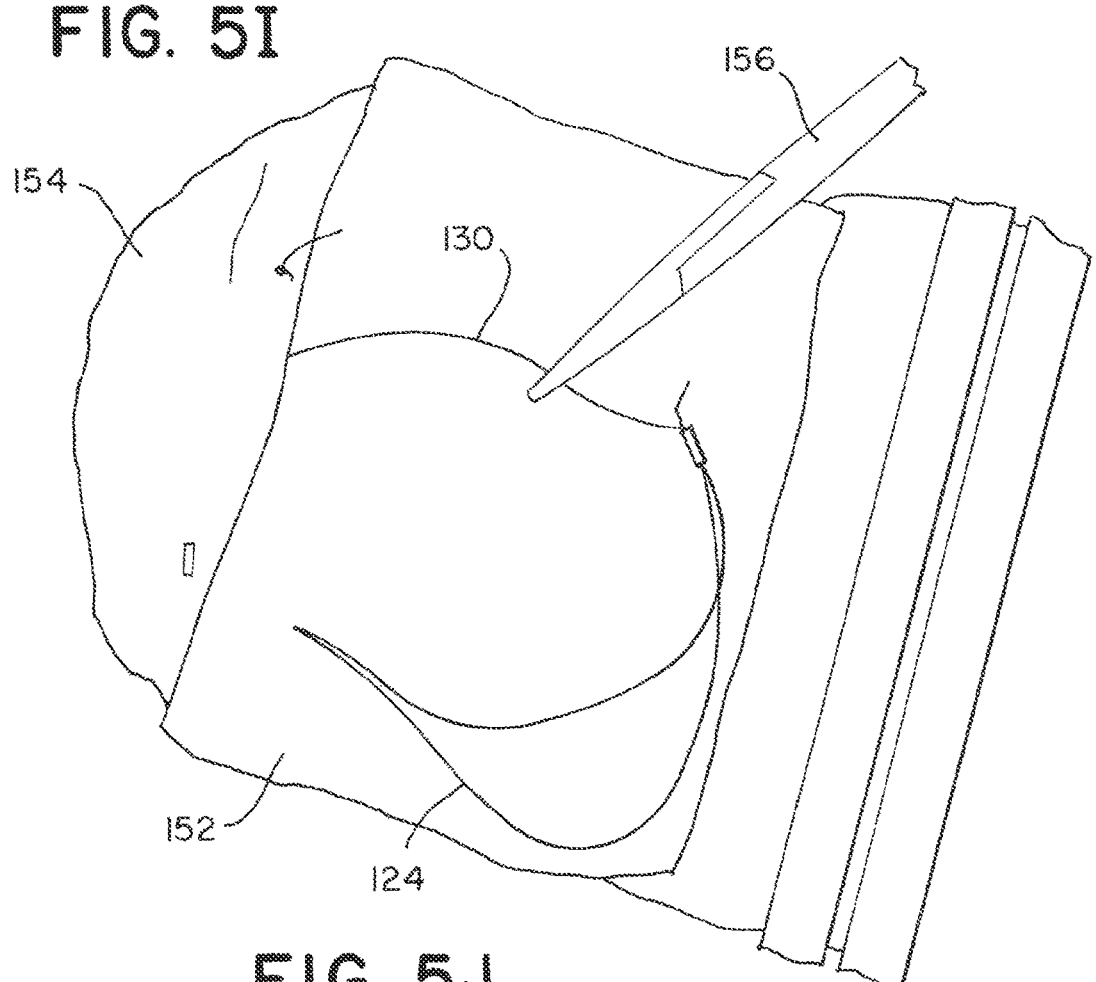

Referring to FIG. 5I, in one embodiment, in order to reduce the size of the suture loop 124, the sliding suture 130 located at the first end of the suture loop 124 may be secured using a gripping component such as a needle holder 156.

Figure 5J:
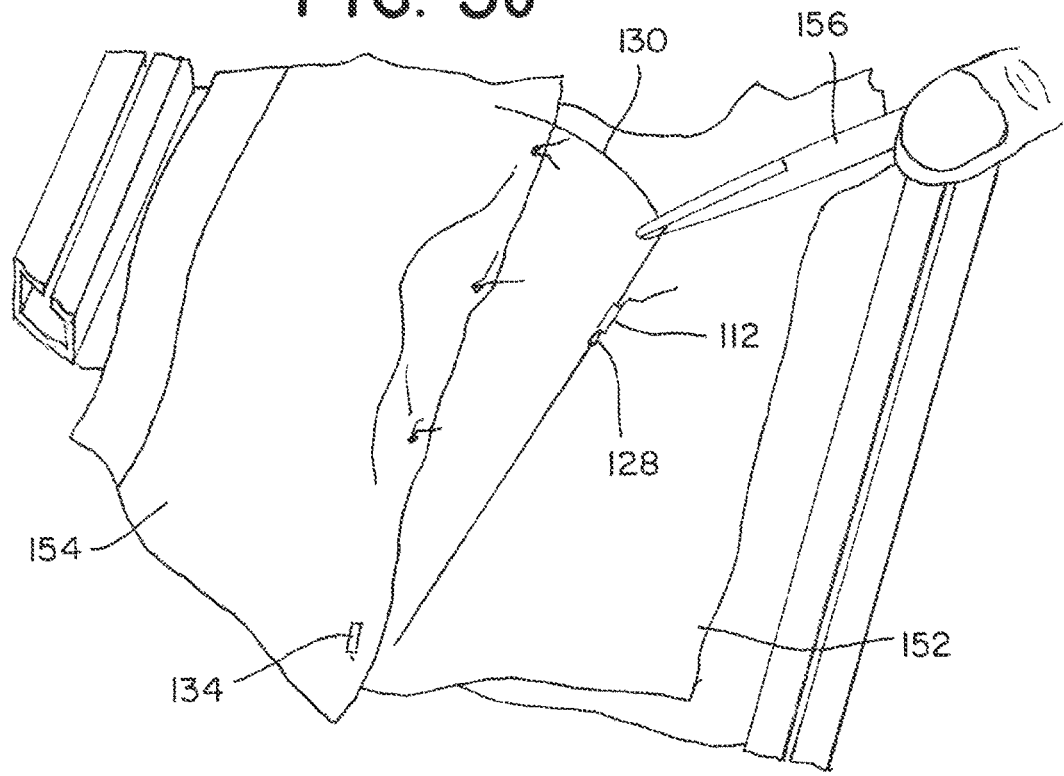
Figure 5K:
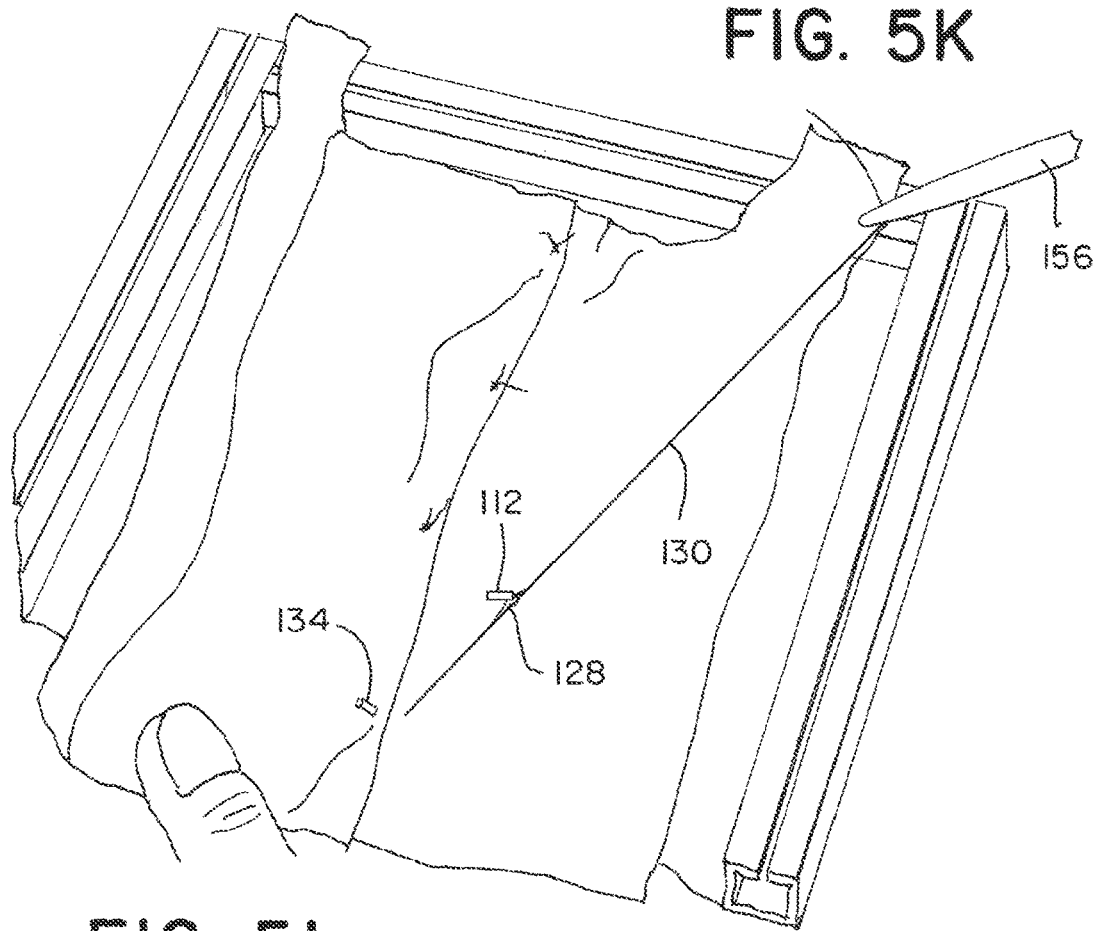
Figure 5L:
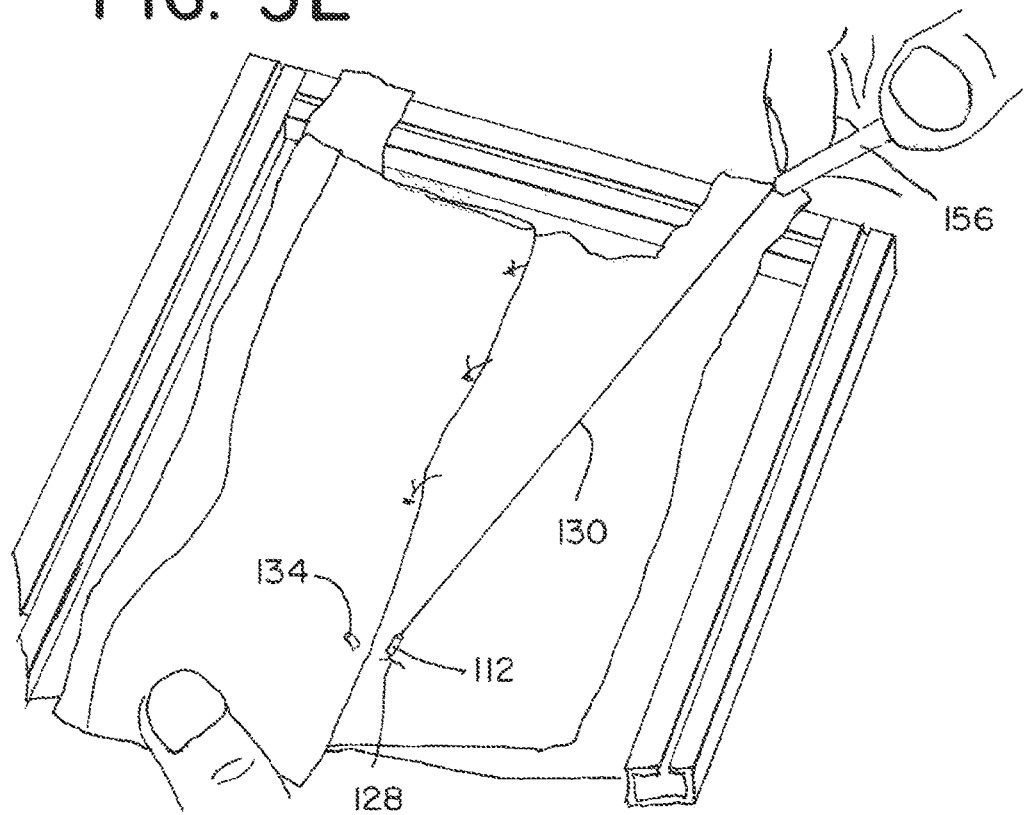

Referring to FIGS. 5J-5L, in one embodiment, the sliding suture 130 may be continuously pulled by the needle holder 156 to move the slip knot 128 toward the closed end 132 of the suture loop 124 for reducing the size of the suture loop 124 for cinching the first tissue anchor 112 downwards toward the second tissue anchor 134.

Figure 5M:
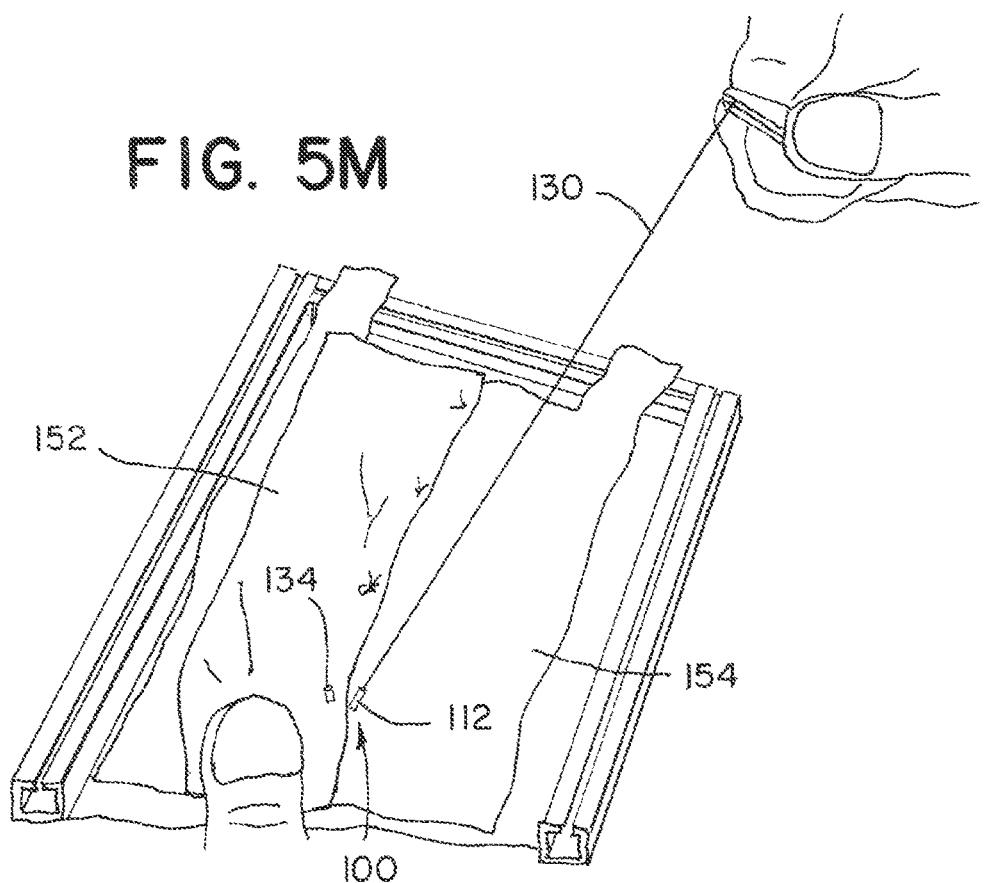

Referring to FIG. 5M, the sliding suture 130 is preferably pulled until a desired level of tension is applied to the first and second tissue planes 152, 154 via the first and second tissue anchors 112, 134 (FIG. 1) of the suture implant 100.

Figure 5N:
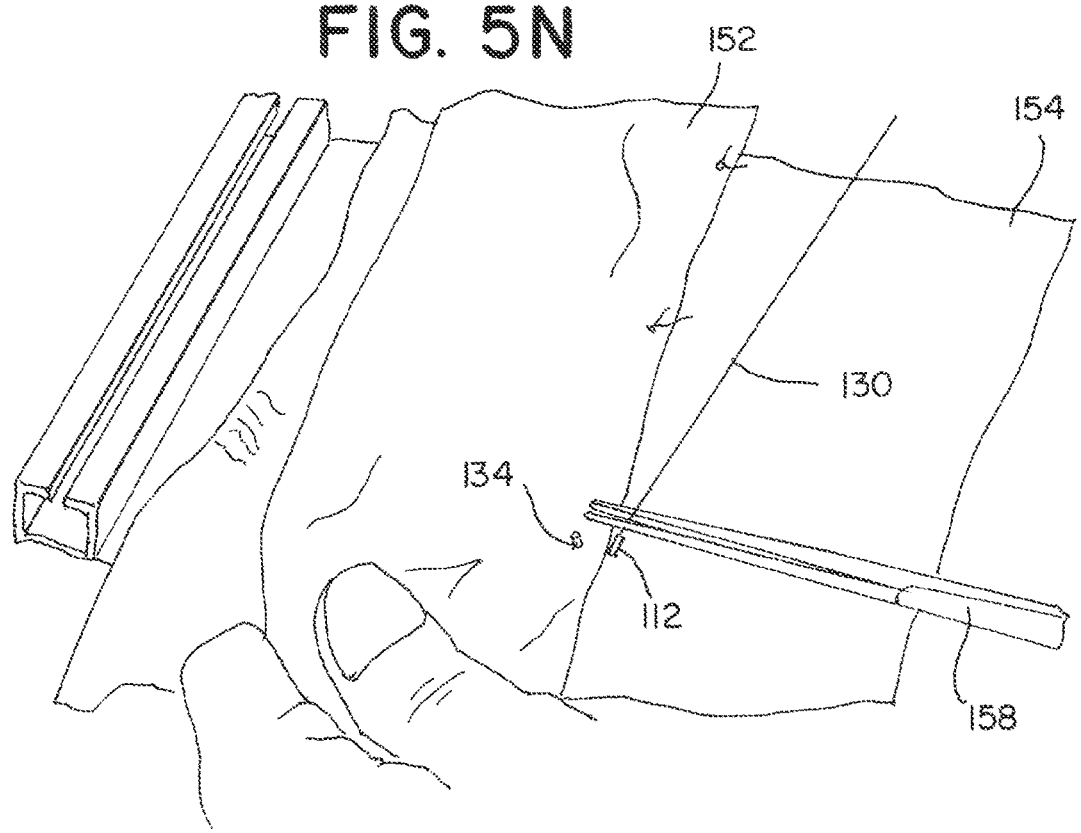
Figure 50:
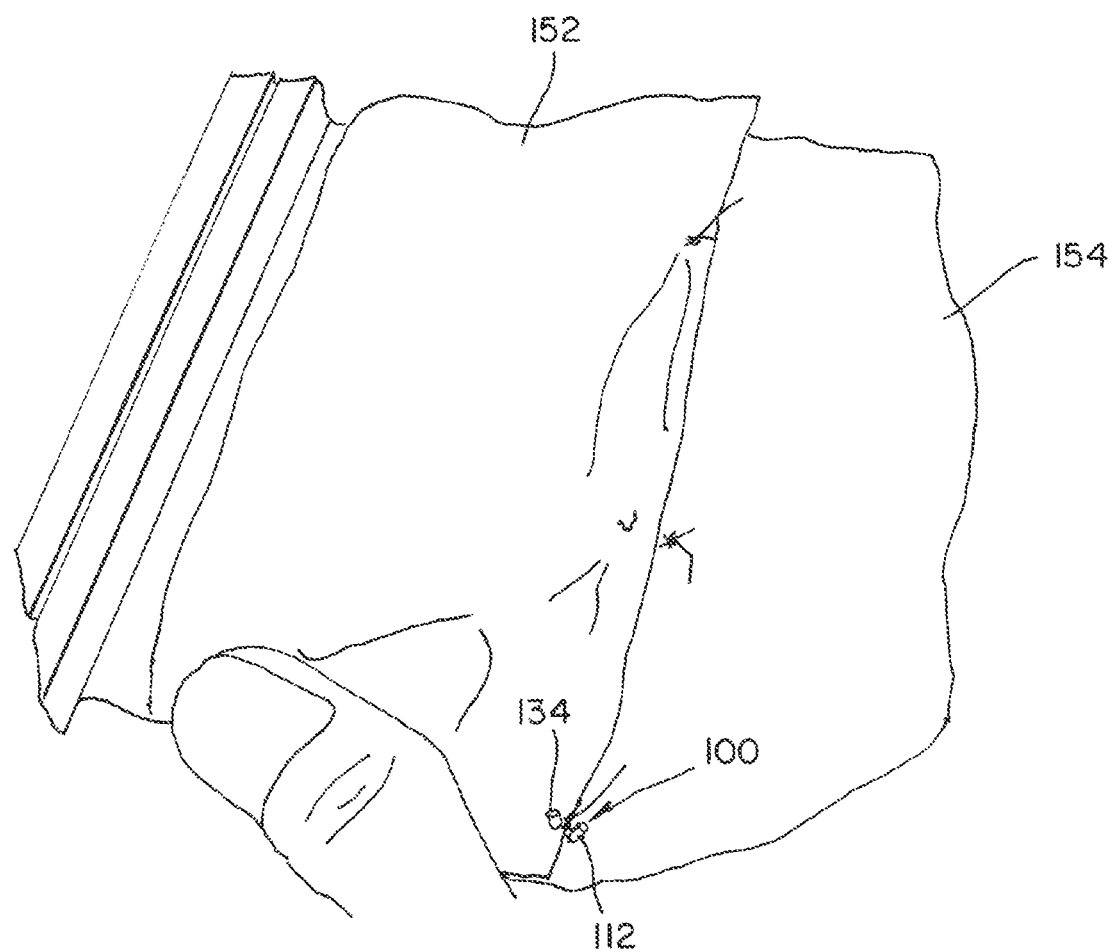

Referring to FIGS. 5N and 5O, after tensioning, any excess suture material that remains, including the sliding suture 130, may be cut and/or trimmed away using a cutting tool 158. FIG. 5O shows the suture implant 100 including the first and second tissue anchors 112, 134 after the excess suture material has been cut away. The first tissue anchor 112 preferably engages the first tissue plane 152 and the second tissue anchor 134 preferably engages the second tissue plane 154.

Figure 6A:
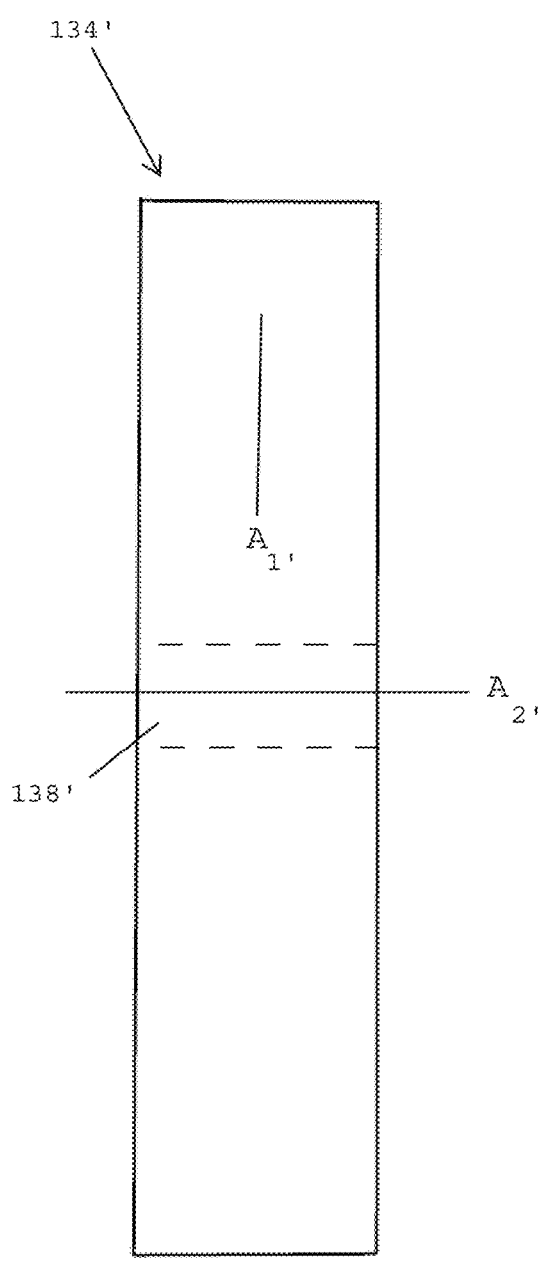
FIG. 6A is a side view of a tissue anchor of a suture implant used for approximating tissue, in accordance with one embodiment of the present patent application.
Figure 6B:
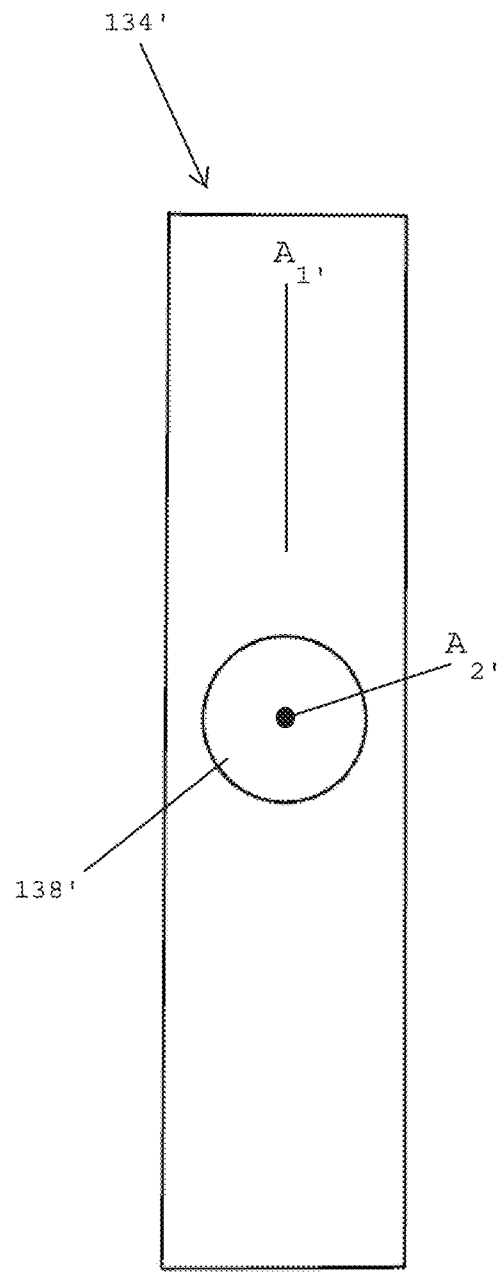
FIG. 6B is a front view of the tissue anchor shown in FIG. 6A.

Referring to FIGS. 6A and 6B, in one embodiment, a second tissue anchor 134' of a suture implant may have a cylindrical shape. The second tissue anchor 134' may have a length that extends along a longitudinally extending axis $A_{1'}$ so that the second tissue anchor is longer than wide. In one embodiment, the second tissue anchor 134' may have a centrally located opening 138' that extends through the second tissue anchor 134' along a laterally extending axis $A_{2'}$ that is perpendicular to the longitudinally extending axis $A_{1'}$. The suture loop 124 (FIG. 1) of the suture implant preferably extends through the centrally located opening 138' (i.e., along the axis $A_{2'}$) so that the second tissue anchor 134' may toggle into an orientation that maximizes resistance for holding against tissue. In one embodiment, the second tissue anchor 134' shown in FIGS. 6A and 6B and described in this paragraph may be used in place of the second tissue anchor 134 of the suture implant 100 shown in FIG. 1.

Figure 7A:
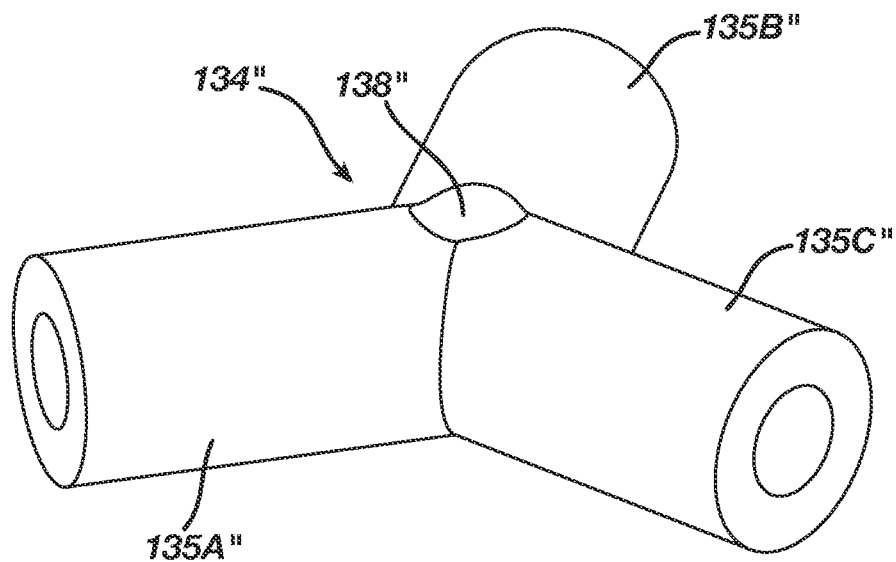
FIG. 7A is a perspective view of a tissue anchor of a suture implant used for approximating tissue, in accordance with one embodiment of the present patent application.
Figure 7B:
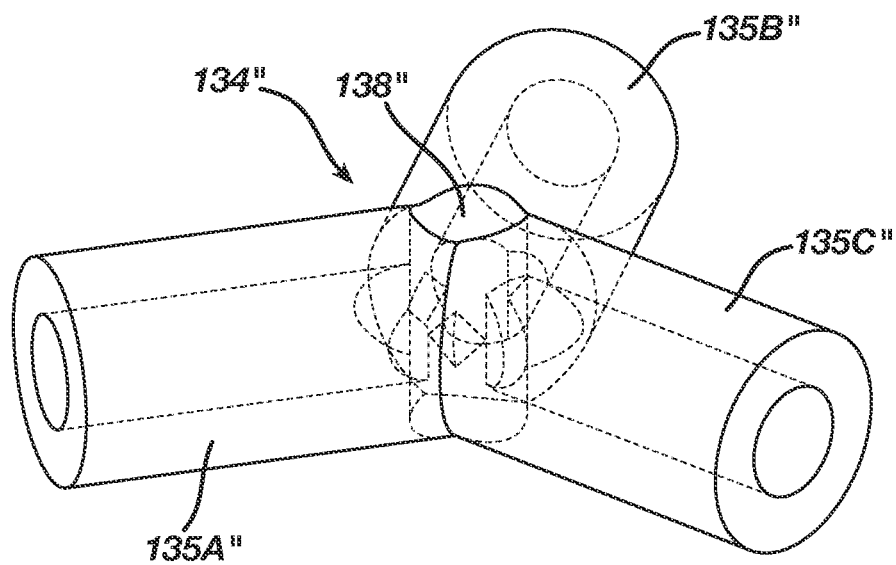
FIG. 7B is a transparent view of the tissue anchor shown in FIG. 7A.

Referring to FIGS. 7A and 7B, in one embodiment, a second tissue anchor 134" of a suture implant may have three or more protrusions 135A"-135C" that extend outwardly from a central opening 138". The central opening 138" preferably extends along an axis that is perpendicular to the longitudinal axes of the respective protrusions 135". The suture loop 124 (FIG. 1) of the suture implant preferably extends through the central opening 138" so that the second tissue anchor 134" is free to toggle into an orientation that maximizes resistance for holding against tissue. In one embodiment, when a suture loop is tightened, the protrusions 135A"-135C" preferably contact a surface of a tissue plane. In one embodiment, the second tissue anchor may have an axisymmetric geometry relative to central opening 138" to maximize the surface area against tissue. In one embodiment, the second tissue anchor 134" shown in FIGS. 7A and 7B and described in this paragraph may be used in place of either the first tissue anchor 112 or the second tissue anchor 134 of the suture implant shown in FIG. 1.

Figure 8A:
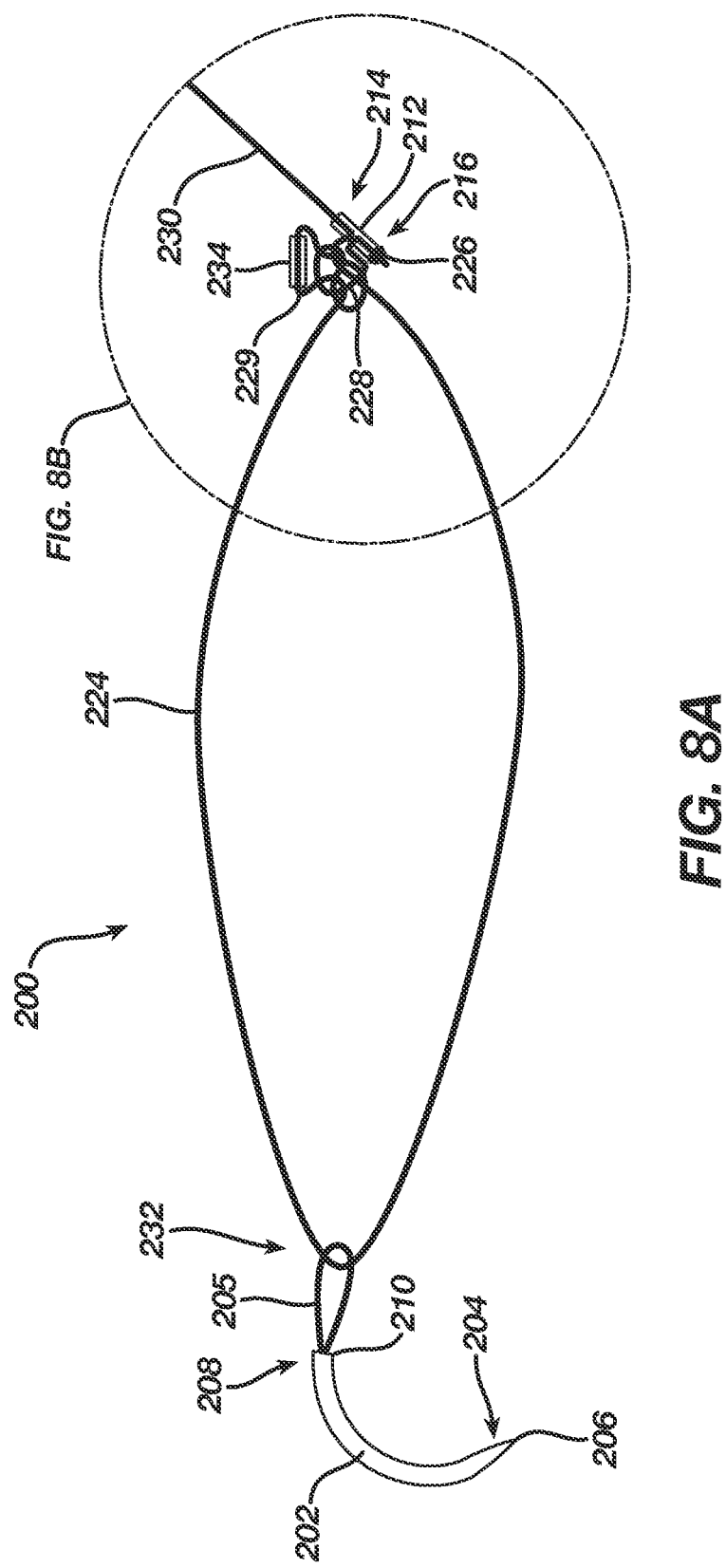
FIG. 8A is a schematic view of a suture implant used for approximating tissue including a needle, a small suture loop attached to the needle, a large suture loop, a slip knot, a fixed knot, a sliding suture, a tissue anchor, and a catch pledget, in accordance with one embodiment of the present patent application.
Figure 8B:
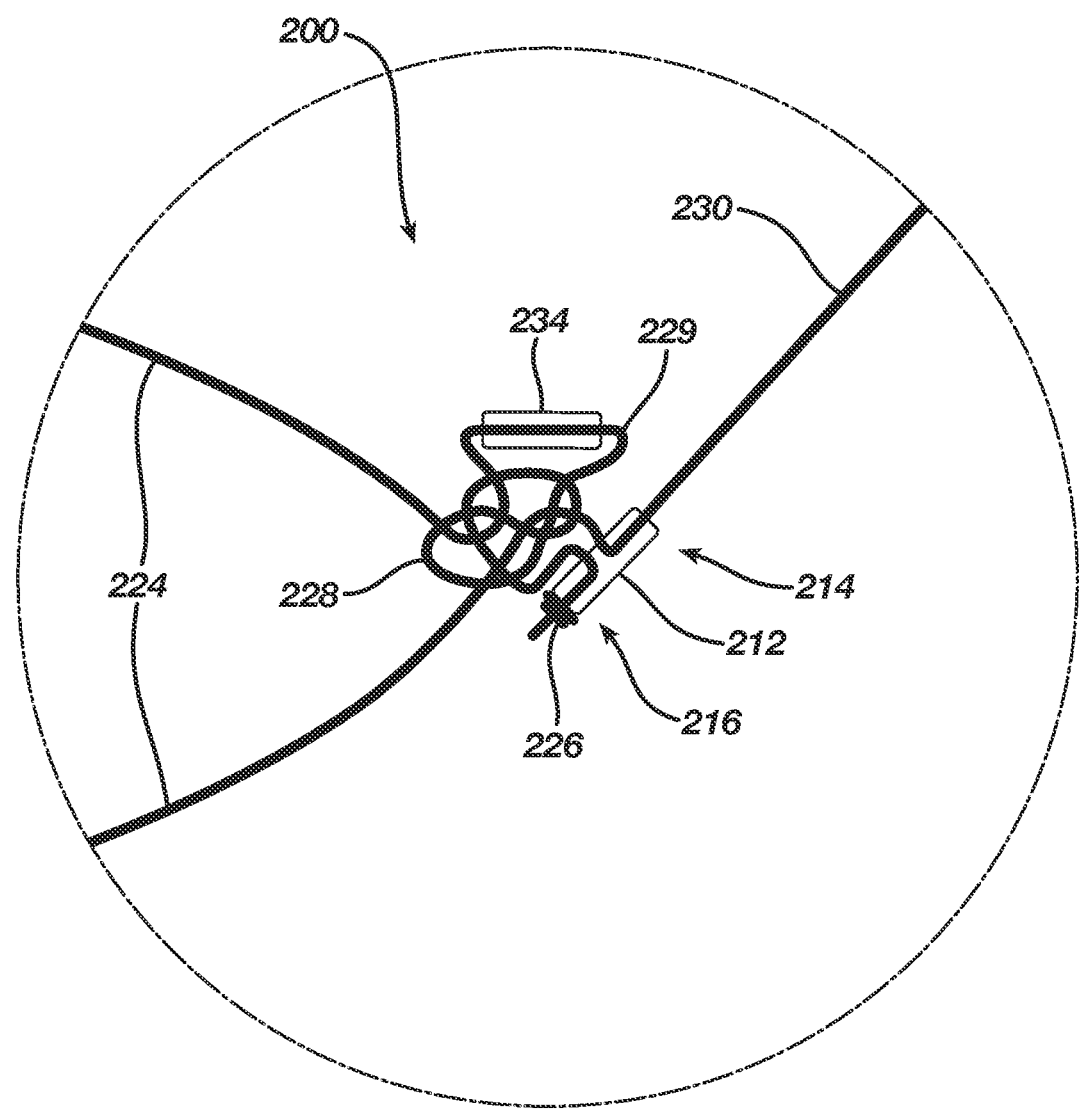
FIG. 8B is a magnified view of a section of the larger suture loop, the slip knot, the fixed knot, the sliding suture, the tissue anchor, and the catch pledget shown in FIG. 8A.

Referring to FIGS. 8A and 8B, in one embodiment, a suture implant 200 may include both a tissue anchor 212 and a catch pledget 234 that is tethered to a slip knot 228. In one embodiment, the suture implant 200 is desirably used for approximating tissue (e.g., approximating two tissue planes) and preferably includes a needle 202 having a leading end 204 with a sharpened point 206 and a trailing end 208 that includes a suture swage attachment 210. In one embodiment, the needle 202 is a suture needle that is adapted for suturing tissue. In one embodiment, the suture needle 202 may be curved.

In one embodiment, the suture implant 200 preferably includes a small suture loop 205 that is attached to the suture swage attachment 210 of the needle 202. In one embodiment, the free ends of the small suture loop 205 are swaged to the suture swage attachment 210 of the needle 202.

In one embodiment, the suture implant 200 preferably includes the tissue anchor 212 having a proximal end 214 and a distal end 216, and the catch pledget 234 that is located adjacent the tissue anchor 212. The suture implant 200 desirably includes a large suture loop 224 having a first end with a fixed knot 226 that is located adjacent the distal end 216 of the tissue anchor 212 and a second end including a sliding suture 230 that extends from a proximal opening at the proximal end 214 of the tissue anchor 212. The large suture loop 224 also desirably includes a slip knot 228 that is adjacent an underside of the tissue anchor 212.

In one embodiment, the large suture loop 224 preferably has a closed end 232 that passes through the opening of the small suture loop 205 so that the small suture loop 205 and the large suture loop 224 are coupled together.

In one embodiment, the slip knot 228 preferably has a slip knot loop 229 that passes through a channel of the catch pledget 234 for securing the catch pledget 234 to the slip knot 228. In one embodiment, as the sliding suture 230 is pulled away from the proximal end 214 of the tissue anchor 212, the slip knot 228 moves toward the closed end 232 of the large suture loop 224 for reducing the size of the large suture loop. As the slip knot 228 moves toward the closed end of the large suture loop 224, the catch pledget 234, which is coupled with the slip knot loop 229 of the slip knot 228, also moves toward the closed end 232 of the large suture loop 224.

Figure 9A:
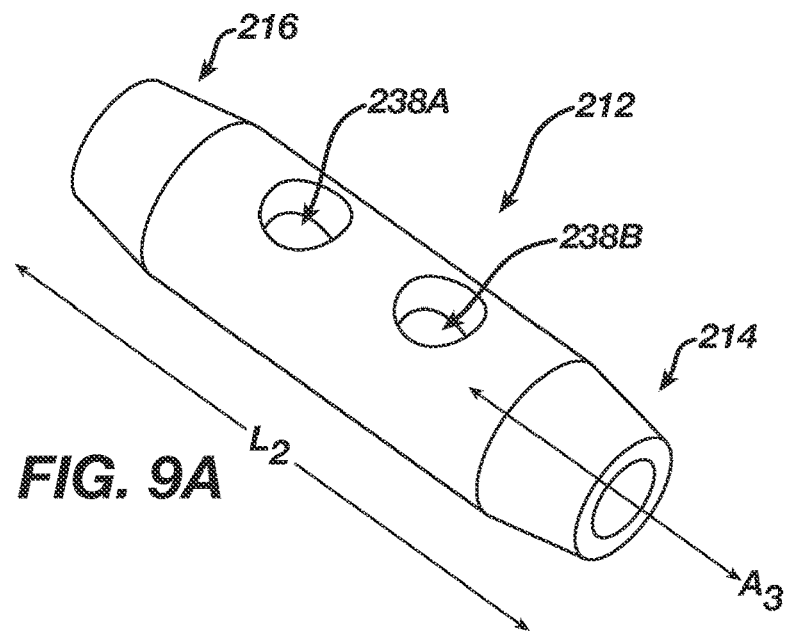
FIG. 9A is a perspective view of the tissue anchor of the suture implant shown in FIG. 8.
Figure 9B:
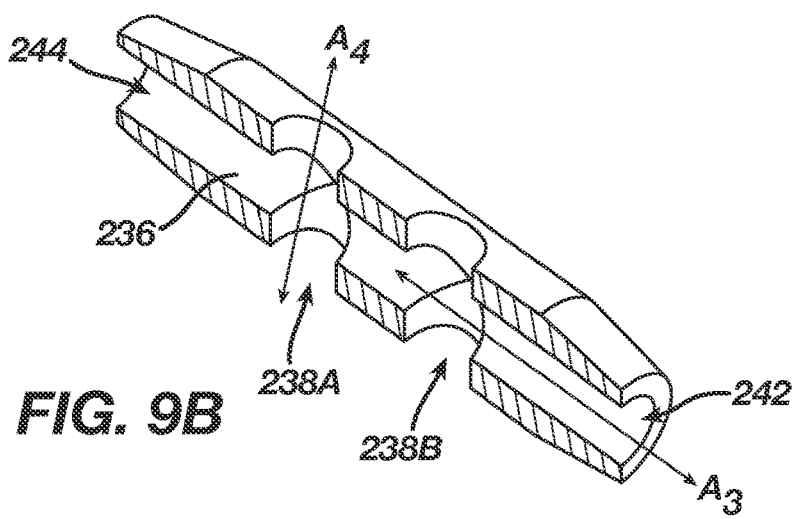
FIG. 9B is a cross-sectional view of the tissue anchor shown in FIG. 9A.
Figure 9C:
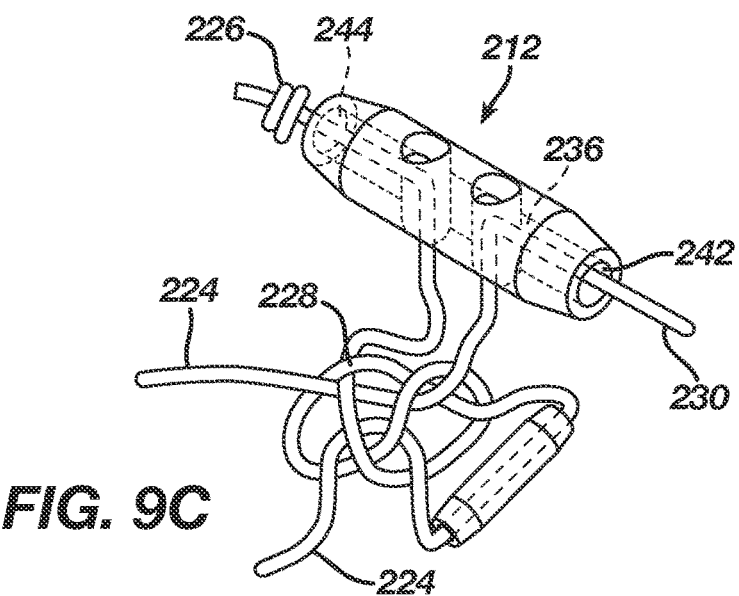
FIG. 9C is a transparent view of the tissue anchor shown in FIGS. 9A and 9B.

Referring to FIGS. 9A-9B, in one embodiment, the tissue anchor 212 of the suture implant 200 (FIG. 1) preferably includes the proximal end 214 and the distal end 216. In one embodiment, the tissue anchor 212 preferably has a tubular or cylindrical shaped body. In one embodiment, the proximal and distal ends 214, 216 of the tissue anchor 212 may be tapered.

In one embodiment, the tissue anchor 212 preferably has a longitudinal axis $A_3$ (FIG. 9B) that extends along the length $L_2$ thereof. The tissue anchor 212 desirably has an elongated channel 236 that extends along the length $L_2$ of the tissue anchor and between the proximal and distal ends 214, 216 of the tissue anchor. In one embodiment, tissue anchor 212 preferably includes a pair of laterally extending channels 238A, 238B that extend along respective second axes $A_4$ that are substantially perpendicular to the longitudinal axis $A_3$ of the tissue anchor 212.

In one embodiment, the elongated channel 236 preferably extends along the length $L_2$ of the tissue anchor 212. The proximal end of the elongated channel 236 preferably defines a proximal opening 242 that is configured to accommodate the sliding suture 230 that is pulled to reduce the size of the large suture loop 224. The distal end of the elongated channel 236 defines a distal opening 244 that is configured to receive the fixed knot 222, which is located at the first end of the large suture loop 224 (FIG. 8). In one embodiment, the slip knot 228 is preferably located below the lower ends of the pair of laterally extending channels 238A, 238B.

In one embodiment, in order to reduce costs and/or enhance efficiency, a component that is similar to the tissue anchor 212 may also be used as the catch pledget 234 of the suture implant (FIG. 8A) with the slip knot loop 229 passing through the elongated channel 236. In one embodiment, the catch pledget 234 is tethered or secured to a loop of the slip knot of the large suture loop 224 and moves with the slip knot.

Figure 10A:
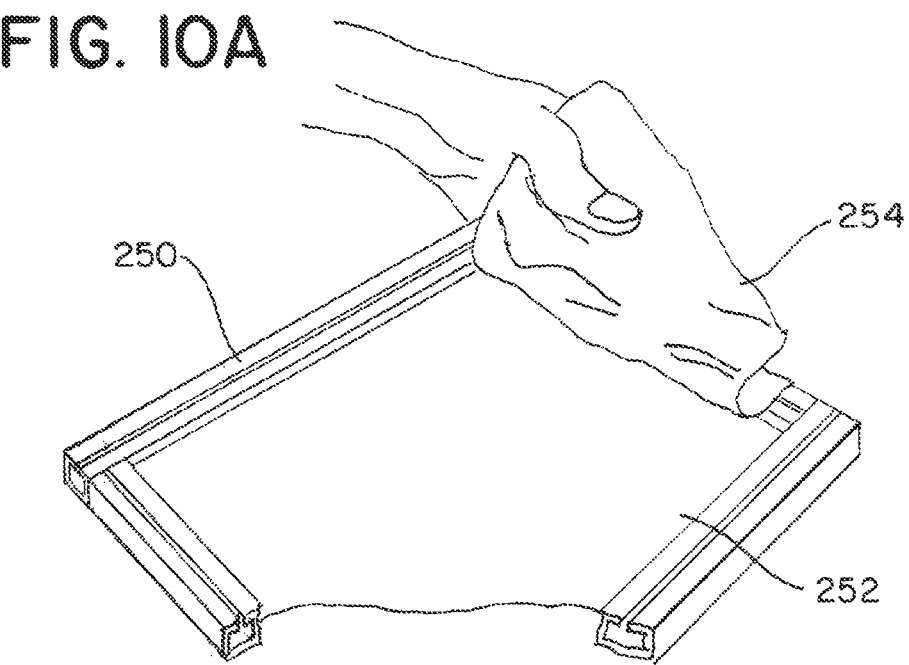
FIG. 10A shows a first stage of a method of deploying the suture implant of FIG. 8 for approximating tissue layers, in accordance with one embodiment of the present patent application.

FIGS. 10A-10O illustrate methods of using the suture implant 200 shown and described above in FIGS. 8A-8B and 9A-9C for approximating tissue, such as approximating two parallel tissue planes. The suture implant 200 may be used for one handed interrupted suture fixation without the need to tie knots.

Referring to FIG. 10A, a simulated fixture 250 holds first and second tissue planes 252 and 254. The second tissue plane 254 may be a flap of tissue that has been cut away from the first tissue plane 252. In one embodiment, a method of approximating the two tissue planes 252, 254 preferably includes grabbing the elevated second tissue plane 254 (e.g., a flap of tissue) with the non-dominant hand.

Figure 10B:
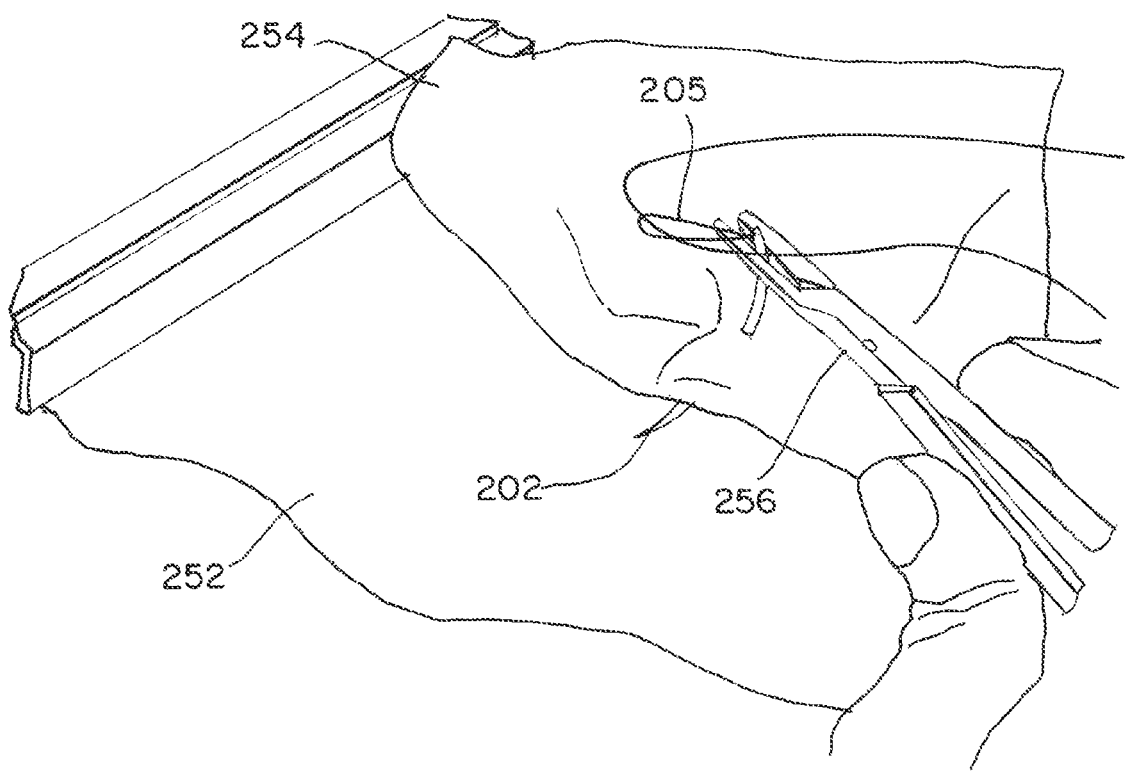
FIG. 10B shows another stage of a method of deploying the suture implant of FIG. 8 for approximating tissue layers, in accordance with one embodiment of the present patent application.
Figure 10C:
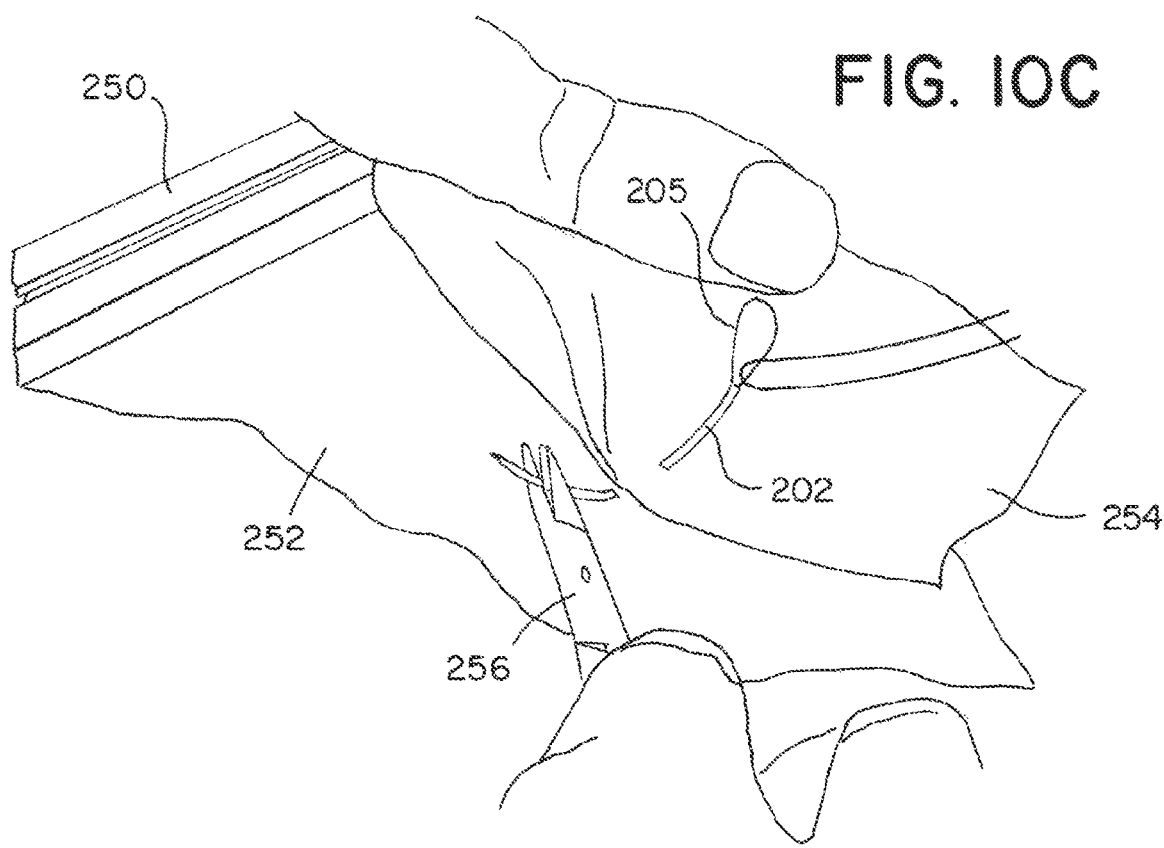
FIG. 10C shows another stage of a method of deploying the suture implant of FIG. 8 for approximating tissue layers, in accordance with one embodiment of the present patent application.

Referring to FIGS. 10B and 10C, in one embodiment, a needle holder 256 may be used to pass the needle 202 that is attached to the small suture loop 205 (FIG. 8A) through both tissue planes 252, 254.

Figure 10D:
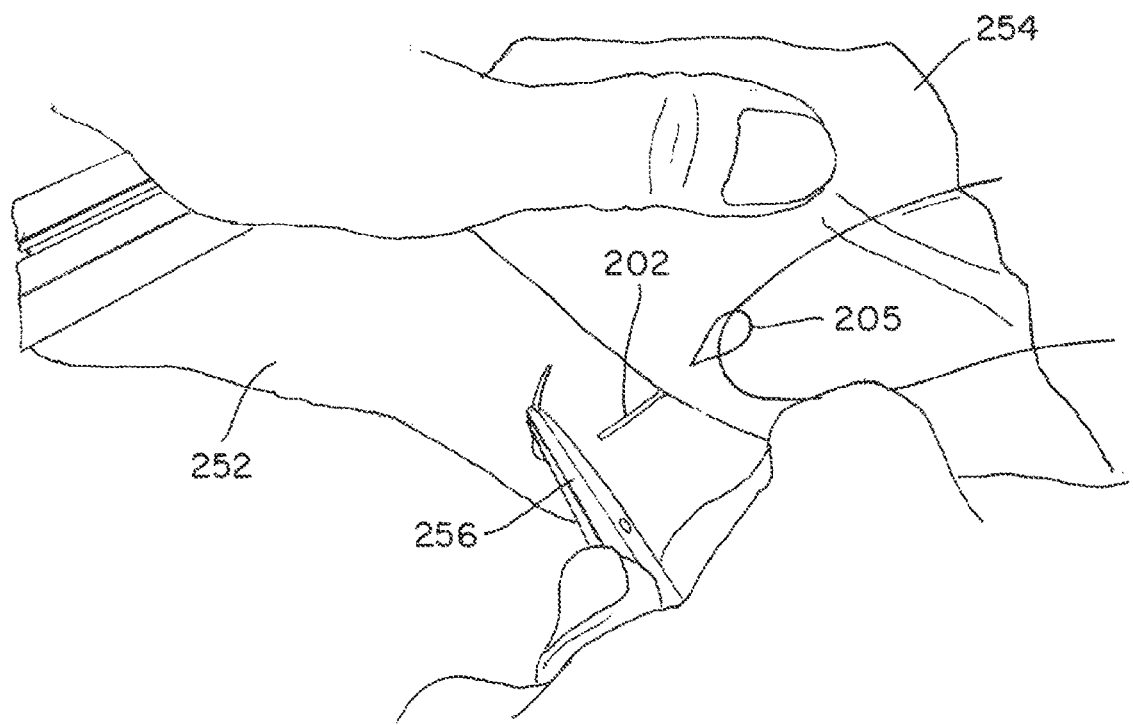
FIG. 10D shows another stage of a method of deploying the suture implant of FIG. 8 for approximating tissue layers, in accordance with one embodiment of the present patent application.
Figure 10E:
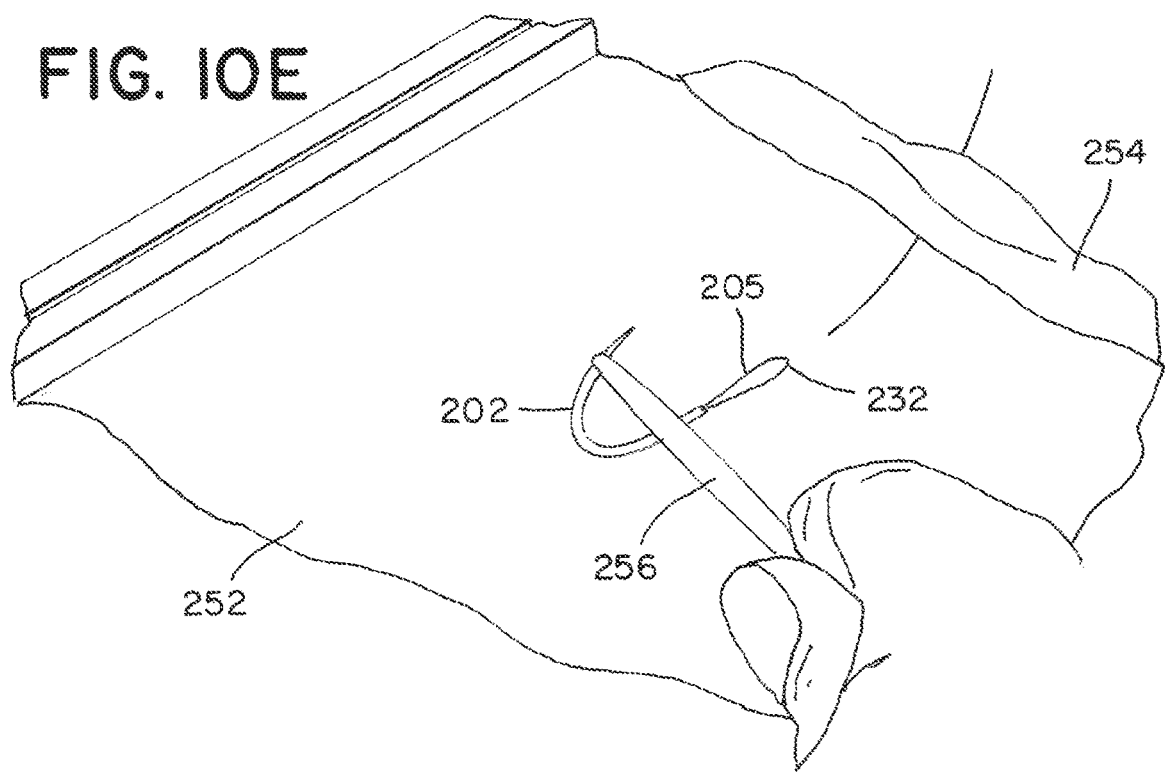
FIG. 10E shows another stage of a method of deploying the suture implant of FIG. 8 for approximating tissue layers, in accordance with one embodiment of the present patent application.
Figure 10F:
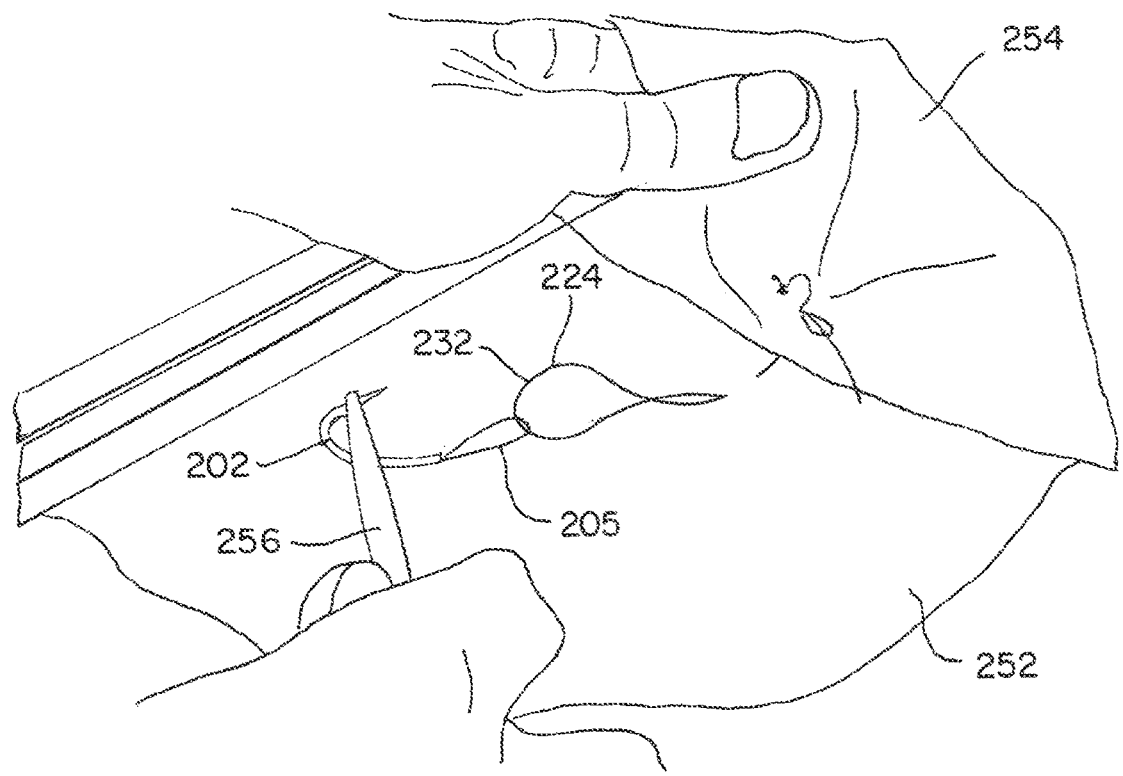
FIG. 10F shows another stage of a method of deploying the suture implant of FIG. 8 for approximating tissue layers, in accordance with one embodiment of the present patent application.

Referring to FIGS. 10D-10F, in one embodiment, the needle holder 256 is used to pull the needle 202 and the small suture loop 205 completely through the first and second tissue planes 252, 254. As the small suture loop 205 is pulled completely through the first and second tissue planes 252, 254, the small suture loop 205 drags the closed end 232 of the large suture loop 224 (FIG. 8A) completely through the first and second tissue planes 252, 254.

Figure 10G:
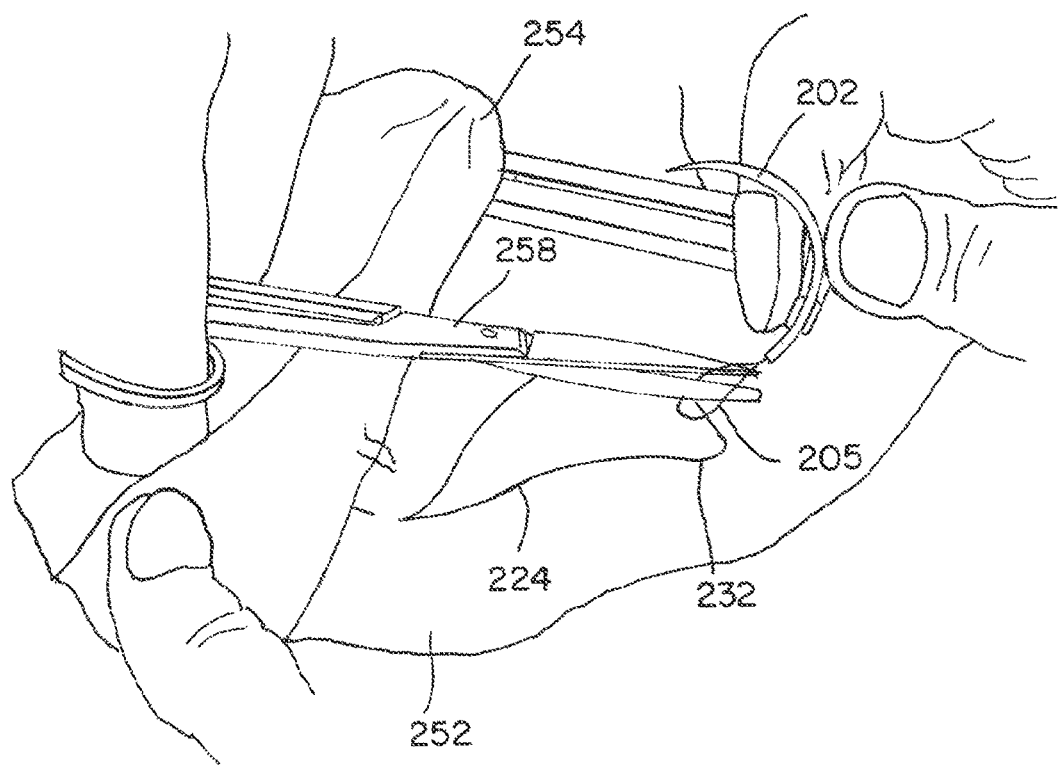
FIG. 10G shows another stage of a method of deploying the suture implant of FIG. 8 for approximating tissue layers, in accordance with one embodiment of the present patent application.

Referring to FIG. 10G, in one embodiment, after the small suture loop 205 and the closed end 232 of the large suture loop 224 have been pulled through the first and second tissue planes 252, 254, the small suture loop 205 that is swaged to the needle 202 may be cut using a cutting tool 258. In one embodiment, the small suture loop 205 may be detached from the needle 202 using a pull-off mechanism whereby the swaged small suture loop 205 is dislodged by pulling the needle 202 at a threshold force that is low enough so that it does not adversely impact the function of the rest of the suture implant.

Figure 10H:
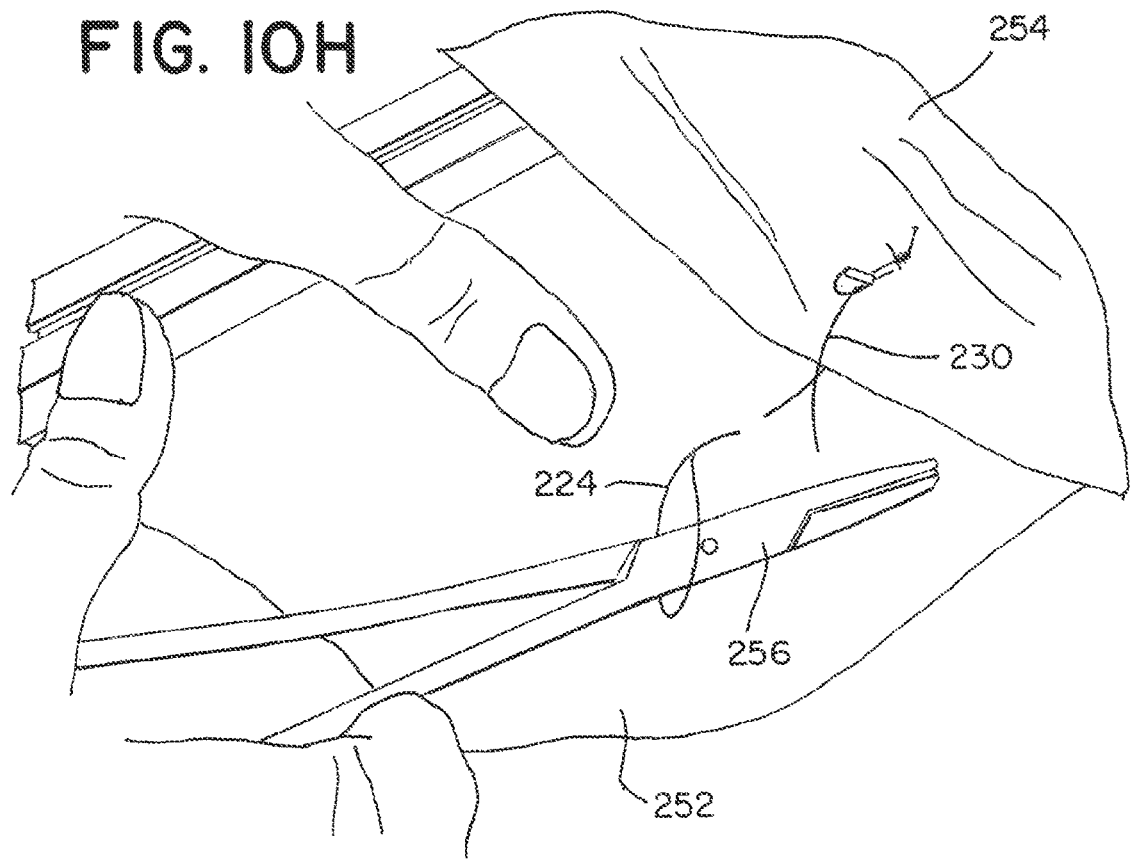
FIG. 10H shows another stage of a method of deploying the suture implant of FIG. 8 for approximating tissue layers, in accordance with one embodiment of the present patent application.
Figure 10I:
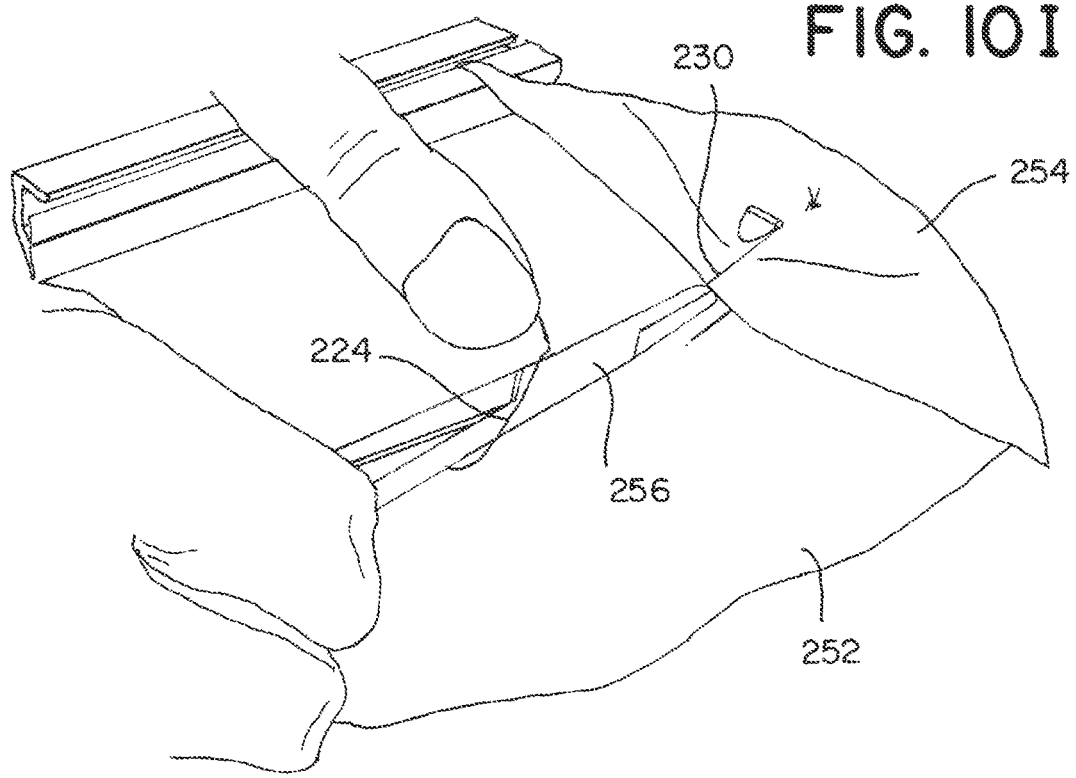
FIG. 10I shows another stage of a method of deploying the suture implant of FIG. 8 for approximating tissue layers, in accordance with one embodiment of the present patent application.

Referring to FIGS. 10H and 10I, in one embodiment, the needle holder 256 may be inserted through the larger suture loop 224 for grabbing the free end of the sliding suture 230.

Figure 10J:
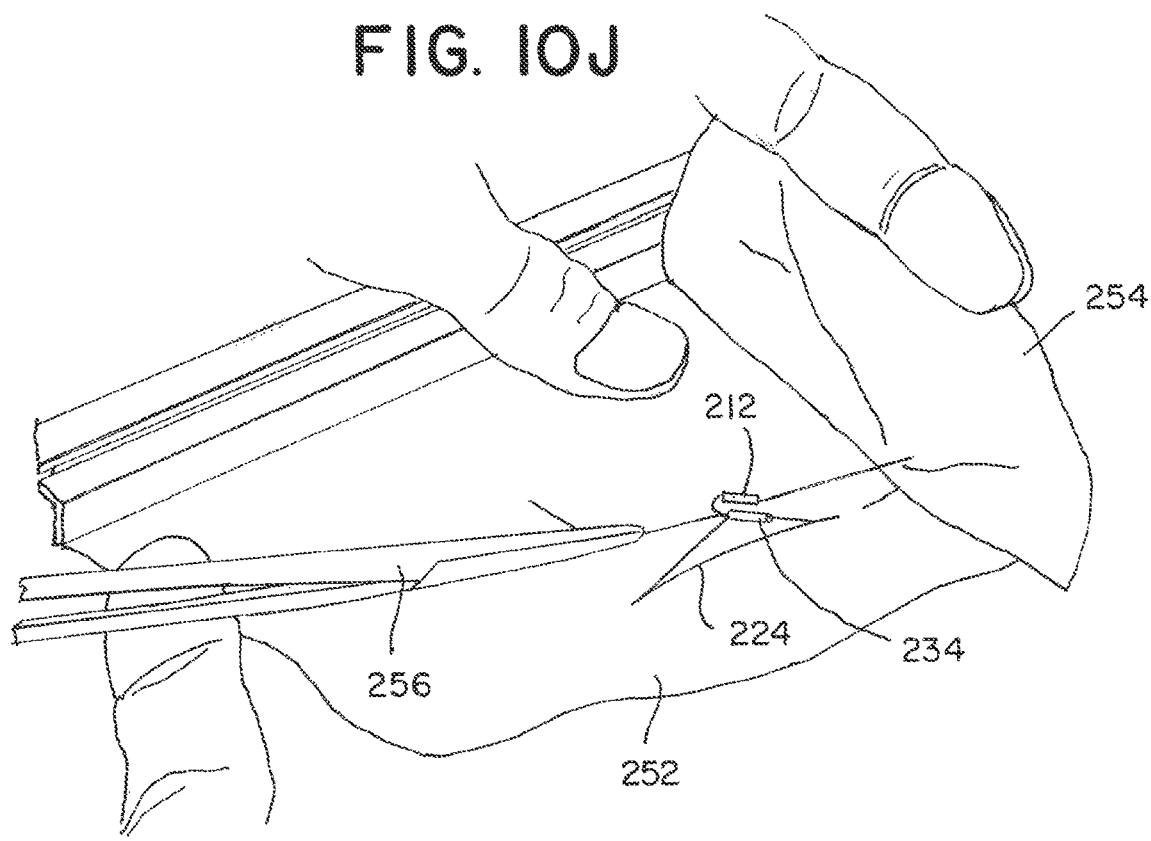
FIG. 10J shows another stage of a method of deploying the suture implant of FIG. 8 for approximating tissue layers, in accordance with one embodiment of the present patent application.
Figure 10K:
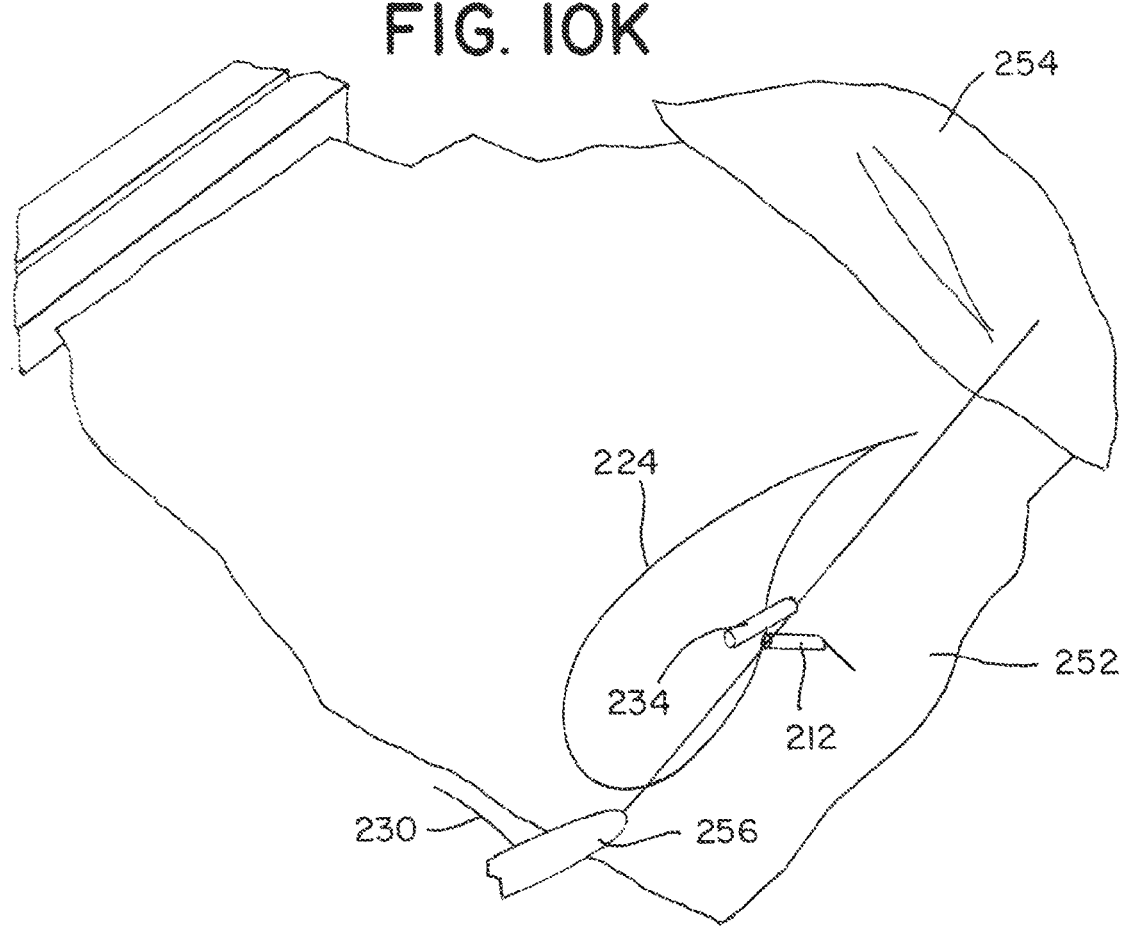
FIG. 10K shows another stage of a method of deploying the suture implant of FIG. 8 for approximating tissue layers, in accordance with one embodiment of the present patent application.

Referring to FIGS. 10J and 10K, in one embodiment, the needle holder 256 is used to pull the sliding suture 230 through the center of the large suture loop 224. In one embodiment, as the sliding suture 230 is pulled through the large suture loop 224, the tissue anchor 212 is also pulled through the large suture loop 224, however, the catch pledget 234 is not pulled through the large suture loop but catches on the outside of the large suture loop 224.

FIG. 10K shows the tissue anchor 212 and the catch pledget 234 straddling the inside and the outside of the large suture loop 224, with the large suture loop 224 passing between the tissue anchor 212 and the catch pledget 234. In one embodiment, the sliding suture is in-line with the leading end 214 of the tissue anchor 212 to facilitate the anchor being pulled to the inside of the suture loop 224 with minimal obstruction.

Figure 10L:
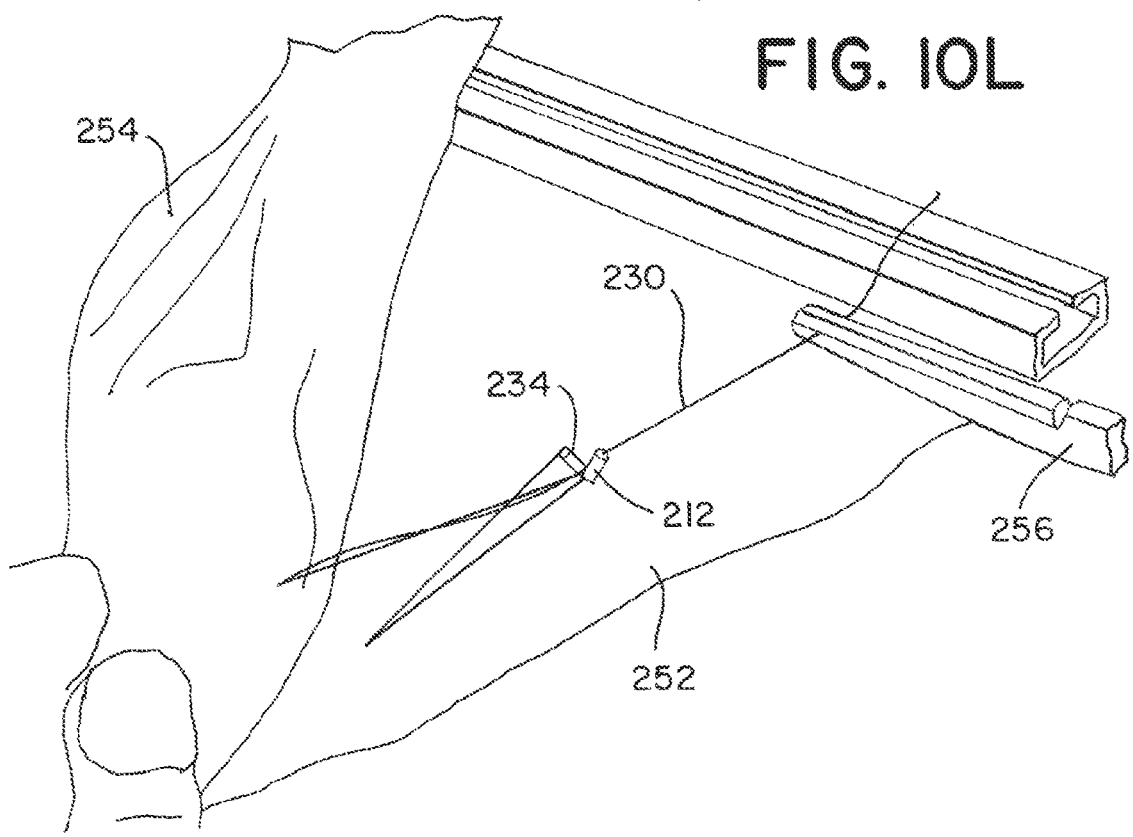
FIG. 10L shows another stage of a method of deploying the suture implant of FIG. 8 for approximating tissue layers, in accordance with one embodiment of the present patent application.
Figure 10M:
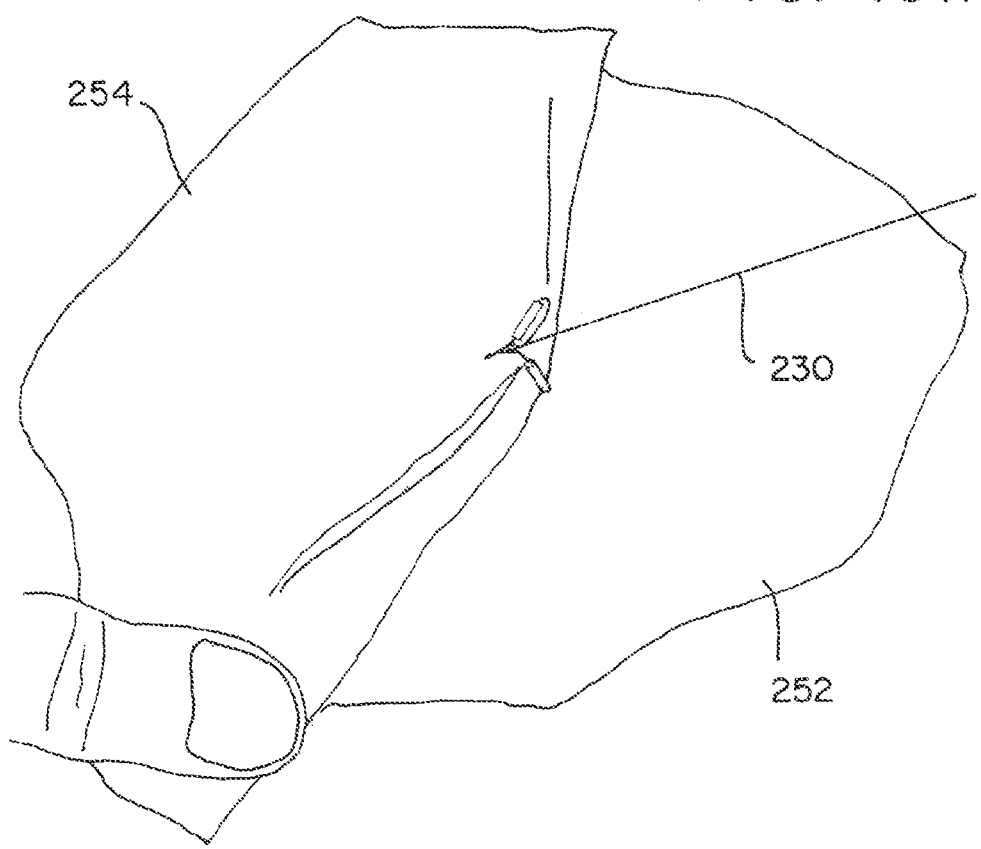
FIG. 10M shows another stage of a method of deploying the suture implant of FIG. 8 for approximating tissue layers, in accordance with one embodiment of the present patent application.

Referring to FIG. 10L, in one embodiment, the sliding suture 230 is pulled to cinch the tissue anchor 212 and the catch pledget 234 downwards toward the interface of the first and second tissue planes 252, 254.

Referring to 10M, in the embodiment, the sliding suture 230 is pulled until the desired amount of tension is applied via the suture implant.

Figure 10N:
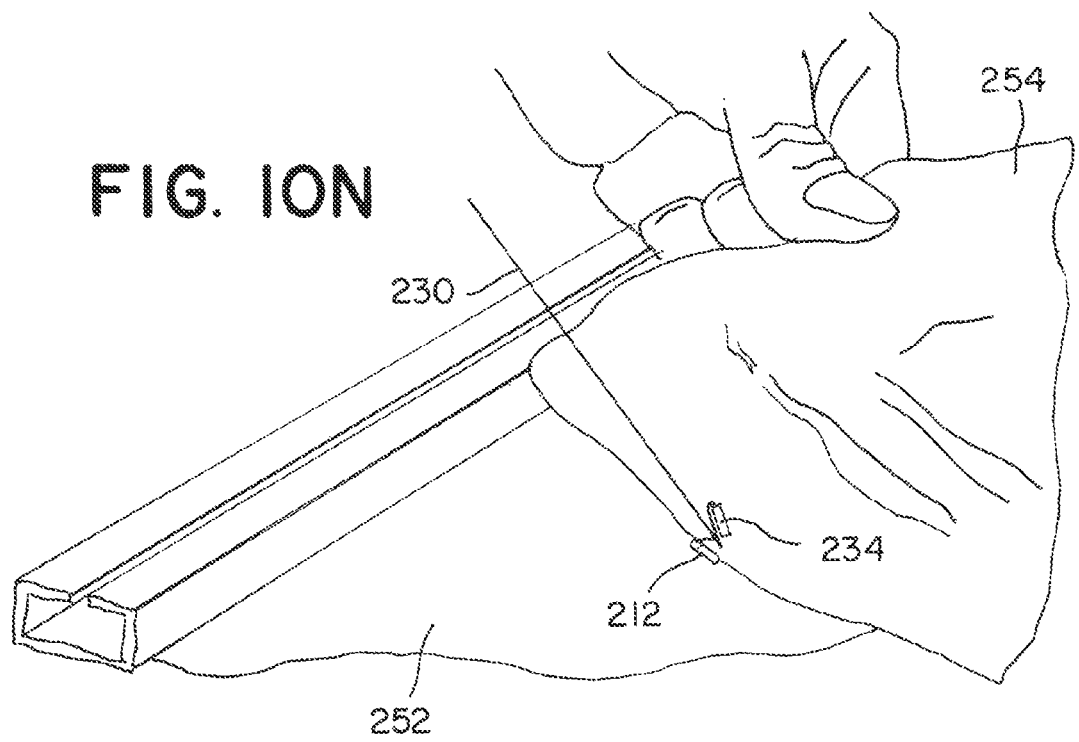
FIG. 10N shows another stage of a method of deploying the suture implant of FIG. 8 for approximating tissue layers, in accordance with one embodiment of the present patent application.
Figure 100:
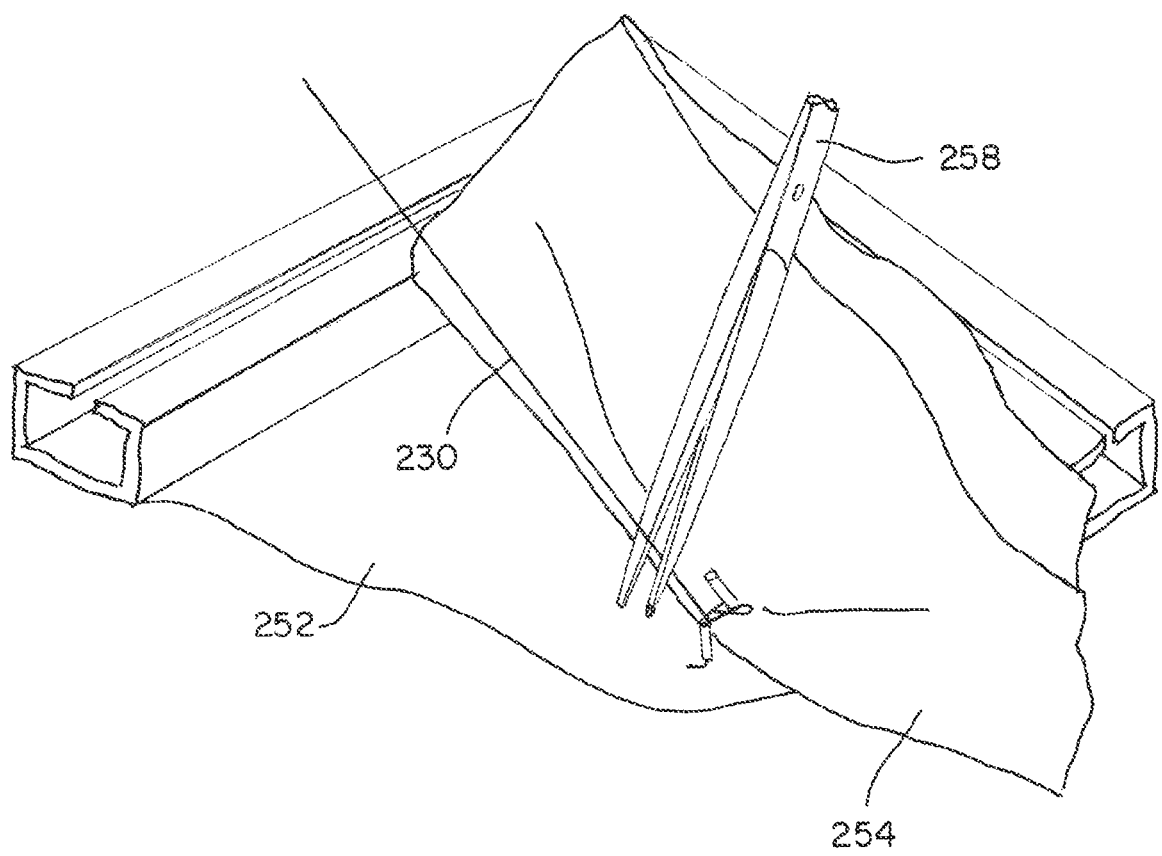

Referring to FIG. 10N, in one embodiment, the tissue anchor 212 and the catch pledge 232 may be toggled by pulling the sliding suture 230 to the side so that the tissue anchor and the catch pledget are perpendicular to the large suture loop 224 (FIG. 10L).

Referring to FIG. 10O, in one embodiment, the excess amount of suture material including the sliding suture 230 may be trimmed away and/or cut using a cutting tool 258.

In the embodiment of FIGS. 8A-10O, the catch pledget 234 (FIGS. 8A and 8B) was required to facilitate sliding of the slip knot. Essentially, it forces the tension on the sliding suture to be transferred into sliding the slip knot 228 rather than compressing the tissue captured by the suture loop. In one embodiment, the catch pledget 234 and the tissue anchor 212 may be designed as a single component rather than two separate components shown above in FIGS. 8A and 8B.

A modified version of the suture implant and implantation methods described above may be possible by pulling the sliding suture outside of the suture loop rather than through the center of the suture loop. When using this implantation and tensioning technique, a catch pledge is not required, Given the dexterity required for this technique, implantation may be easier by hand rather than using needle holders.

Figure 11:
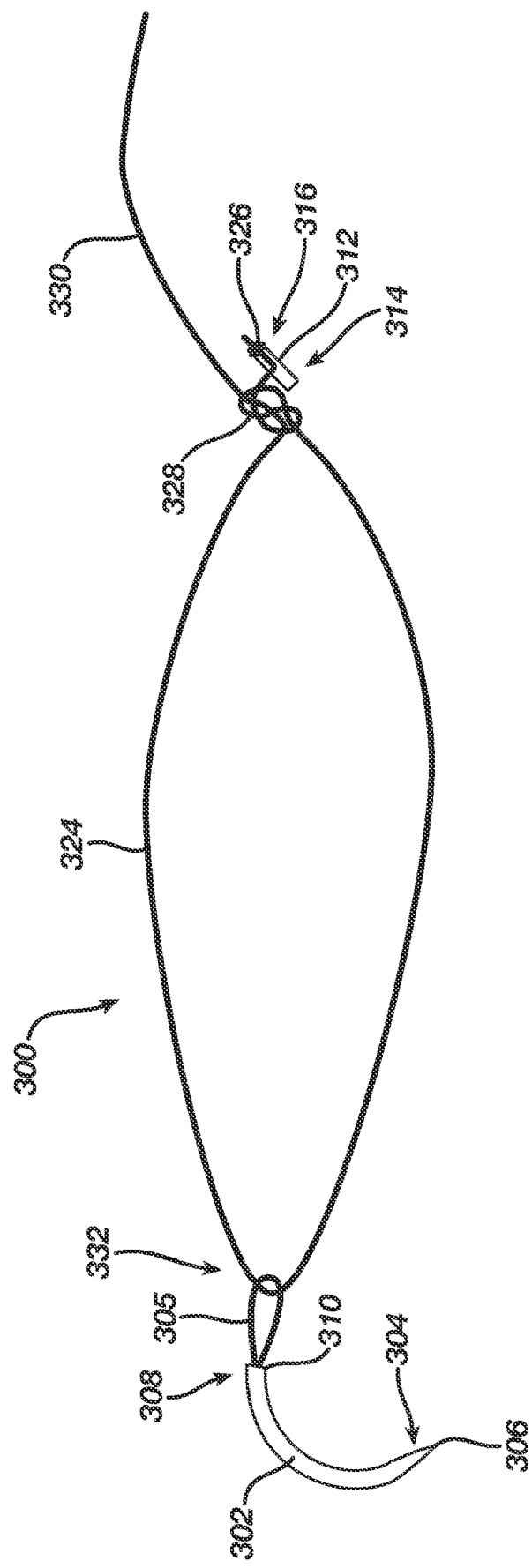
FIG. 11 is a schematic view of a suture implant used for approximating tissue including a needle, a small suture loop, a large suture loop, a slip knot, a fixed knot, a sliding suture, and a tissue anchor, in accordance with one embodiment of the present patent application.

Referring to FIG. 11, in one embodiment, a suture implant 300 used for approximating tissue (e.g., approximating two tissue planes) preferably includes a needle 302 having a leading end 304 with a sharpened point 306 and a trailing end 308 that includes a suture swage attachment 310. In one embodiment, the needle 302 is a suture needle that is adapted for suturing tissue. In one embodiment, the suture needle 302 may be curved.

In one embodiment, the suture implant 300 preferably includes a small suture loop 305 that is attached to the suture swage attachment 310. In one embodiment, the free ends of the small suture loop 305 are swaged to the suture swage attachment 310 of the needle 302.

In one embodiment, the suture implant 300 preferably includes a tissue anchor 312 having a leading or distal end 314 and a trailing or proximal end 316. The suture implant 300 desirably includes a large suture loop 324 having a first end with a fixed knot 326 that is located adjacent the proximal end 316 of the tissue anchor 312, and a slip knot 328 adjacent an underside of the tissue anchor 312. In one embodiment, the large suture loop 324 preferably has a second end including a sliding suture 330 that extends through and/or out of the slip knot 328. In one embodiment, the large suture loop 324 has a closed end 332 that passes through the opening of the small suture loop 305 for interconnecting the small suture loop and the large suture loop.

Figure 12A:
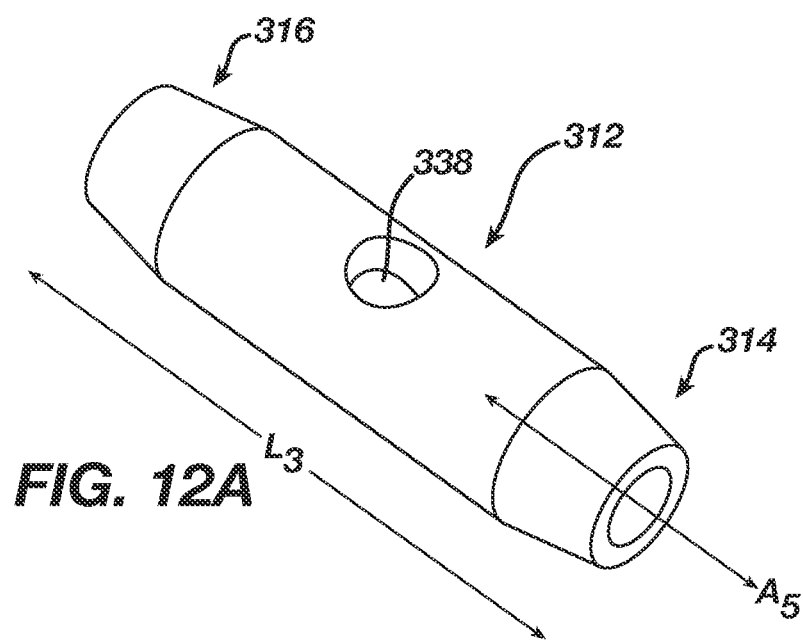
FIG. 12A is a perspective view of the tissue anchor of the suture implant shown in FIG. 11.
Figure 12B:
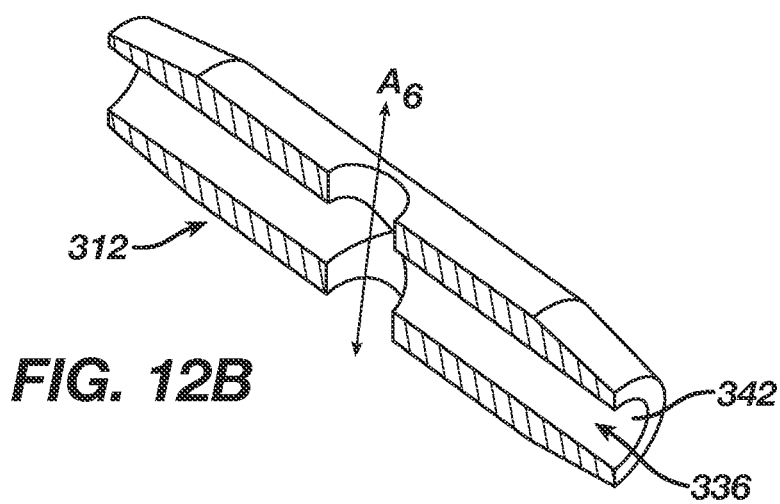
FIG. 12B is a cross-sectional view of the tissue anchor shown in FIG. 12A.

Referring to FIGS. 12A-12B, in one embodiment, the tissue anchor 312 preferably includes the distal end 314 (i.e., the leading end) and the proximal end 316 (i.e., the trailing end). In one embodiment, the tissue anchor 312 preferably defines a tubular or cylindrical shaped body. In one embodiment, the distal and proximal ends 314, 316 of the tissue anchor 312 may be tapered.

In one embodiment, the tissue anchor 312 preferably has a longitudinal axis $A_5$ (FIG. 12B) that extends along the length $L_3$ thereof. The tissue anchor 312 desirably has an elongated channel 336 that extends along the length $L_3$ of the tissue anchor and between the distal and proximal ends 314, 316 of the tissue anchor. In one embodiment, tissue anchor 312 preferably includes a laterally extending channel 338 that extends along a laterally extending axis $A_6$ that is substantially perpendicular to the longitudinal axis $A_5$.

Figure 12C:
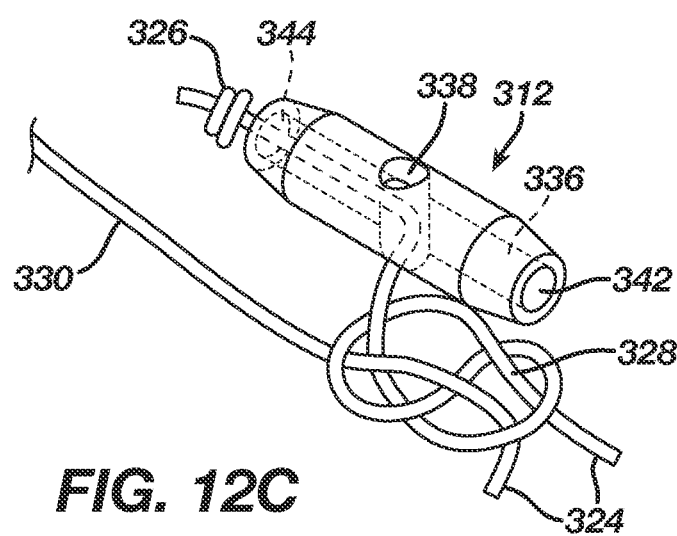
FIG. 12C is a partial cross-sectional view of the tissue anchor shown in FIGS. 12A and 12B.

Referring to FIG. 12C, in one embodiment, the distal end of the elongated channel 336 preferably defines a distal opening 342. The proximal end of the elongated channel 336 defines a proximal opening 344 that is configured to receive the fixed knot 326 located at the first end of the large suture loop 324 (FIG. 11). The sliding suture 330 extends directly out of the slip knot 328. In one embodiment, the slip knot 328 may be located below the lower end of the laterally extending channel 338 (FIG. 12B) and/or be located at the underside of the body of the tissue anchor 312.

Figure 13A:
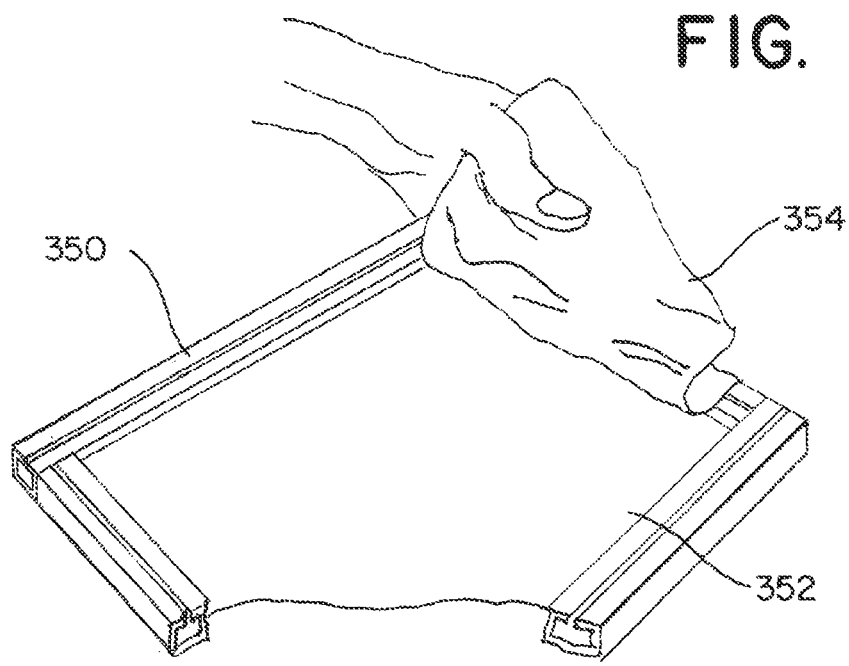
FIG. 13A shows a first stage of a method of deploying the suture implant of FIG. 11 for approximating tissue layers, in accordance with one embodiment of the present patent application.

FIGS. 13A-13O illustrate methods of using the suture implant 300 shown and described above in FIGS. 11 and 12A-12C for approximating tissue, such as approximating two parallel tissue planes.

Referring to FIG. 13A, a simulated fixture 350 holds first and second tissue planes 352 and 354. The second tissue plane 354 may be a flap of tissue that has been cut away from the first tissue plane 352. In one embodiment, a method of approximating the two tissue planes 352, 354 preferably includes grabbing the elevated second tissue plane 354 (e.g., a flap of tissue) with the non-dominant hand.

Figure 13B:
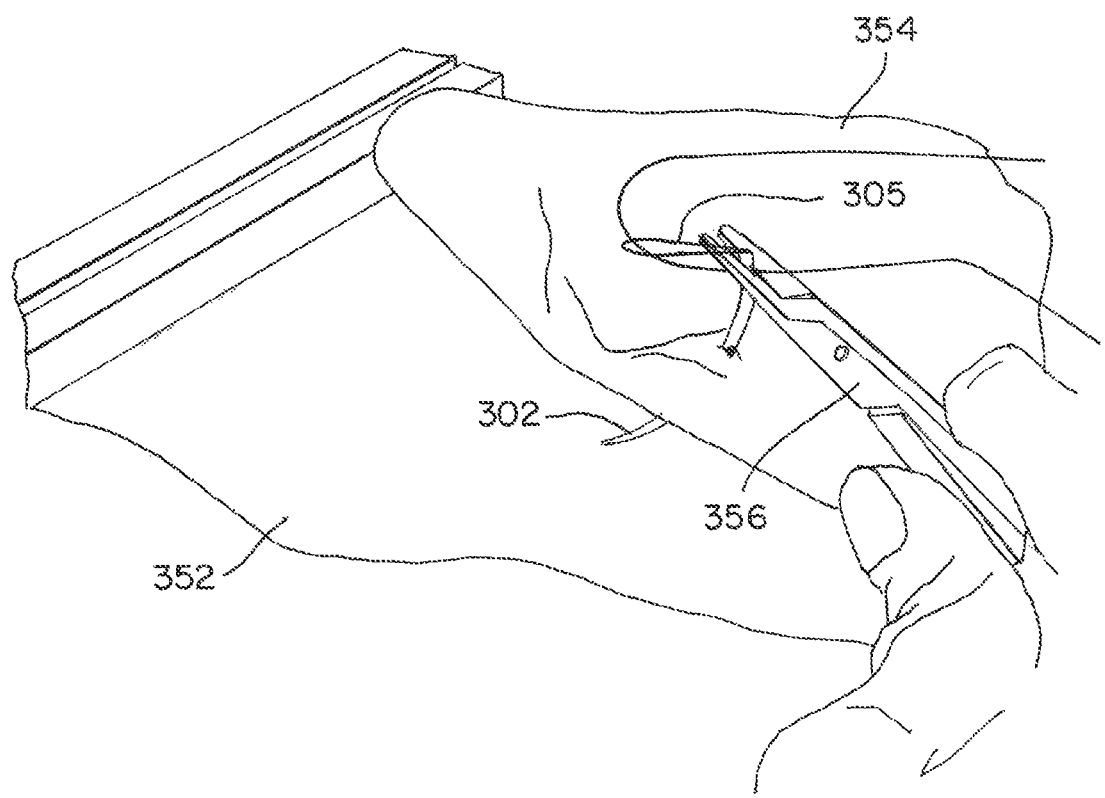
FIG. 13B shows another stage of a method of deploying the suture implant of FIG. 11 for approximating tissue layers, in accordance with one embodiment of the present patent application.
Figure 13C:
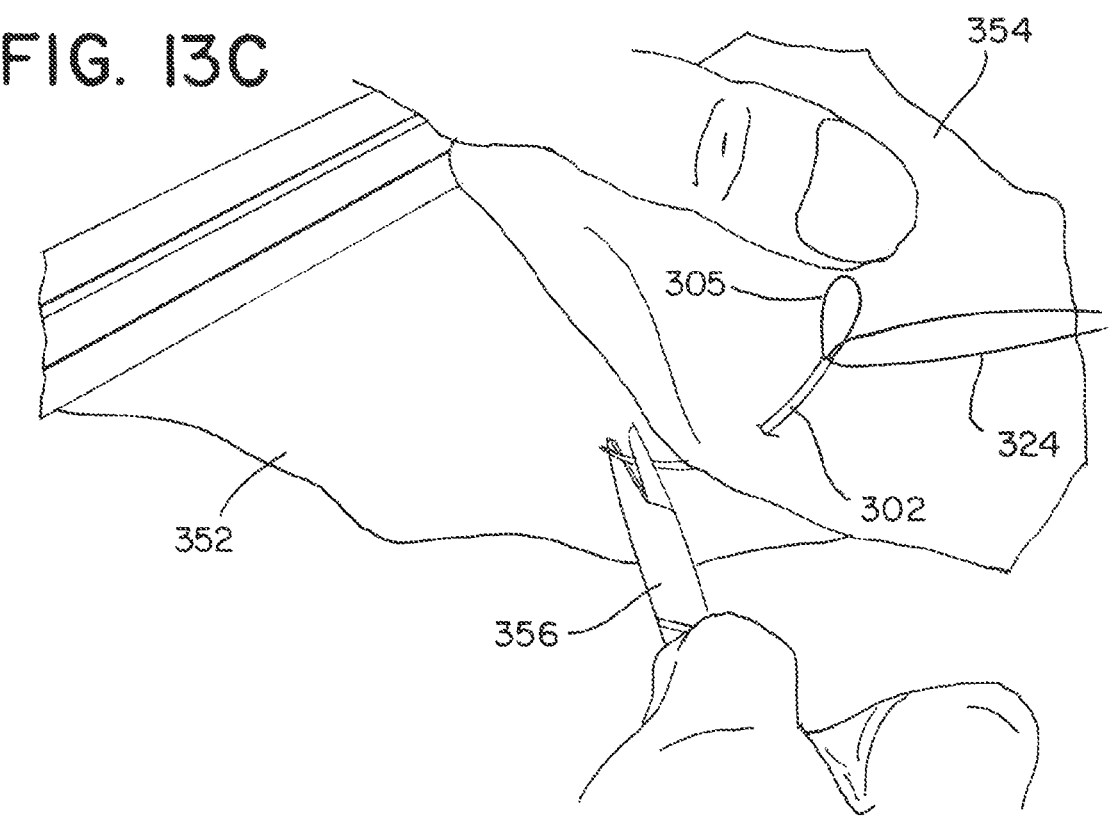
FIG. 13C shows another stage of a method of deploying the suture implant of FIG. 11 for approximating tissue layers, in accordance with one embodiment of the present patent application.

Referring to FIGS. 13B and 13C, in one embodiment, a needle holder 356 may be used to pass the needle 302 that is attached to the small suture loop 305 (FIG. 11) through both tissue planes 352, 354.

Figure 13D:
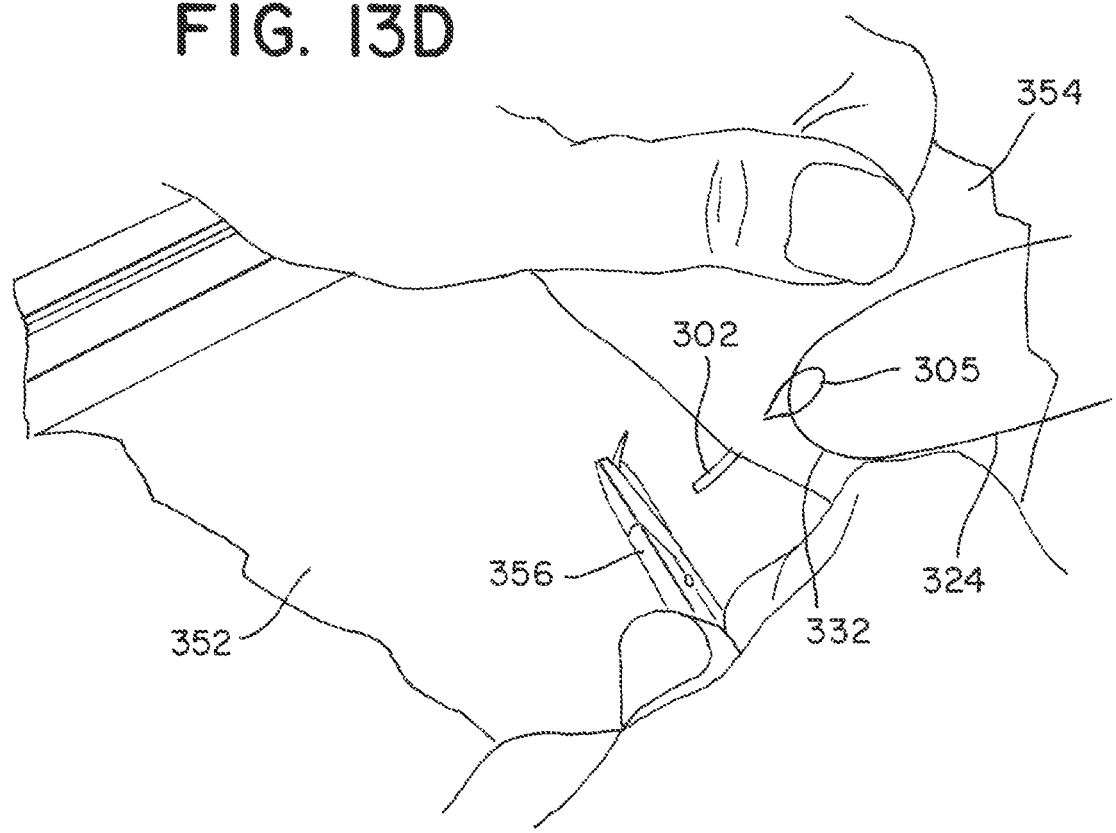
FIG. 13D shows another stage of a method of deploying the suture implant of FIG. 11 for approximating tissue layers, in accordance with one embodiment of the present patent application.
Figure 13E:
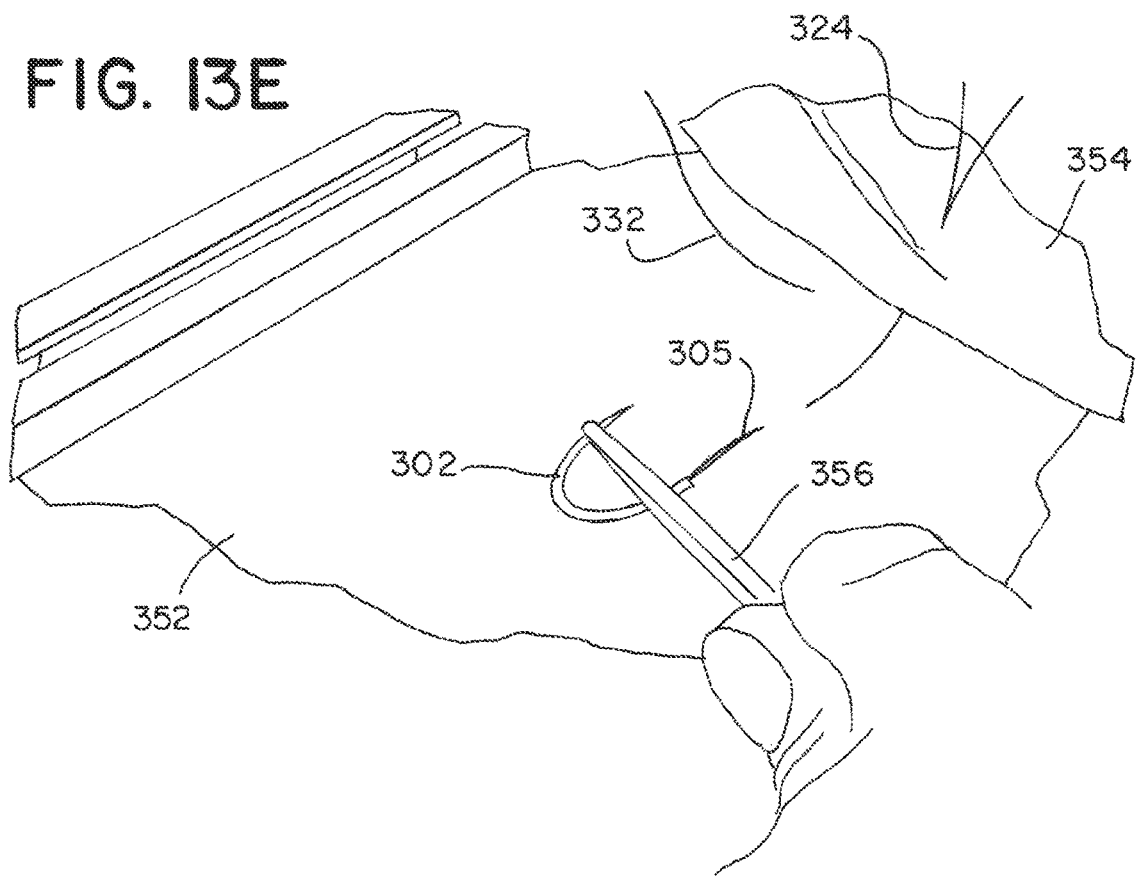
FIG. 13E shows another stage of a method of deploying the suture implant of FIG. 11 for approximating tissue layers, in accordance with one embodiment of the present patent application.
Figure 13F:
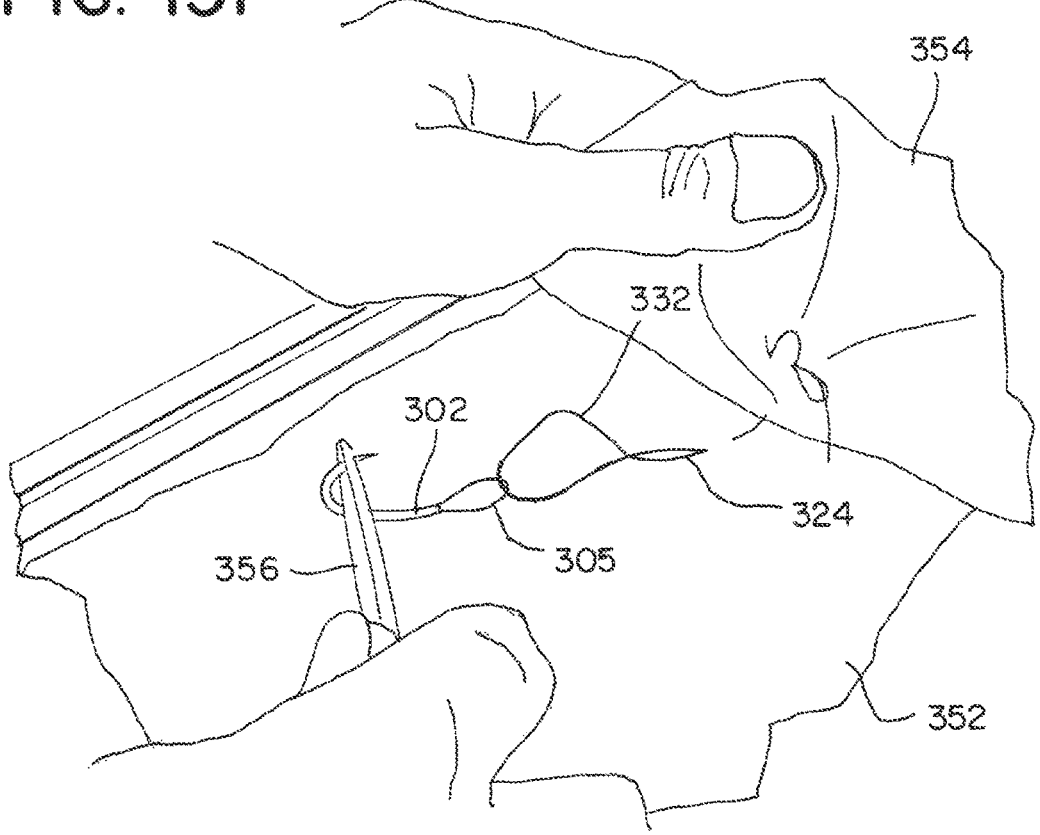
FIG. 13F shows another stage of a method of deploying the suture implant of FIG. 11 for approximating tissue layers, in accordance with one embodiment of the present patent application.

Referring to FIGS. 13D-13F, in one embodiment, the needle holder 356 is used to pull the needle 302 and the small suture loop 305 completely through the first and second tissue planes 352, 354. As the small suture loop 305 is pulled completely through the first and second tissue planes 352, 354, the small suture loop 305 drags the closed end 332 of the large suture loop 324 completely through the first and second tissue planes 352, 354.

Figure 13G:
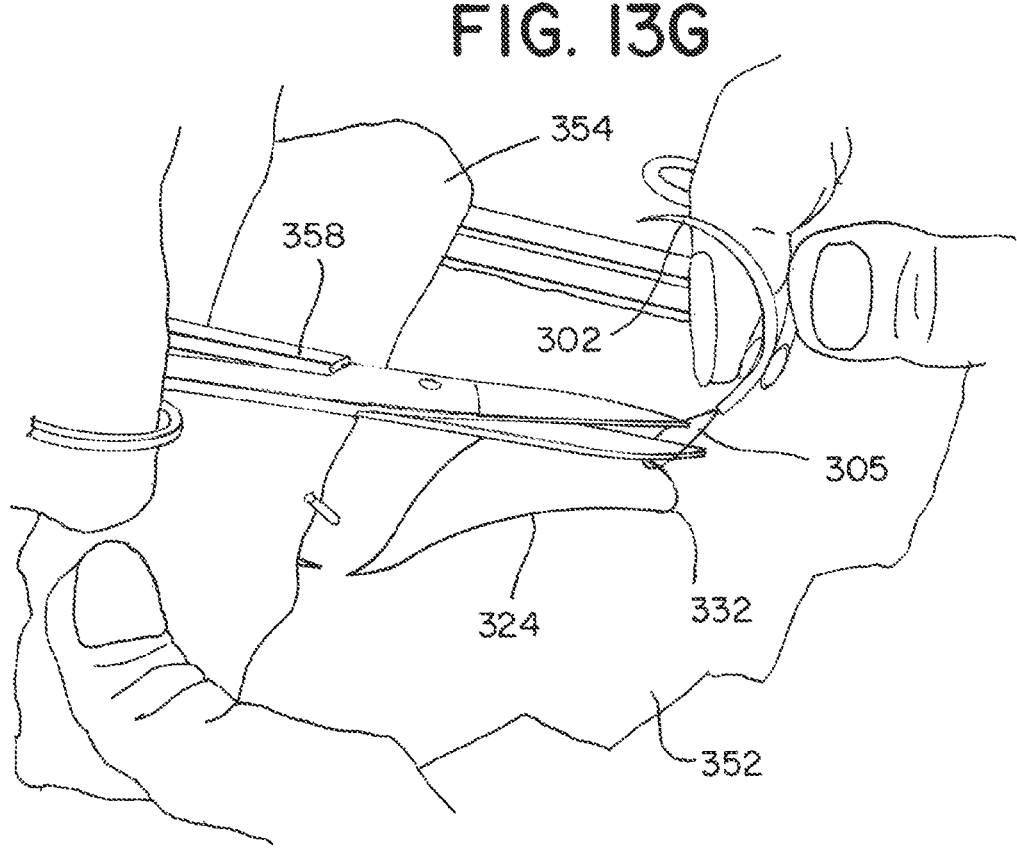
FIG. 13G shows another stage of a method of deploying the suture implant of FIG. 11 for approximating tissue layers, in accordance with one embodiment of the present patent application.

Referring to FIG. 13G, in one embodiment, after the small suture loop 305 and the closed end 332 of the large suture loop 324 have been pulled through the first and second tissue planes 352, 354, the small suture loop 305 that is swaged to the needle 302 may be cut using a cutting tool 358. In one embodiment, the small suture loop 305 may be detached from the needle using a pull-off mechanism whereby the swaged small suture loop 305 is dislodged by pulling the needle 302 at a threshold force that is low enough so that it does not adversely impact the function of the rest of the suture implant assembly.

Figure 13H:
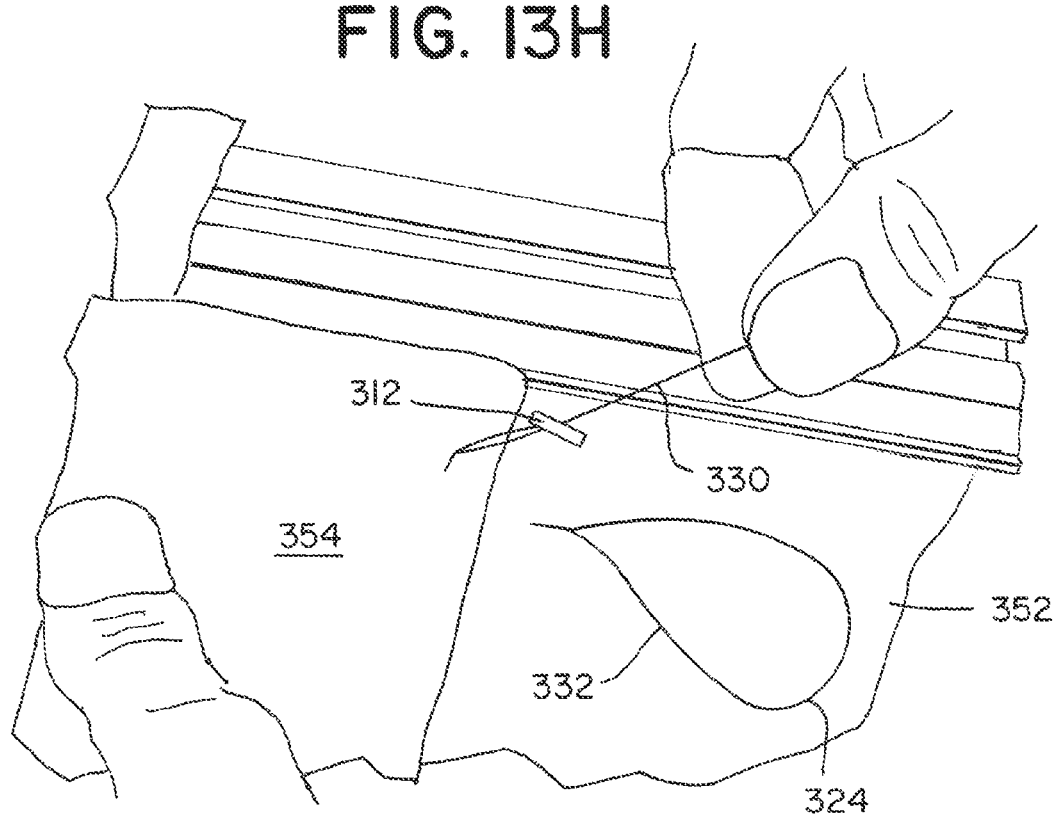
FIG. 13H shows another stage of a method of deploying the suture implant of FIG. 11 for approximating tissue layers, in accordance with one embodiment of the present patent application.

Referring to FIG. 13H, in one embodiment, the free end of the sliding suture 230 may be grabbed between fingers, such as between a thumb and an index finger.

Figure 13I:
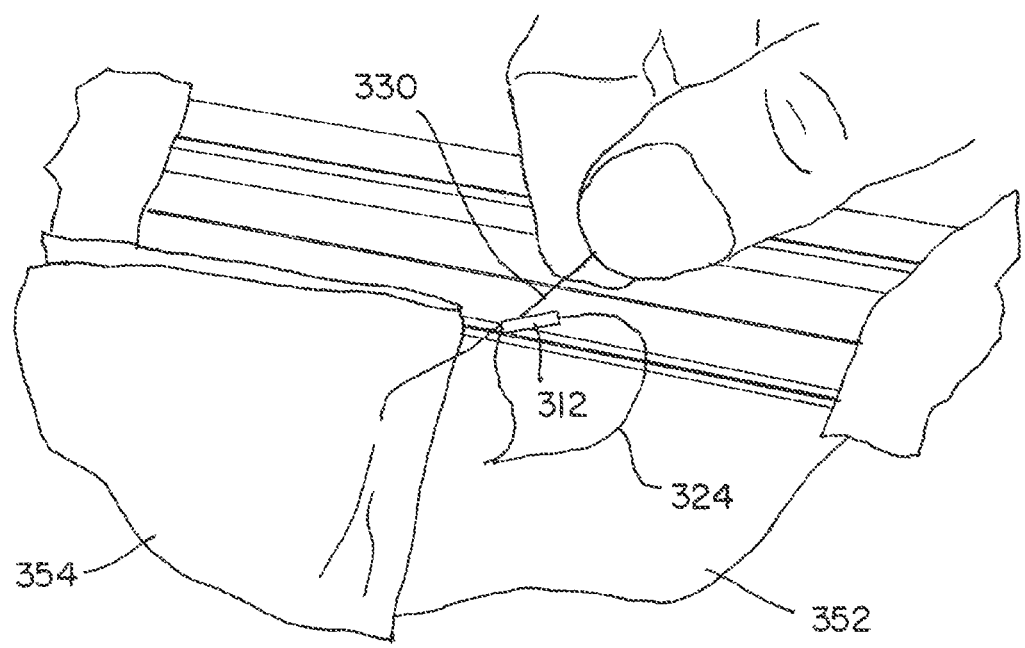
FIG. 13I shows another stage of a method of deploying the suture implant of FIG. 11 for approximating tissue layers, in accordance with one embodiment of the present patent application.
Figure 13J:
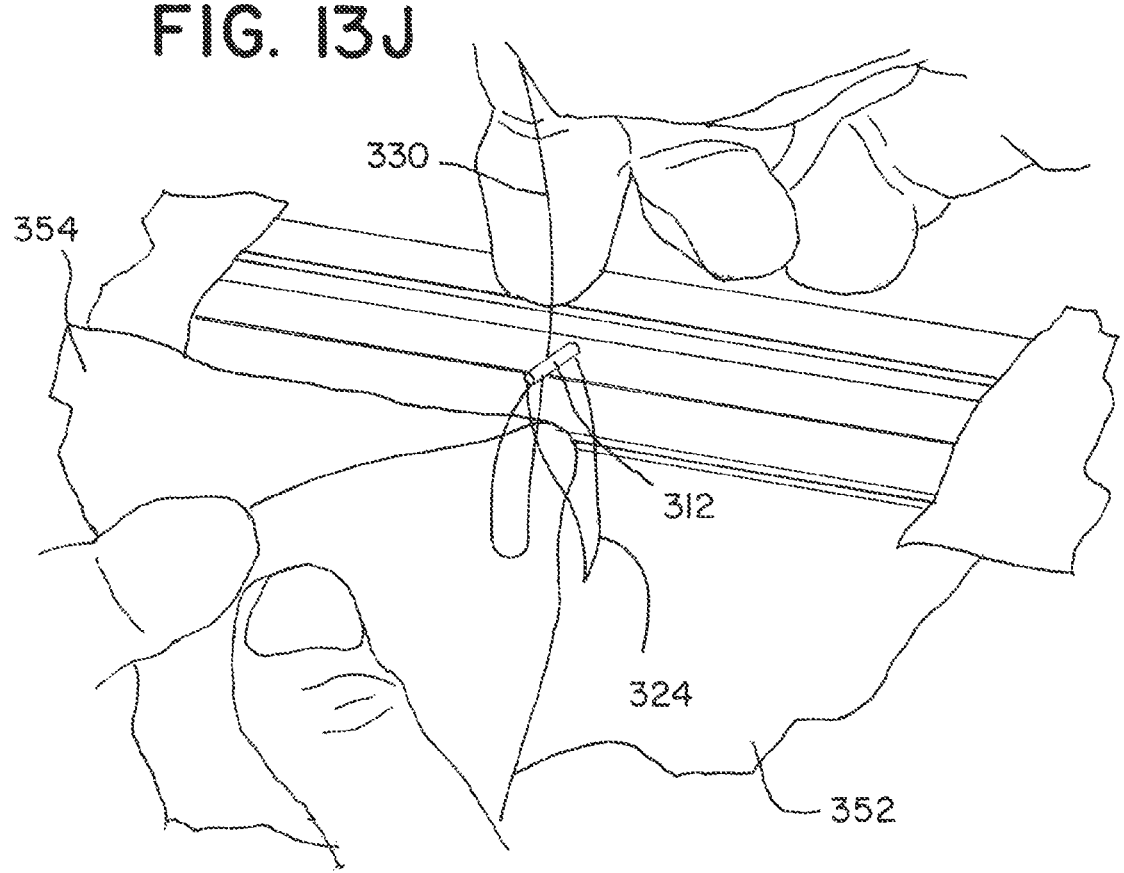
FIG. 13J shows another stage of a method of deploying the suture implant of FIG. 11 for approximating tissue layers, in accordance with one embodiment of the present patent application.

Referring to FIGS. 13I and 13J, in one embodiment, the tissue anchor 312 is positioned so that it is captured within the large suture loop 324, while keeping the sliding suture 330 outside the large suture loop 324. The above-described orientation of the tissue anchor 312 and the sliding suture 330 causes an automatic catching effect on the large suture loop 324. In one embodiment, the sliding suture 330 is pulled to apply tension while ensuring that the tissue anchor 312 remains within the large suture loop 324.

Figure 13K:
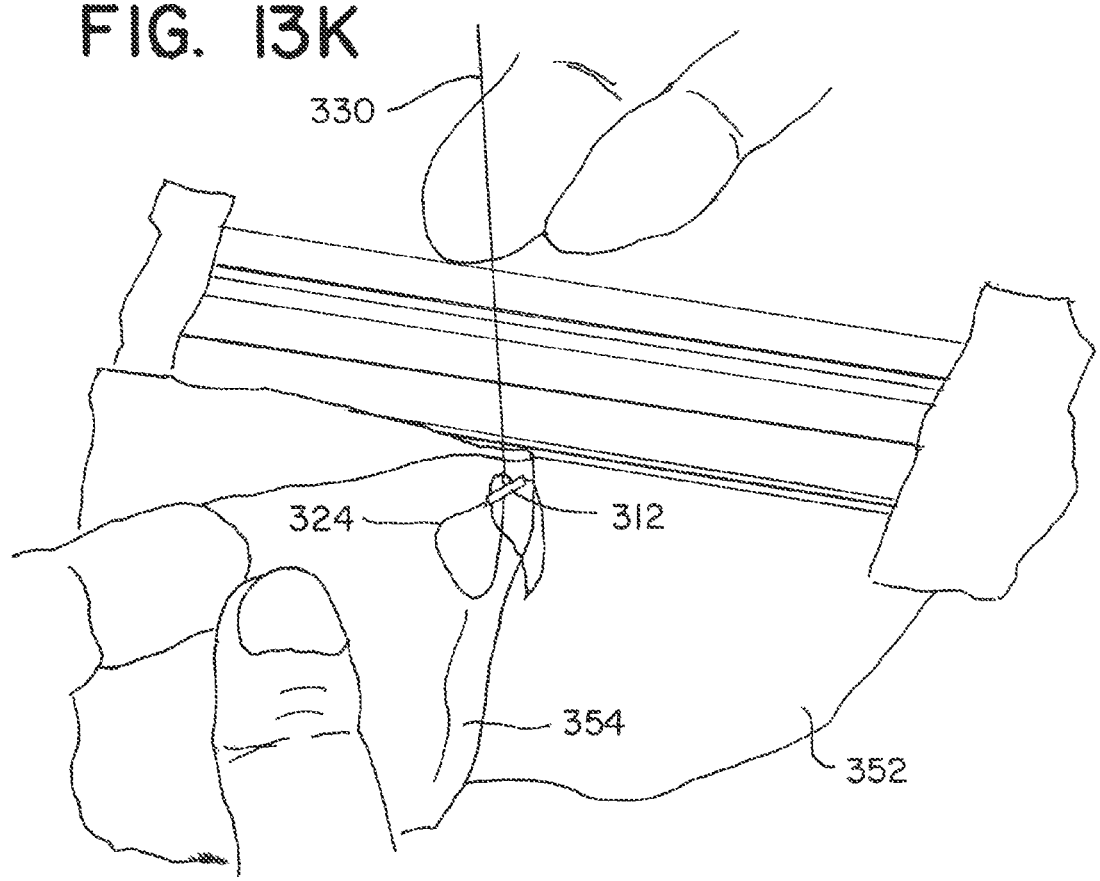
FIG. 13K shows another stage of a method of deploying the suture implant of FIG. 11 for approximating tissue layers, in accordance with one embodiment of the present patent application.
Figure 13L:
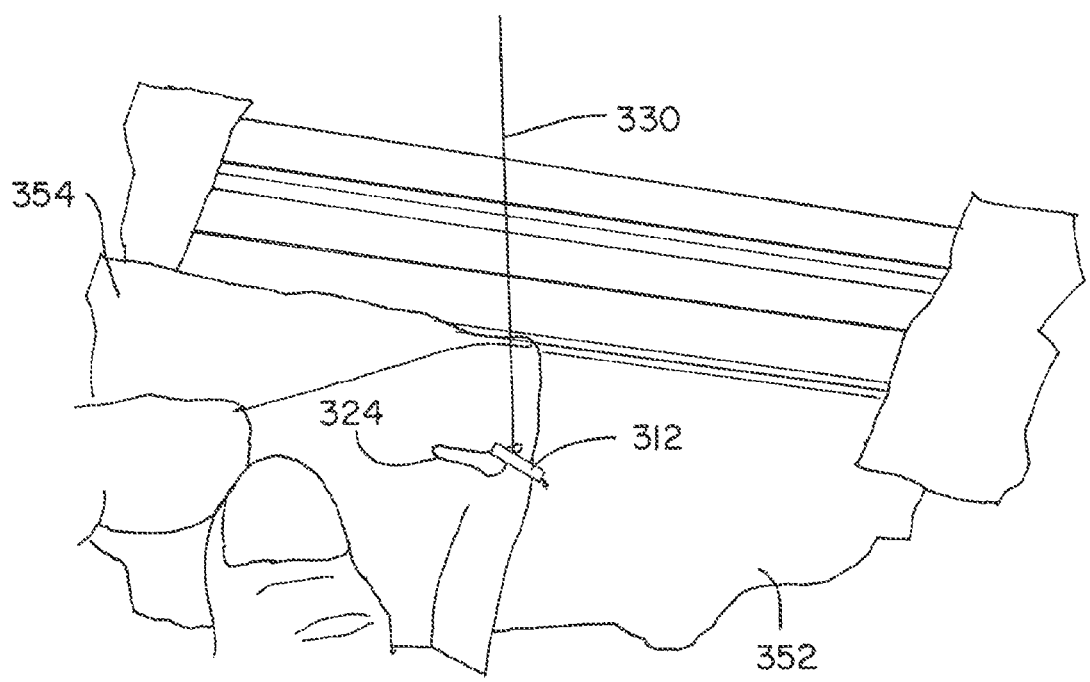
FIG. 13L shows another stage of a method of deploying the suture implant of FIG. 11 for approximating tissue layers, in accordance with one embodiment of the present patent application.
Figure 13M:
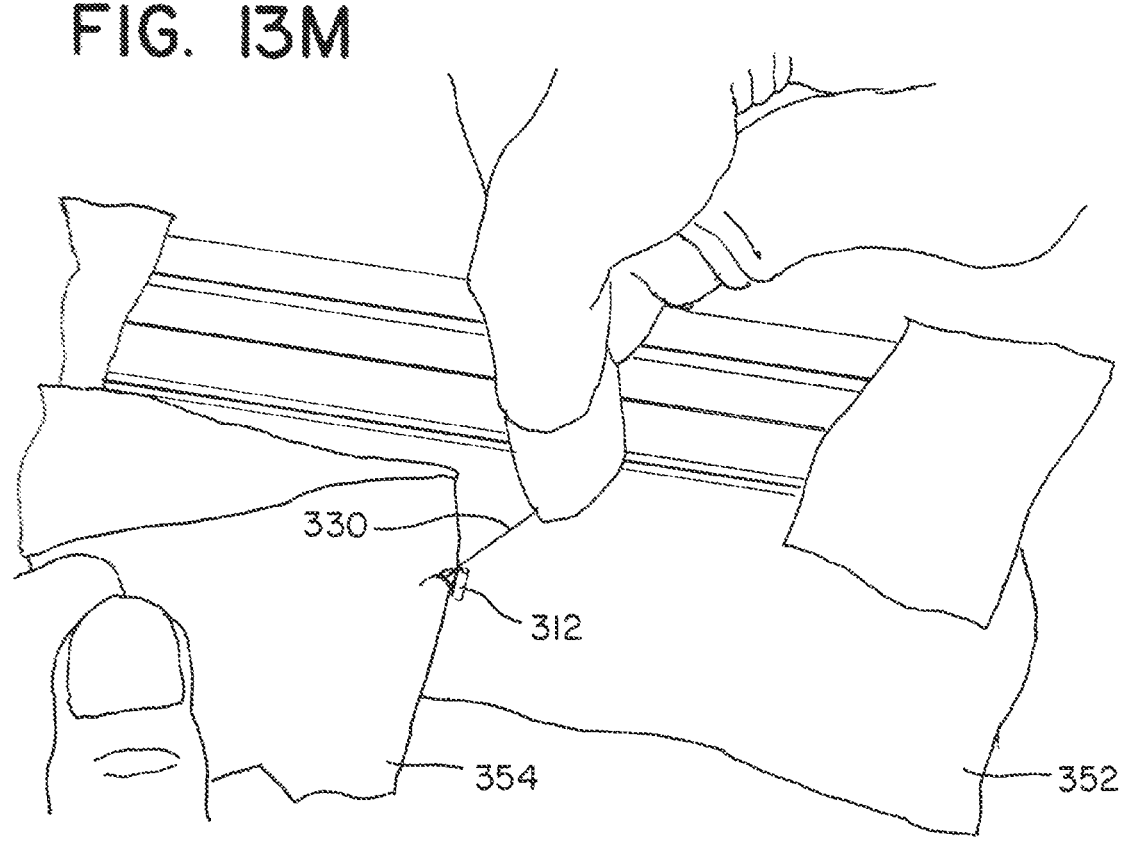
FIG. 13M shows another stage of a method of deploying the suture implant of FIG. 11 for approximating tissue layers, in accordance with one embodiment of the present patent application.

Referring to FIGS. 13K-13M, in one embodiment, the sliding suture 330 is pulled to cinch the tissue anchor 312 downwards toward the first and second tissue planes 352, 354. In one embodiment, the sliding suture 330 is pulled until the desired amount of tension is applied. In one embodiment, the tissue anchor 312 is toggled, such as by pulling the sliding suture 330 to the side, so that the tissue anchor is perpendicular to the large suture loop 324 for maximizing surface area contact between the tissue anchor 312 and the tissue.

Figure 13N:
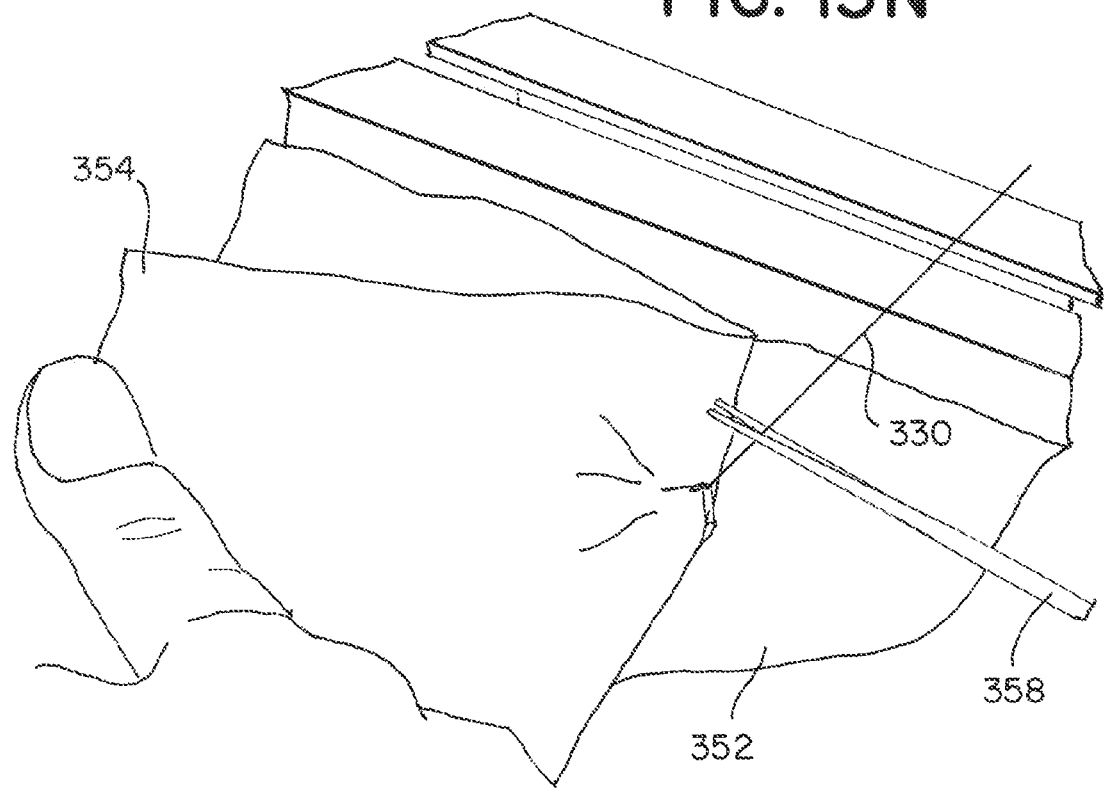
FIG. 13N shows another stage of a method of deploying the suture implant of FIG. 11 for approximating tissue layers, in accordance with one embodiment of the present patent application.
Figure 130:
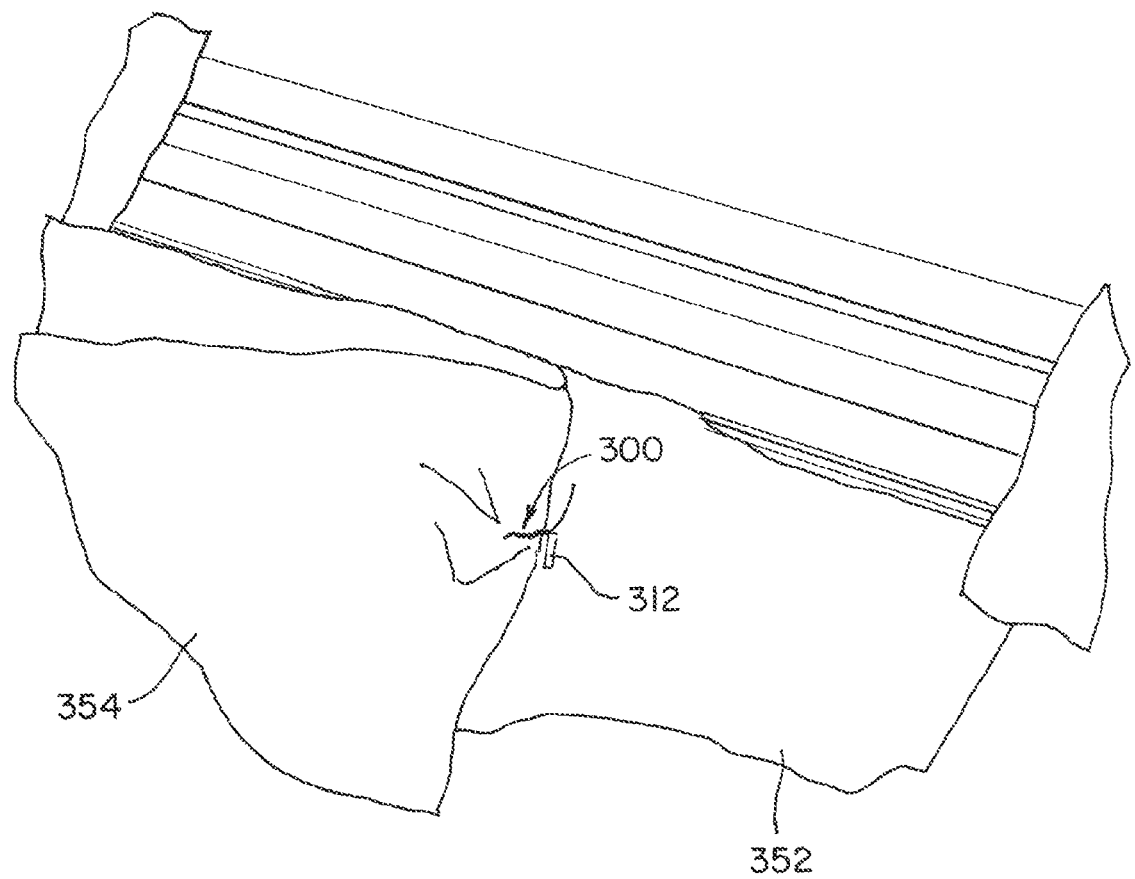

Referring to FIG. 13N, in one embodiment, the excess amount of suture material including the sliding suture 330 may be trimmed away and/or cut using a cutting tool 358.

Referring to FIG. 13O, in one embodiment, after the excess suture material is trimmed away, the suture implant 300 including the tissue anchor 312 approximates the first and second tissue layers 352, 354.

Figure 14A:
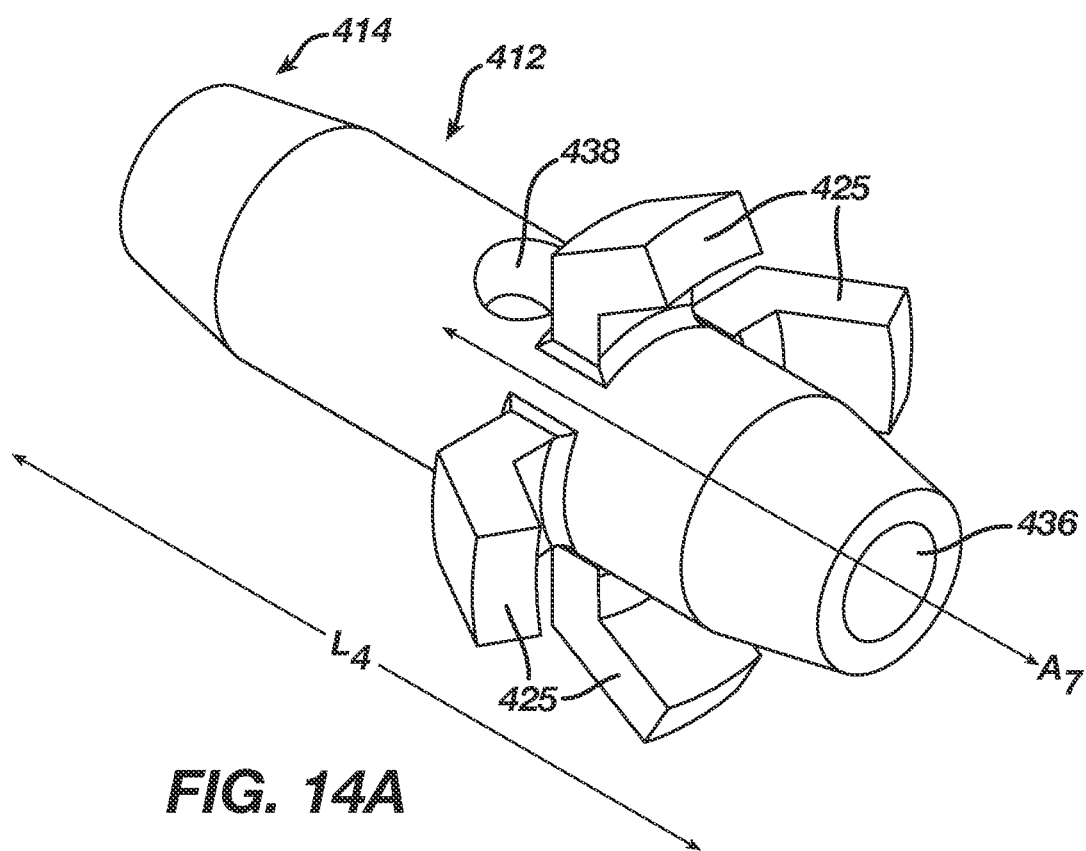
FIG. 14A is a perspective view of a top side of a tissue anchor/catch pledget of a suture implant for approximating tissue layers, in accordance with one embodiment of the present patent application.
Figure 14B:
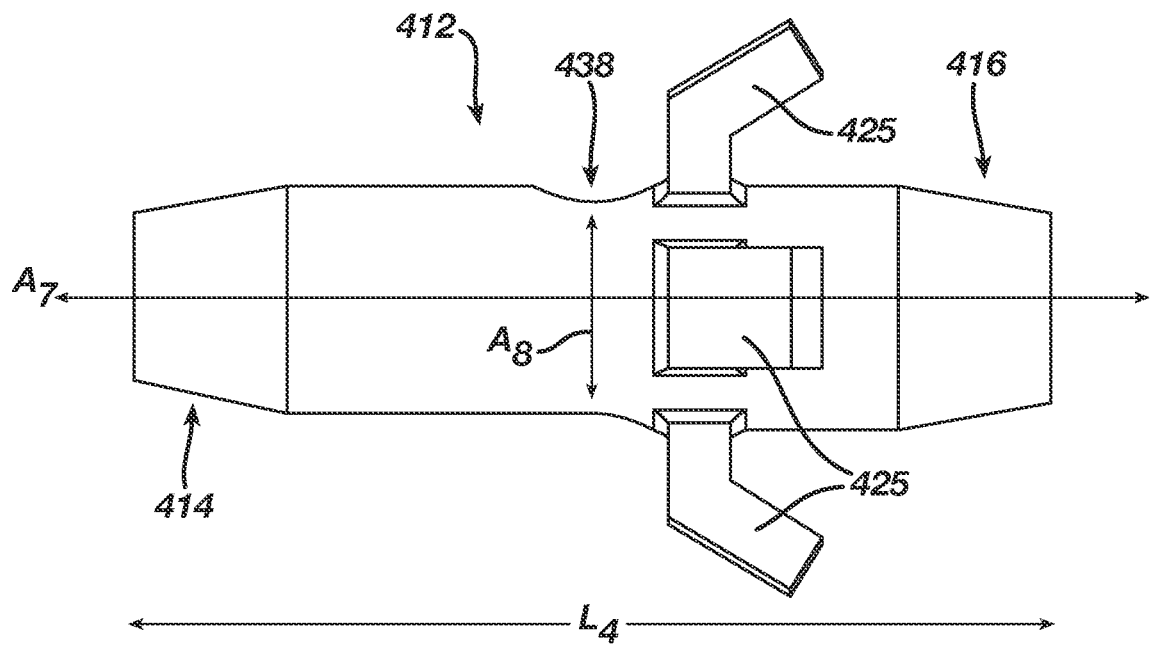
FIG. 14B is a side view of the tissue anchor/catch pledget shown in FIG. 14A.
Figure 14C:
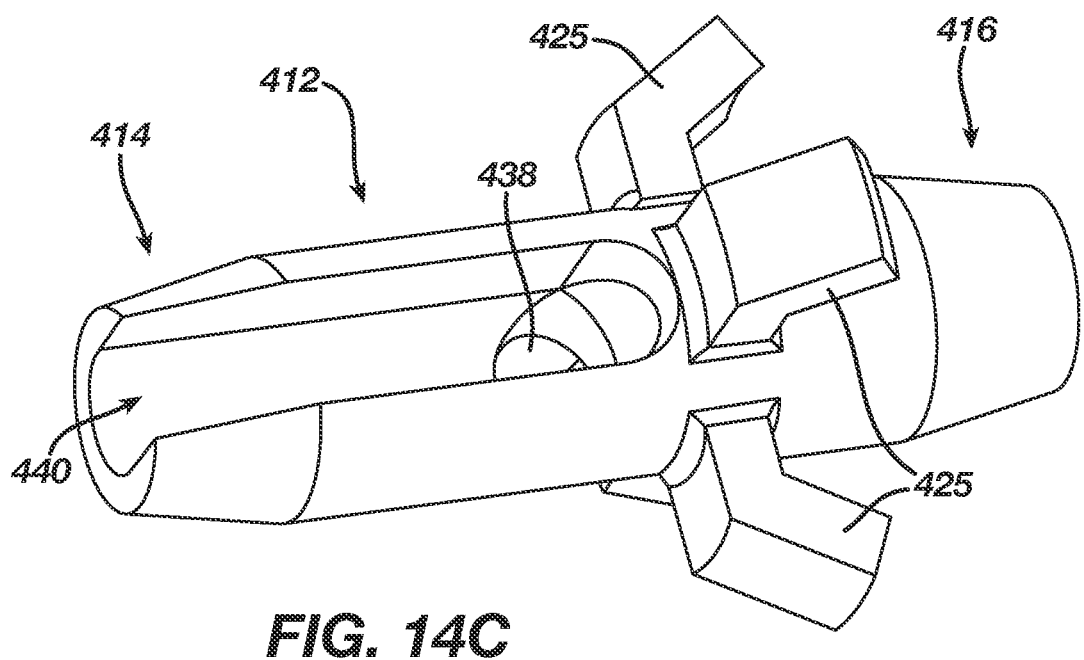
FIG. 14C is a perspective view of an underside of the tissue anchor/catch pledget shown in FIGS. 14A and 14B.

Referring to FIGS. 14A-14C, in one embodiment, a combination tissue anchor/catch pledget 412 may be used in place of the tissue anchor 312 shown and described above in FIGS. 11-13O. In one embodiment, the tissue anchor/catch pledget 412 preferably includes a leading end 414 and a trailing end 416. In one embodiment, the tissue anchor/catch pledget 412 preferably defines a tubular or cylindrical-shaped hollow body. In one embodiment, the leading and trailing ends 414, 416 of the tissue anchor/catch pledget 412 may be tapered.

Referring to FIGS. 14A and 14B, in one embodiment, the tissue anchor/catch pledget 412 preferably has a longitudinal axis $A_7$ that extends along the length $L_4$ thereof. The tissue anchor/catch pledget 412 desirably has an elongated channel 436 that extends along the length $L_4$ of the tissue anchor/catch pledget and between the leading and trailing ends 414, 416 thereof. In one embodiment, the tissue anchor/catch pledget 412 preferably includes a laterally extending channel 438 that extends along a laterally extending axis $A_3$ that traverses (e.g., is perpendicular to) the longitudinal axis $A_7$ of the elongated channel 436.

Referring to FIG. 14C, in one embodiment, the tissue anchor/catch pledget 412 preferably includes an elongated opening 440 that is formed at an underside of the tube-shaped body. The elongated opening 440 is preferably in communication with a proximal segment of the elongated channel 436. In one embodiment, a proximal end of the elongated opening 440 is aligned with the laterally extending channel 438 that extends along the laterally extending axis $A_8$ that traverses the longitudinal axis $A_7$ (FIG. 14B). The elongated opening 440 desirably provides a space or recess that is adapted to receive a slip knot of a suture loop.

Referring to FIGS. 14A-14D, in one embodiment, the tissue anchor/catch pledget 412 preferably includes two or more barbs 425 that project outwardly from the tube-shaped body of the tissue anchor/catch pledget. In one embodiment, the two or more hooks 425 project toward the proximal or trailing end 416 of the tissue anchor/catch pledget 412. During a suturing operation, the two or more barbs 425 are preferably configured for catching onto and/or snagging a suture loop when a sliding suture is pulled for reducing the size of the suture loop and applying tension to tissue to approximate tissue.

Figure 14D:
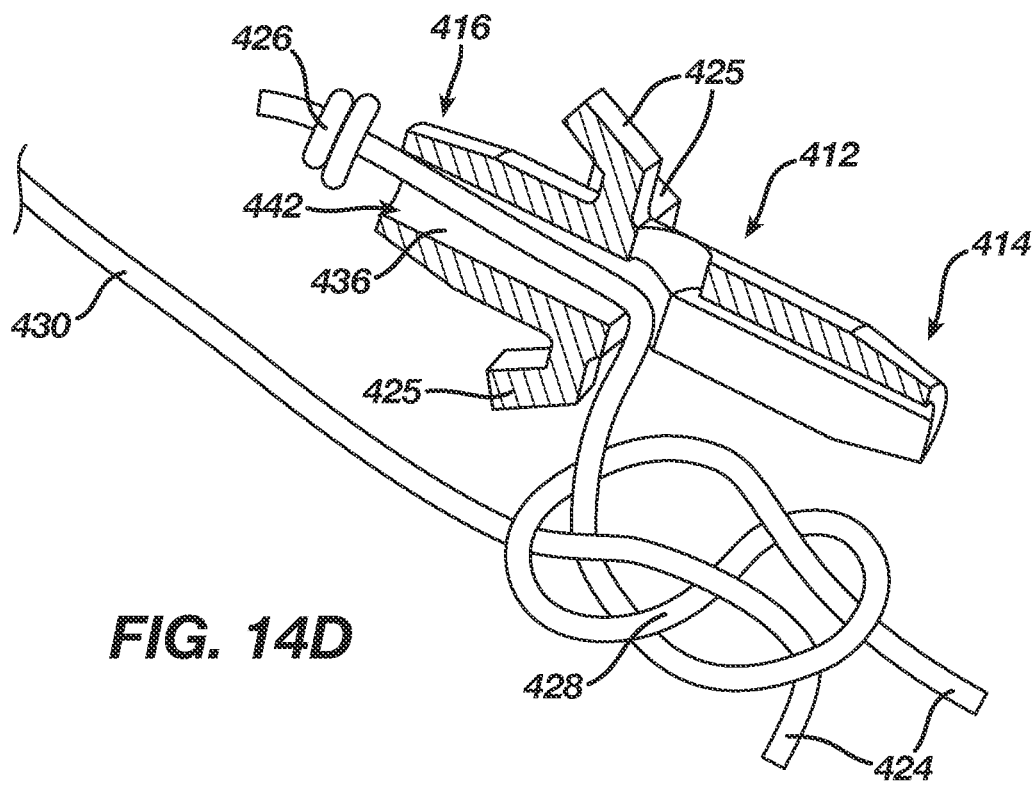
FIG. 14D is a cross-sectional view of the tissue anchor/catch pledget shown in FIGS. 14A-14C.

Referring to FIG. 14D, in one embodiment, the elongated channel 436 preferably extends along the length $L_4$ of the tissue anchor/catch pledge 412. The trailing end of the elongated channel 436 preferably defines a distal opening 442 that is configured to accommodate a fixed knot 426 that is formed at a first end of a suture loop 424. In one embodiment, a slip knot 428 may be located at least partially within the elongated opening 440 (FIG. 14C) and a sliding suture 430 desirably extends out of the slip knot 428. In one embodiment, during a suturing procedure, the sliding suture 430 may be pulled away from the slip knot 428 for reducing the size of the suture loop 424 and applying tension to tissue.

Other Variations

In one embodiment, the suture implants disclosed herein preferably use PDS suture having a size 0 or 2-0.

In one embodiment, the needles may include CTX, CT-1, and CT needles.

In one embodiment, the first and second tissue anchors may have the same configuration and size, or may be individually optimized (i.e., have different configurations and sizes) for their intended functionality In one embodiment, the tissue anchor and/or the catch pledget may have a shape that is not limited to a tubular or cylindrical shape.

In one embodiment, the tissue anchor or catch pledget preferably has a cylindrical shape, which provides a small cross section (i.e., perpendicular to the longitudinal axis) when passing the tissue anchor or catch pledget through the suture loop during implantation to facilitate ease of cinching, however, after being cinched, the longitudinal axis of the tissue anchor or catch pledget is preferably oriented perpendicular to the length of the suture loop to ensure strong suture security.

The tissue anchor or catch pledget may have other geometries for improving security, however, different geometries result in trade-offs in maneuverability through the suture loop during implantation and potentially increased palpability.

Varying configurations of the suture implant device may be more beneficial than others depending upon the application. For example, facial applications require smaller devices due to higher risk of palpability, so smaller device sizes are required.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A suture implant for approximating tissue comprising:
a suture having a first end including a fixed knot, a second end, and a slip knot located between said first and second ends of said suture that defines a suture loop having a length, wherein said slip knot defines a dynamic end of said suture loop that is located opposite a closed end of said suture loop;
a first tissue anchor secured to the first end of said suture by said fixed knot;
a second tissue anchor coupled with the closed end of said suture loop;
a single suture strand having a leading end and a trailing end, wherein the trailing end of said suture strand is attached to a leading end of said first tissue anchor;
a needle having a leading end and a trailing end that is attached to the leading end of said single suture strand;
wherein pulling the second end of said suture away from said slip knot slides said slip knot toward the closed end of said suture loop for reducing a distance between said first and second tissue anchors,
wherein said needle has a maximum cross-sectional dimension, and wherein said first tissue anchor has a maximum cross-sectional dimension that is less than or equal to the maximum cross-sectional dimension of said needle, and
wherein said first end of said suture passes through an elongated channel of said first tissue anchor, and wherein said slip knot is at least partially seated within an elongated opening formed in an underside of said first tissue anchor.

2. The suture implant as claimed in claim 1, wherein the leading end of said first tissue anchor is tapered.

3. The suture implant as claimed in claim 1, wherein said first tissue anchor comprises:
a cylindrical body defining the leading end and the trailing end of said first tissue anchor;
said elongated channel extending from the leading end to a trailing end of said first tissue anchor;
a laterally extending channel that intersects said elongated channel;
said elongated opening formed in said underside of said cylindrical body that extends from the trailing end of said cylindrical body to said laterally extending channel.

4. The suture implant as claimed in claim 3, wherein said fixed knot is aligned with said elongated channel adjacent the trailing end of said first tissue anchor.

5. The suture implant as claimed in claim 1, wherein said second tissue anchor has a cylindrical-shaped body, and wherein an opening that receives said suture loop extends through a center of said cylindrical-shaped body of said second tissue implant.

6. The suture implant as claimed in claim 5, wherein said second tissue anchor is free to slide along the length of said suture loop.

7. The suture implant as claimed in claim 1, wherein said first and second tissue anchors are identical in size, shape, and configuration.

8. A method of using said suture implant of claim 1 for approximating tissue comprising:
passing the leading end of said needle through first and second tissue layers to form a pathway through said first and second tissue layers;
after forming the pathway, using said needle and said single suture strand for pulling said first tissue anchor, said slip knot, and the second end of said suture through the pathway formed in said first and second tissue layers;
after the pulling step, cutting said single suture strand for detaching said needle and said single suture strand from said first tissue anchor;
pulling the second end of said suture loop for sliding said slip knot and said first tissue anchor toward said second tissue anchor for reducing the distance between said first and second tissue anchors and applying tension to said first and second tissue layers.

9. The method as claimed in claim 8, wherein said first tissue anchor is parallel to the length of said suture loop when being pulled through the pathway formed in said first and second tissue layers, and wherein said first and second tissue anchors are perpendicular to the length of said suture loop when applying tension to said first and second tissue layers.

10. The suture implant as claimed in claim 3, wherein, the laterally extending channel is a bore extending through the cylindrical body of the first tissue anchor.

* * * * *